US009801866B2

(12) United States Patent
Duncton et al.

(10) Patent No.: US 9,801,866 B2
(45) Date of Patent: Oct. 31, 2017

(54) FUMARATE ANALOGS AND USES THEREOF

(71) Applicant: RIGEL PHARMACEUTICALS, INC., South San Francisco, CA (US)

(72) Inventors: Matthew Duncton, San Bruno, CA (US); Somasekhar Bhamidipati, Foster City, CA (US); Jiaxin Yu, Foster City, CA (US); Ihab Darwish, San Carlos, CA (US); Rajinder Singh, Belmont, CA (US)

(73) Assignee: Rigl Pharmaceutical, Inc., South San Francisco, CA (US)

( * ) Notice: Subject to any disclaimer, the term of this patent is extended or adjusted under 35 U.S.C. 154(b) by 0 days.

(21) Appl. No.: 15/269,233

(22) Filed: Sep. 19, 2016

(65) Prior Publication Data

US 2017/0065569 A1 Mar. 9, 2017

Related U.S. Application Data

(63) Continuation of application No. 14/815,589, filed on Jul. 31, 2015, now Pat. No. 9,475,781.

(60) Provisional application No. 62/033,023, filed on Aug. 4, 2014.

(51) Int. Cl.
| | | |
|---|---|---|
| *A61K 31/41* | (2006.01) | |
| *C07D 257/04* | (2006.01) | |
| *A61K 31/4439* | (2006.01) | |
| *C07D 401/04* | (2006.01) | |
| *C07D 405/04* | (2006.01) | |
| *C07D 403/12* | (2006.01) | |
| *C07D 405/06* | (2006.01) | |

(52) U.S. Cl.
CPC .......... *A61K 31/4439* (2013.01); *A61K 31/41* (2013.01); *C07D 257/04* (2013.01); *C07D 401/04* (2013.01); *C07D 403/12* (2013.01); *C07D 405/04* (2013.01); *C07D 405/06* (2013.01)

(58) Field of Classification Search
CPC .............................. A61K 31/41; C07D 257/04
USPC .......................................... 548/250; 514/381
See application file for complete search history.

(56) References Cited

U.S. PATENT DOCUMENTS

| 8,148,414 B2 | 4/2012 | Gangakhedkar et al. |
| 8,546,432 B2 * | 10/2013 | Bahadoor ............ C07D 257/04 514/381 |
| 8,669,281 B1 | 3/2014 | Zeidan et al. |
| 2011/0274655 A1 | 11/2011 | Bahadoor et al. |

FOREIGN PATENT DOCUMENTS

EP 0733624 9/1996

OTHER PUBLICATIONS

Dieter, B. J. Diabetes & Metabolism (2014), vol. 6 (1), pp. 1-12.*
Joshi et al, Recent Pat CNS Drug Discovery (2012), vol. 7(3), pp. 218-229.*
Guan et al. (2007) "An Econimical and Convenient Synthesis of Vinyl Sulfones," Synthesis, 10: 1465-1470.
Tiecco et al. (1983) Nucleophilic Substitutions of Unactivated Vinyl Halides with Alkanethiolate Anions in Hexamethylphosphoramide, J. Org. Chem. 48: 4795-4800.
Berge et al. (1977) "Pharmaceutical Salts," J. Pharm. Sci.; 66:1-19.
Kees et al. (1995) "Studies on New Acidic Azoles as Glucose-Lowering Agents in Obese, Diabetic db/db Mice," J. Med. Chem.; 38:617-628.
Lehmann et al. (2007) "Dimethyfumarate Induces Immunosuppression via Glutathione Depletion and Subsequent Induction of Heme Oxygenase 1," Journal of Investigative Dermatology; 127:835-845.
Meissner et al. (2012) "Dimethyl fumarate—only an anti-psoriatic medication?" Journal of the German Society of Dermatology; 10:793-801.
Moharregh-Khiabani et al. (2009) "Fumaric Acid and its Esters: An Emerging Treatment for Multiple Sclerosis," Current Neuropharmacology; 7:60-64.

* cited by examiner

*Primary Examiner* — Kathrien Cruz
*Assistant Examiner* — Janet L Coppins
(74) *Attorney, Agent, or Firm* — Rudy J. Ng; Bozicevic, Field & Francis LLP

(57) ABSTRACT

Aspects of the present disclosure include compounds that find use for the treatment of a variety of autoimmune and inflammatory diseases and disorders. Embodiments of the present disclosure also relate to pharmaceutical compositions that include these compounds, methods of using these compounds in the treatment of various diseases and disorders, processes for preparing these compounds and intermediates useful in these processes.

27 Claims, No Drawings

FUMARATE ANALOGS AND USES THEREOF

CROSS-REFERENCE TO RELATED APPLICATIONS

This application is a continuation of U.S. application Ser. No. 14/815,589, filed Jul. 31, 2015, which claims benefit under 35 U.S.C. §119(e) of U.S. Provisional Application No. 62/033,023, filed Aug. 4, 2014, the disclosures of each of which are incorporated herein by reference in their entirety.

INTRODUCTION

Fumaric acid is an intermediate product of the citric acid cycle. Fumaric acid is a source of intracellular energy in the form of adenosine triphosphate (ATP), and is generated by oxidation of adenylsuccinate by the enzyme succinate dehydrogenase which is then converted to maleate by the enzyme fumarase. Fumaric acid esters (FAE), such as dimethylfumarate (DMF) have been used in the treatment of psoriasis and multiple sclerosis. After oral intake, DMF is rapidly hydrolyzed by esterases to its metabolite monomethyl fumarate (MMF).

Multiple sclerosis (MS), also known as disseminated sclerosis or encephalomyelitis disseminata, is an inflammatory disease in which the insulating covers of nerve cells in the brain and spinal cord are damaged. This damage disrupts the ability of parts of the nervous system to communicate. The three main characteristics of MS are the formation of lesions in the central nervous system (also called plaques), inflammation, and the destruction of myelin sheaths of neurons. MS may be caused by either destruction of the myelin sheaths of neurons by the immune system or failure of the myelin-producing cells.

Psoriasis is a chronic relapsing/remitting immune-mediated skin disease characterized by red, scaly patches, papules, and plaques. There are five main types of psoriasis: plaque, guttate, inverse, pustular, and erythrodermic. Plaque psoriasis is the most common form and typical symptoms are red and white scaly patches on the top layer of the skin. Psoriasis is thought to be caused when the immune system mistakes normal skin cells for a pathogen, and secretes inflammatory chemical signals (cytokines) that cause overproduction of new skin cells.

SUMMARY

Aspects of the present disclosure include compounds that find use for the treatment of a variety of autoimmune and inflammatory diseases and disorders. Embodiments of the present disclosure also relate to pharmaceutical compositions that include these compounds, methods of using these compounds in the treatment of various diseases and disorders, processes for preparing these compounds and intermediates useful in these processes.

Embodiments of the compounds are provided throughout the disclosure. For example, such compounds are represented by the following formula (A):

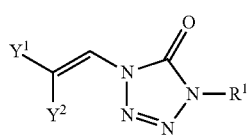

(A)

wherein either:
$Y^1$ is $X^a$ and $Y^2$ is hydrogen, or $Y^2$ is $X^a$ and $Y^1$ is hydrogen;

wherein $X^a$ is selected from carboxylic acid, carboxyl ester, heterocyclyl, substituted heterocyclyl, heteroaryl and substituted heteroaryl; and $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (A);

or a salt or stereoisomer thereof.

In some embodiments of formula (A), the compounds are represented by formula (Ia) or (Ib):

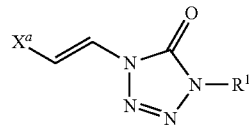

(Ia)

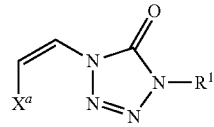

(Ib)

wherein $X^a$ is selected from carboxylic acid, carboxyl ester, heterocyclyl, substituted heterocyclyl, heteroaryl and substituted heteroaryl; and $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (Ia) or (Ib);

or a salt or stereoisomer thereof.

In some embodiments, such compounds are represented by the following formula (Ia):

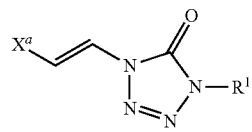

(Ia)

wherein $X^a$ is selected from carboxylic acid, carboxyl ester, heterocyclyl, substituted heterocyclyl, heteroaryl and substituted heteroaryl; and $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$, wherein $R^{15}$ comprises a linking group and a compound of formula (Ia);

or a salt or stereoisomer thereof.

In some embodiments, such compounds are represented by formula (Ib):

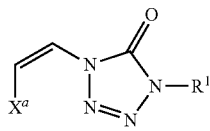

(Ib)

wherein $X^a$ is selected from carboxylic acid, carboxyl ester, heterocyclyl, substituted heterocyclyl, heteroaryl and substituted heteroaryl; and $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$, wherein $R^{15}$ comprises a linking group and a compound of formula (Ib);

or a salt or stereoisomer thereof.

In some embodiments, the compound is a compound of formula (IIa) or (IIb):

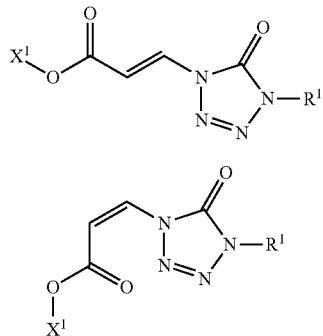

(IIa)

(IIb)

wherein $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (IIa) or (IIb); and $X^1$ is hydrogen, $C_{1-6}$ alkyl or a progroup;

or a salt or stereoisomer thereof.

In some embodiments, the compound is a compound of formula (IIa):

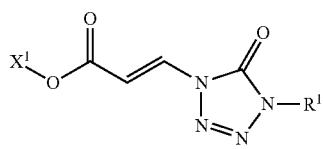

(IIa)

wherein $R^1$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$ where $R^{15}$ includes a linking group and a compound of formula (IIa); and X is $C_{1-6}$ alkyl or a progroup;

or a salt or stereoisomer thereof.

In some embodiments, the compound is a dimer, where $R^{15}$ includes a linking group and a compound of formula (Ia) or (Ib). In some embodiments, the compound is a dimer, where $R^{15}$ includes a linking group and a compound of formula (IIa) or (IIb).

In some embodiments, the compound is a compound of formula (IIb):

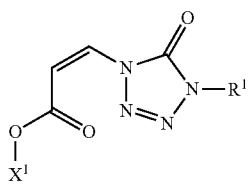

(IIb)

wherein $R^1$ is hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$ where $R^{15}$ includes a linking group and a compound of formula (IIb); and $X^1$ is $C_{1-6}$ alkyl or a progroup;

or a salt or stereoisomer thereof.

Embodiments of the present disclosure also include a pharmaceutical composition that includes a compound as described herein. In some embodiments, the pharmaceutical composition includes a pharmaceutically acceptable carrier.

Embodiments of the present disclosure also include a method of treating a disease or disorder in a subject by administering a pharmaceutically acceptable amount of a compound as described herein sufficient to treat the disease or disorder. In some embodiments, the disease or disorder is an autoimmune disease or an inflammatory disease. In some embodiments, the disease or disorder is psoriasis or multiple sclerosis.

DETAILED DESCRIPTION

Aspects of the present disclosure include compounds that find use for the treatment of a variety of autoimmune and inflammatory diseases and disorders. Embodiments of the present disclosure also relate to pharmaceutical compositions that include these compounds, methods of using these compounds in the treatment of various diseases and disorders, processes for preparing these compounds and intermediates useful in these processes.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a," "an," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

Where a range of values is provided, it is understood that each intervening value, to the tenth of the unit of the lower limit unless the context clearly dictates otherwise, between the upper and lower limit of that range and any other stated or intervening value in that stated range, is specifically contemplated. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

Except as otherwise noted, the methods and techniques of the present embodiments are generally performed according to conventional methods well known in the art and as described in various general and more specific references that are cited and discussed throughout the present specification. See, e.g., Loudon, Organic Chemistry, Fourth Edition, New York: Oxford University Press, 2002, pp. 360-361, 1084-1085; Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978.

The nomenclature used herein to name the subject compounds is illustrated in the Examples herein. This nomenclature has generally been derived using the commercially-available AutoNom software (MDL, San Leandro, Calif.).

Terms

The following terms have the following meanings unless otherwise indicated. Any undefined terms have their art recognized meanings.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3$)$_2$CH—), n-butyl ($CH_3CH_2CH_2CH_2$—), isobutyl (($CH_3$)$_2$CHCH$_2$—), sec-butyl (($CH_3$)($CH_3CH_2$)CH—), t-butyl (($CH_3$)$_3$C—), n-pentyl ($CH_3CH_2CH_2CH_2CH_2$—), and neopentyl (($CH_3$)$_3$CCH$_2$—).

The term "substituted alkyl" refers to an alkyl group as defined herein wherein one or more carbon atoms in the alkyl chain (except the $C_1$ carbon atom) have been optionally replaced with a heteroatom such as —O—, —N—, —S—, —S(O)$_n$— (where n is 0 to 2), —NR— (where R is hydrogen or alkyl) and having from 1 to 5 substituents selected from the group consisting of alkoxy, substituted alkoxy, cycloalkyl, substituted cycloalkyl, cycloalkenyl, substituted cycloalkenyl, acyl, acylamino, acyloxy, amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-aryl, —SO-heteroaryl, —SO$_2$-alkyl, —SO$_2$-aryl, —SO$_2$-heteroaryl, and —NR$^a$R$^b$, wherein R' and R" may be the same or different and are chosen from hydrogen, optionally substituted alkyl, cycloalkyl, alkenyl, cycloalkenyl, alkynyl, aryl, heteroaryl and heterocyclic.

"Alkylene" refers to divalent aliphatic hydrocarbyl groups preferably having from 1 to 6 and more preferably 1 to 3 carbon atoms that are either straight-chained or branched, and which are optionally interrupted with one or more groups selected from —O—, —NR$^{10}$—, —NR$^{10}$C(O)—, —C(O)NR$^{10}$— and the like. This term includes, by way of example, methylene (—CH$_2$—), ethylene (—CH$_2$CH$_2$—), n-propylene (—CH$_2$CH$_2$CH$_2$—), iso-propylene (—CH$_2$CH(CH$_3$)—), (—C(CH$_3$)$_2$CH$_2$CH$_2$—), (—C(CH$_3$)$_2$CH$_2$C(O)—), (—C(CH$_3$)$_2$CH$_2$C(O)NH—), (—CH(CH$_3$)CH$_2$—), and the like.

"Substituted alkylene" refers to an alkylene group having from 1 to 3 hydrogens replaced with substituents as described for carbons in the definition of "substituted" below.

The term "alkane" refers to alkyl group and alkylene group, as defined herein.

The term "alkylaminoalkyl", "alkylaminoalkenyl" and "alkylaminoalkynyl" refers to the groups R'NHR"— where R' is alkyl group as defined herein and R" is alkylene, alkenylene or alkynylene group as defined herein.

The term "alkaryl" or "aralkyl" refers to the groups -alkylene-aryl and -substituted alkylene-aryl where alkylene, substituted alkylene and aryl are defined herein.

"Alkoxy" refers to the group —O-alkyl, wherein alkyl is as defined herein. Alkoxy includes, by way of example, methoxy, ethoxy, n-propoxy, isopropoxy, n-butoxy, t-butoxy, sec-butoxy, n-pentoxy, and the like. The term "alkoxy" also refers to the groups alkenyl-O—, cycloalkyl-O—, cycloalkenyl-O—, and alkynyl-O—, where alkenyl, cycloalkyl, cycloalkenyl, and alkynyl are as defined herein.

The term "substituted alkoxy" refers to the groups substituted alkyl-O—, substituted alkenyl-O—, substituted cycloalkyl-O—, substituted cycloalkenyl-O—, and substituted alkynyl-O— where substituted alkyl, substituted alkenyl, substituted cycloalkyl, substituted cycloalkenyl and substituted alkynyl are as defined herein.

The term "alkoxyamino" refers to the group —NH-alkoxy, wherein alkoxy is defined herein.

The term "haloalkoxy" refers to the groups alkyl-O— wherein one or more hydrogen atoms on the alkyl group have been substituted with a halo group and include, by way of examples, groups such as trifluoromethoxy, and the like.

The term "haloalkyl" refers to a substituted alkyl group as described above, wherein one or more hydrogen atoms on the alkyl group have been substituted with a halo group. Examples of such groups include, without limitation, fluoroalkyl groups, such as trifluoromethyl, difluoromethyl, trifluoroethyl and the like.

The term "alkylalkoxy" refers to the groups -alkylene-O-alkyl, alkylene-O-substituted alkyl, substituted alkylene-O- alkyl, and substituted alkylene-O-substituted alkyl wherein alkyl, substituted alkyl, alkylene and substituted alkylene are as defined herein.

The term "alkylthioalkoxy" refers to the group -alkylene-S-alkyl, alkylene-S-substituted alkyl, substituted alkylene-S-alkyl and substituted alkylene-S-substituted alkyl wherein alkyl, substituted alkyl, alkylene and substituted alkylene are as defined herein.

"Alkenyl" refers to straight chain or branched hydrocarbyl groups having from 2 to 6 carbon atoms and preferably 2 to 4 carbon atoms and having at least 1 and preferably from 1 to 2 sites of double bond unsaturation. This term includes, by way of example, bi-vinyl, allyl, and but-3-en-1-yl. Included within this term are the cis and trans isomers or mixtures of these isomers.

The term "substituted alkenyl" refers to an alkenyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl and —SO$_2$-heteroaryl.

"Alkynyl" refers to straight or branched monovalent hydrocarbyl groups having from 2 to 6 carbon atoms and preferably 2 to 3 carbon atoms and having at least 1 and preferably from 1 to 2 sites of triple bond unsaturation. Examples of such alkynyl groups include acetylenyl (—C≡CH), and propargyl (—CH$_2$C≡CH).

The term "substituted alkynyl" refers to an alkynyl group as defined herein having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO—substituted alkyl, —SO-aryl, —SO-heteroaryl, —SO$_2$-alkyl, —SO$_2$-substituted alkyl, —SO$_2$-aryl, and —SO$_2$-heteroaryl.

"Alkynyloxy" refers to the group —O-alkynyl, wherein alkynyl is as defined herein. Alkynyloxy includes, by way of example, ethynyloxy, propynyloxy, and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, cycloalkenyl-C(O)—, substituted cycloalkenyl-C(O)—, aryl-C(O)—, substituted aryl-C(O)—, heteroaryl-C(O)—, substituted heteroaryl-C(O)—, heterocyclyl-C(O)—, and substituted heterocyclyl-C(O)—, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. For example, acyl includes the "acetyl" group CH$_3$C(O)—

"Acylamino" refers to the groups —NR$^{20}$C(O)alkyl, —NR$^{20}$C(O) substituted alkyl, NR$^{20}$C(O)cycloalkyl, —NR$^{20}$C(O) substituted cycloalkyl, —NR$^{20}$C(O)cycloalkenyl, —NR$^{20}$C(O) substituted cycloalkenyl, —NR$^{20}$C(O) alkenyl, —NR$^{20}$C(O) substituted alkenyl, —NR$^{20}$C(O) alkynyl, —NR$^{20}$C(O) substituted alkynyl, —NR$^{20}$C(O)aryl, —NR$^{20}$C(O) substituted aryl, —NR$^{20}$C(O)heteroaryl, —NR$^{20}$C(O) substituted heteroaryl, —NR$^{20}$C(O)heterocyclic, and —NR$^{20}$C(O) substituted heterocyclic, wherein R$^{20}$ is hydrogen or alkyl and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonyl" or the term "aminoacyl" refers to the group —C(O)NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the nitrogen bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aminocarbonylamino" refers to the group —NR$^{21}$C(O)NR$^{22}$R$^{23}$ where R$^{21}$, R$^{22}$, and R$^{23}$ are independently selected from hydrogen, alkyl, aryl or cycloalkyl, or where two R groups are joined to form a heterocyclyl group.

The term "alkoxycarbonylamino" refers to the group —NRC(O)OR where each R is independently hydrogen, alkyl, substituted alkyl, aryl, heteroaryl, or heterocyclyl wherein alkyl, substituted alkyl, aryl, heteroaryl, and heterocyclyl are as defined herein.

The term "acyloxy" refers to the groups alkyl-C(O)O—, substituted alkyl-C(O)O—, cycloalkyl-C(O)O—, substituted cycloalkyl-C(O)O—, aryl-C(O)O—, heteroaryl-C(O)O—, and heterocyclyl-C(O)O— wherein alkyl, substituted alkyl, cycloalkyl, substituted cycloalkyl, aryl, heteroaryl, and heterocyclyl are as defined herein.

"Aminosulfonyl" refers to the group —SO$_2$NR$^{21}$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, substituted heterocyclic and where R$^{21}$ and R$^{22}$ are optionally joined together with the nitrogen bound thereto to form a heterocyclic or substituted heterocyclic group and alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic and substituted heterocyclic are as defined herein.

"Sulfonylamino" refers to the group —NR$^{21}$SO$_2$R$^{22}$, wherein R$^{21}$ and R$^{22}$ independently are selected from the group consisting of hydrogen, alkyl, substituted alkyl, alkenyl, substituted alkenyl, alkynyl, substituted alkynyl, aryl, substituted aryl, cycloalkyl, substituted cycloalkyl, cycloalkenyl, substituted cycloalkenyl, heteroaryl, substituted heteroaryl, heterocyclic, and substituted heterocyclic and where R$^{21}$ and R$^{22}$ are optionally joined together with the atoms bound thereto to form a heterocyclic or substituted heterocyclic group, and wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Aryl" or "Ar" refers to a monovalent aromatic carbocyclic group of from 6 to 18 carbon atoms having a single ring (such as is present in a phenyl group) or a ring system having multiple condensed rings (examples of such aromatic ring systems include naphthyl, anthryl and indanyl) which condensed rings may or may not be aromatic, provided that the point of attachment is through an atom of an aromatic ring. This term includes, by way of example, phenyl and naphthyl. Unless otherwise constrained by the definition for the aryl substituent, such aryl groups can optionally be substituted with from 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —SO$_2$-alkyl, —SO$_2$-substituted alkyl, —SO$_2$-aryl, —SO$_2$-heteroaryl and trihalomethyl.

"Aryloxy" refers to the group —O-aryl, wherein aryl is as defined herein, including, by way of example, phenoxy, naphthoxy, and the like, including optionally substituted aryl groups as also defined herein.

"Amino" refers to the group —NH$_2$.

The term "substituted amino" refers to the group —NRR where each R is independently selected from the group consisting of hydrogen, alkyl, substituted alkyl, cycloalkyl, substituted cycloalkyl, alkenyl, substituted alkenyl, cycloalkenyl, substituted cycloalkenyl, alkynyl, substituted alkynyl, aryl, heteroaryl, and heterocyclyl provided that at least one R is not hydrogen.

The term "azido" refers to the group —N$_3$.

"Carboxyl," "carboxy" or "carboxylate" refers to —CO$_2$H or salts thereof.

"Carboxyl ester" or "carboxy ester" or the terms "carboxyalkyl" or "carboxylalkyl" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-cycloalkenyl, —C(O)O-substituted cycloalkenyl, —C(O)O-heteroaryl, —C(O)O-substituted heteroaryl, —C(O)O-heterocyclic, and —C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"(Carboxyl ester)oxy" or "carbonate" refers to the groups —O—C(O)O-alkyl, —O—C(O)O-substituted alkyl, —O—C(O)O-alkenyl, —O—C(O)O-substituted alkenyl, —O—C(O)O—alkynyl, —O—C(O)O-substituted alkynyl, —O—C(O)O-aryl, —O—C(O)O-substituted aryl, —O—C(O)O—cycloalkyl, —O—C(O)O-substituted cycloalkyl, —O—C(O)O-cycloalkenyl, —O—C(O)O-substituted cycloalkenyl, —O—C(O)O-heteroaryl, —O—C(O)O-substituted heteroaryl, —O—C(O)O-heterocyclic, and —O—C(O)O-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

"Cyano" or "nitrile" refers to the group —CN.

"Cycloalkyl" refers to cyclic alkyl groups of from 3 to 10 carbon atoms having single or multiple cyclic rings including fused, bridged, and spiro ring systems. Examples of suitable cycloalkyl groups include, for instance, adamantyl, cyclopropyl, cyclobutyl, cyclopentyl, cyclooctyl and the like. Such cycloalkyl groups include, by way of example, single ring structures such as cyclopropyl, cyclobutyl, cyclopentyl, cyclooctyl, and the like, or multiple ring structures such as adamantanyl, and the like.

The term "substituted cycloalkyl" refers to cycloalkyl groups having from 1 to 5 substituents, or from 1 to 3 substituents, selected from alkyl, substituted alkyl, alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkenyl" refers to non-aromatic cyclic alkyl groups of from 3 to 10 carbon atoms having single or multiple rings and having at least one double bond and preferably from 1 to 2 double bonds.

The term "substituted cycloalkenyl" refers to cycloalkenyl groups having from 1 to 5 substituents, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, keto, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —SO$_2$-alkyl, —SO$_2$-substituted alkyl, —SO$_2$-aryl and —SO$_2$-heteroaryl.

"Cycloalkynyl" refers to non-aromatic cycloalkyl groups of from 5 to 10 carbon atoms having single or multiple rings and having at least one triple bond.

"Cycloalkoxy" refers to —O-cycloalkyl.

"Cycloalkenyloxy" refers to —O-cycloalkenyl.

"Halo" or "halogen" refers to fluoro, chloro, bromo, and iodo.

"Hydroxy" or "hydroxyl" refers to the group —OH.

"Heteroaryl" refers to an aromatic group of from 1 to 15 carbon atoms, such as from 1 to 10 carbon atoms and 1 to 10 heteroatoms selected from the group consisting of oxygen, nitrogen, and sulfur within the ring. Such heteroaryl groups can have a single ring (such as, pyridinyl, imidazolyl or furyl) or multiple condensed rings in a ring system (for example as in groups such as, indolizinyl, quinolinyl, benzofuran, benzimidazolyl or benzothienyl), wherein at least one ring within the ring system is aromatic and at least one ring within the ring system is aromatic, provided that the point of attachment is through an atom of an aromatic ring. In certain embodiments, the nitrogen and/or sulfur ring atom(s) of the heteroaryl group are optionally oxidized to provide for the N-oxide (N→O), sulfinyl, or sulfonyl moieties. This term includes, by way of example, pyridinyl, pyrrolyl, indolyl, thiophenyl, and furanyl. Unless otherwise constrained by the definition for the heteroaryl substituent, such heteroaryl groups can be optionally substituted with 1 to 5 substituents, or from 1 to 3 substituents, selected from acyloxy, hydroxy, thiol, acyl, alkyl, alkoxy, alkenyl, alkynyl, cycloalkyl, cycloalkenyl, substituted alkyl, substituted alkoxy, substituted alkenyl, substituted alkynyl, substituted cycloalkyl, substituted cycloalkenyl, amino, substituted amino, aminoacyl, acylamino, alkaryl, aryl, aryloxy, azido, carboxyl, carboxylalkyl, cyano, halogen, nitro, heteroaryl, heteroaryloxy, heterocyclyl, heterocyclooxy, aminoacyloxy, oxyacylamino, thioalkoxy, substituted thioalkoxy, thioaryloxy, thioheteroaryloxy, —SO-alkyl, —SO-substituted alkyl, —SO-aryl, —SO-heteroaryl, —$SO_2$— alkyl, —$SO_2$-substituted alkyl, —$SO_2$-aryl and —$SO_2$-heteroaryl, and trihalomethyl.

The term "heteroaralkyl" refers to the groups -alkylene-heteroaryl where alkylene and heteroaryl are defined herein. This term includes, by way of example, pyridylmethyl, pyridylethyl, indolylmethyl, and the like.

"Heteroaryloxy" refers to —O-heteroaryl.

"Heterocycle," "heterocyclic," "heterocycloalkyl," and "heterocyclyl" refer to a saturated or unsaturated group having a single ring or multiple condensed rings, including fused bridged and spiro ring systems, and having from 3 to 20 ring atoms, including 1 to 10 hetero atoms. These ring atoms are selected from the group consisting of nitrogen, sulfur, or oxygen, wherein, in fused ring systems, one or more of the rings can be cycloalkyl, aryl, or heteroaryl, provided that the point of attachment is through the non-aromatic ring. In certain embodiments, the nitrogen and/or sulfur atom(s) of the heterocyclic group are optionally oxidized to provide for the N-oxide, —S(O)—, or —$SO_2$— moieties.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thiamorpholinyl), 1,1-dioxothiomorpholinyl, piperidinyl, pyrrolidine, tetrahydrofuranyl, and the like.

Unless otherwise constrained by the definition for the heterocyclic substituent, such heterocyclic groups can be optionally substituted with 1 to 5, or from 1 to 3 substituents, selected from alkoxy, substituted alkoxy, cycloalkyl, substituted cycloalkyl, cycloalkenyl, substituted cycloalkenyl, acyl, acylamino, acyloxy, amino, substituted amino, aminoacyl, aminoacyloxy, oxyaminoacyl, azido, cyano, halogen, hydroxyl, oxo, thioketo, carboxyl, carboxylalkyl, thioaryloxy, thioheteroaryloxy, thioheterocyclooxy, thiol, thioalkoxy, substituted thioalkoxy, aryl, aryloxy, heteroaryl, heteroaryloxy, heterocyclyl, heterocyclooxy, hydroxyamino, alkoxyamino, nitro, —SO-alkyl, —SO-substituted alkyl, —SO-aryl, —SO-heteroaryl, —$SO_2$-alkyl, —$SO_2$-substituted alkyl, —$SO_2$-aryl, —$SO_2$-heteroaryl, and fused heterocycle.

"Heterocyclyloxy" refers to the group —O-heterocyclyl.
The term "heterocyclylthio" refers to the group heterocyclic-S—.
The term "heterocyclene" refers to the diradical group formed from a heterocycle, as defined herein.
The term "hydroxyamino" refers to the group —NHOH.
"Nitro" refers to the group —$NO_2$.
"Oxo" refers to the atom (=O).
"Sulfonyl" refers to the group $SO_2$-alkyl, $SO_2$-substituted alkyl, $SO_2$-alkenyl, $SO_2$-substituted alkenyl, $SO_2$-cycloalkyl, $SO_2$-substituted cycloalkyl, $SO_2$-cycloalkenyl, $SO_2$-substituted cylcoalkenyl, $SO_2$-aryl, $SO_2$-substituted aryl, $SO_2$-heteroaryl, $SO_2$-substituted heteroaryl, $SO_2$-heterocyclic, and $SO_2$-substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein. Sulfonyl includes, by way of example, methyl-$SO_2$—, phenyl-$SO_2$—, and 4-methylphenyl-$SO_2$—.

"Sulfonyloxy" refers to the group —$OSO_2$-alkyl, $OSO_2$-substituted alkyl, $OSO_2$-alkenyl, $OSO_2$-substituted alkenyl, $OSO_2$-cycloalkyl, $OSO_2$-substituted cycloalkyl, $OSO_2$-cycloalkenyl, $OSO_2$-substituted cylcoalkenyl, $OSO_2$-aryl, $OSO_2$-substituted aryl, $OSO_2$-heteroaryl, $OSO_2$-substituted heteroaryl, $OSO_2$-heterocyclic, and $OSO_2$ substituted heterocyclic, wherein alkyl, substituted alkyl, alkenyl, substituted alkenyl, alkynyl, substituted alkynyl, cycloalkyl, substituted cycloalkyl, cycloalkenyl, substituted cycloalkenyl, aryl, substituted aryl, heteroaryl, substituted heteroaryl, heterocyclic, and substituted heterocyclic are as defined herein.

The term "aminocarbonyloxy" refers to the group —OC(O)NRR where each R is independently hydrogen, alkyl, substituted alkyl, aryl, heteroaryl, or heterocyclic wherein alkyl, substituted alkyl, aryl, heteroaryl and heterocyclic are as defined herein.

"Thiol" refers to the group —SH.
"Thioxo" or the term "thioketo" refers to the atom (=S).
"Alkylthio" or the term "thioalkoxy" refers to the group —S-alkyl, wherein alkyl is as defined herein. In certain embodiments, sulfur may be oxidized to —S(O)—. The sulfoxide may exist as one or more stereoisomers.

The term "substituted thioalkoxy" refers to the group —S-substituted alkyl.

The term "thioaryloxy" refers to the group aryl-S— wherein the aryl group is as defined herein including optionally substituted aryl groups also defined herein.

The term "thioheteroaryloxy" refers to the group heteroaryl-S— wherein the heteroaryl group is as defined herein including optionally substituted aryl groups as also defined herein.

The term "thioheterocyclooxy" refers to the group heterocyclyl-S— wherein the heterocyclyl group is as defined herein including optionally substituted heterocyclyl groups as also defined herein.

In addition to the disclosure herein, the term "substituted," when used to modify a specified group or radical, can also mean that one or more hydrogen atoms of the specified group or radical are each, independently of one another, replaced with the same or different substituent groups as defined below.

In addition to the groups disclosed with respect to the individual terms herein, substituent groups for substituting for one or more hydrogens (any two hydrogens on a single carbon can be replaced with =O, =NR⁷⁰, =N—OR⁷⁰, =N₂ or =S) on saturated carbon atoms in the specified group or radical are, unless otherwise specified, —R⁶⁰, halo, =O, —OR⁷⁰, —SR⁷⁰, —NR⁸⁰R⁸⁰, trihalomethyl, —CN, —OCN, —SCN, —NO, —NO₂, =N₂, —N₃, —SO₂R⁷⁰, —SO₂O⁻M⁺, —SO₂OR⁷⁰, —OSO₂R⁷⁰, —OSO₂O⁻M⁺, —OSO₂OR⁷⁰, —P(O)(O⁻)₂(M⁺)₂, —P(O)(OR⁷⁰)O⁻M⁺, —P(O)(OR⁷⁰)₂, —C(O)R⁷⁰, —C(S)R⁷⁰, —C(NR⁷⁰)R⁷⁰, —C(O)O⁻M⁺, —C(O)OR⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OC(O)O⁻M⁺, —OC(O)OR⁷⁰, —OC(S)OR⁷⁰. —NR⁷⁰C(O)R⁷⁰, —NR⁷⁰C(S)R⁷⁰, —NR⁷⁰CO₂⁻M⁺, —NR⁷⁰CO₂R⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where $R^{60}$ is selected from the group consisting of optionally substituted alkyl, cycloalkyl, heteroalkyl, heterocycloalkylalkyl, cycloalkylalkyl, aryl, arylalkyl, heteroaryl and heteroarylalkyl, each $R^{70}$ is independently hydrogen or $R^{60}$; each $R^{80}$ is independently $R^{70}$ or alternatively, two $R^{80}$, taken together with the nitrogen atom to which they are bonded, form a 5-, 6- or 7-membered heterocycloalkyl which may optionally include from 1 to 4 of the same or different additional heteroatoms selected from the group consisting of O, N and S, of which N may have —H or $C_1$-$C_3$ alkyl substitution; and each $M^+$ is a counter ion with a net single positive charge. Each $M^+$ may independently be, for example, an alkali ion, such as $K^+$, $Na^+$, $Li^+$; an ammonium ion, such as $^+N(R^{60})_4$; or an alkaline earth ion, such as $[Ca^{2+}]_{0.5}$, $[Mg^{2+}]_{0.5}$, or $[Ba^{2+}]_{0.5}$ ("subscript 0.5 means that one of the counter ions for such divalent alkali earth ions can be an ionized form of a compound of the invention and the other a typical counter ion such as chloride, or two ionized compounds disclosed herein can serve as counter ions for such divalent alkali earth ions, or a doubly ionized compound of the invention can serve as the counter ion for such divalent alkali earth ions). As specific examples, —NR⁸⁰R⁸⁰ is meant to include —NH₂, —NH-alkyl, N-pyrrolidinyl, N-piperazinyl, 4N-methyl-piperazin-1-yl and N-morpholinyl.

In addition to the disclosure herein, substituent groups for hydrogens on unsaturated carbon atoms in "substituted" alkene, alkyne, aryl and heteroaryl groups are, unless otherwise specified, —R⁶⁰, halo, —O⁻M⁺, —OR⁷⁰, —SR⁷⁰, —S⁻M⁺, —NR⁸⁰R⁸⁰, trihalomethyl, —CF₃, —CN, —OCN, —SCN, —NO, —NO₂, —N₃, —SO₂R⁷⁰, —SO₃⁻M⁺, —SO₃R⁷⁰, —OSO₂R⁷⁰, —OSO₃⁻M⁺, —OSO₃R⁷⁰, —PO₃⁻² (M⁺)₂, —P(O)(OR⁷⁰)O⁻M⁺, —P(O)(OR⁷⁰)₂, —C(O)R⁷⁰, —C(S)R⁷⁰, —C(NR⁷⁰)R⁷⁰, —CO₂⁻M⁺, —CO₂R⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OCO₂⁻M⁺, —OCO₂R⁷⁰, —OC(S)OR⁷⁰, —NR⁷⁰C(O)R⁷⁰, —NR⁷⁰C(S)R⁷⁰, —NR⁷⁰CO₂⁻M⁺, —NR⁷⁰CO₂R⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where $R^{60}$, $R^{70}$, $R^{80}$ and $M^+$ are as previously defined, provided that in case of substituted alkene or alkyne, the substituents are not —O⁻M⁺, —OR⁷⁰, —SR⁷⁰, or —S⁻M⁺.

In addition to the groups disclosed with respect to the individual terms herein, substituent groups for hydrogens on nitrogen atoms in "substituted" heteroalkyl and cycloheteroalkyl groups are, unless otherwise specified, —R⁶⁰, —O⁻M⁺, —OR⁷⁰, —SR⁷⁰, —S⁻M⁺, —NR⁸⁰R⁸⁰, trihalomethyl, —CF₃, —CN, —NO, —NO₂, —S(O)₂R⁷⁰, —S(O)₂O⁻M⁺, —S(O)₂OR⁷⁰, —OS(O)₂R⁷⁰, —OS(O)₂O⁻M⁺, —OS(O)₂OR⁷⁰, —P(O)(O⁻)₂(M⁺)₂, —P(O)(OR⁷⁰)O⁻M⁺, —P(O)(OR⁷⁰)(OR⁷⁰), —C(O)R⁷⁰, —C(S)R⁷⁰, —C(NR⁷⁰)R⁷⁰, —C(O)OR⁷⁰, —C(S)OR⁷⁰, —C(O)NR⁸⁰R⁸⁰, —C(NR⁷⁰)NR⁸⁰R⁸⁰, —OC(O)R⁷⁰, —OC(S)R⁷⁰, —OC(O)OR⁷⁰, —OC(S)OR⁷⁰, —NR⁷⁰C(O)R⁷⁰, —NR⁷⁰C(S)R⁷⁰, —NR⁷⁰C(O)OR⁷⁰, —NR⁷⁰C(S)OR⁷⁰, —NR⁷⁰C(O)NR⁸⁰R⁸⁰, —NR⁷⁰C(NR⁷⁰)R⁷⁰ and —NR⁷⁰C(NR⁷⁰)NR⁸⁰R⁸⁰, where $R^{60}$, $R^{70}$, $R^{80}$ and $M^+$ are as previously defined.

In addition to the disclosure herein, in a certain embodiment, a group that is substituted has 1, 2, 3, or 4 substituents, 1, 2, or 3 substituents, 1 or 2 substituents, or 1 substituent.

It is understood that in all substituted groups defined above, polymers arrived at by defining substituents with further substituents to themselves (e.g., substituted aryl having a substituted aryl group as a substituent which is itself substituted with a substituted aryl group, which is further substituted by a substituted aryl group, etc.) are not intended for inclusion herein. In such cases, the maximum number of such substitutions is three. For example, serial substitutions of substituted aryl groups specifically contemplated herein are limited to substituted aryl-(substituted aryl)-substituted aryl.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

As to any of the groups disclosed herein which contain one or more substituents, it is understood, of course, that such groups do not contain any substitution or substitution patterns which are sterically impractical and/or synthetically non-feasible. In addition, the subject compounds include all stereochemical isomers arising from the substitution of these compounds.

The term "pharmaceutically acceptable salt" means a salt which is acceptable for administration to a patient, such as a mammal (salts with counterions having acceptable mammalian safety for a given dosage regime). Such salts can be derived from pharmaceutically acceptable inorganic or organic bases and from pharmaceutically acceptable inorganic or organic acids. "Pharmaceutically acceptable salt" refers to pharmaceutically acceptable salts of a compound, which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, formate, tartrate, besylate, mesylate, acetate, maleate, oxalate, and the like.

The term "salt thereof" means a compound formed when a proton of an acid is replaced by a cation, such as a metal cation or an organic cation and the like. Where applicable, the salt is a pharmaceutically acceptable salt, although this is not required for salts of intermediate compounds that are not intended for administration to a patient. By way of example, salts of the present compounds include those wherein the compound is protonated by an inorganic or organic acid to form a cation, with the conjugate base of the inorganic or organic acid as the anionic component of the salt.

"Solvate" refers to a complex formed by combination of solvent molecules with molecules or ions of the solute. The solvent can be an organic compound, an inorganic compound, or a mixture of both. Some examples of solvents include, but are not limited to, methanol, N,N-dimethylformamide, tetrahydrofuran, dimethylsulfoxide, and water. When the solvent is water, the solvate formed is a hydrate.

"Stereoisomer" and "stereoisomers" refer to compounds that have same atomic connectivity but different atomic arrangement in space. Stereoisomers include cis-trans isomers, E and Z isomers, enantiomers, and diastereomers.

"Tautomer" refers to alternate forms of a molecule that differ only in electronic bonding of atoms and/or in the position of a proton, such as enol-keto and imine-enamine tautomers, or the tautomeric forms of heteroaryl groups containing a —N=C(H)—NH— ring atom arrangement, such as pyrazoles, imidazoles, benzimidazoles, triazoles, and tetrazoles. A person of ordinary skill in the art would recognize that other tautomeric ring atom arrangements are possible.

It will be appreciated that the term "or a salt or solvate or stereoisomer thereof" is intended to include all permutations of salts, solvates and stereoisomers, such as a solvate of a pharmaceutically acceptable salt of a stereoisomer of subject compound.

"Pharmaceutically effective amount" and "therapeutically effective amount" refer to an amount of a compound sufficient to treat a specified disorder or disease or one or more of its symptoms and/or to prevent the occurrence of the disease or disorder. In reference to tumorigenic proliferative disorders, a pharmaceutically or therapeutically effective amount comprises an amount sufficient to, among other things, cause the tumor to shrink or decrease the growth rate of the tumor.

"Patient" refers to human and non-human subjects, especially mammalian subjects.

The term "treating" or "treatment" as used herein means the treating or treatment of a disease or medical condition in a patient, such as a mammal (particularly a human) that includes: (a) preventing the disease or medical condition from occurring, such as, prophylactic treatment of a subject; (b) ameliorating the disease or medical condition, such as, eliminating or causing regression of the disease or medical condition in a patient; (c) suppressing the disease or medical condition, for example by, slowing or arresting the development of the disease or medical condition in a patient; or (d) alleviating a symptom of the disease or medical condition in a patient.

REPRESENTATIVE EMBODIMENTS

The following substituents and values are intended to provide representative examples of various aspects and embodiments. These representative values are intended to further define and illustrate such aspects and embodiments and are not intended to exclude other embodiments or to limit the scope of the present disclosure. In this regard, the representation that a particular value or substituent is preferred is not intended in any way to exclude other values or substituents from the present disclosure unless specifically indicated.

These compounds may contain one or more chiral centers and therefore, the embodiments are directed to racemic mixtures; pure stereoisomers (i.e., enantiomers or diastereomers); stereoisomer-enriched mixtures and the like unless otherwise indicated. When a particular stereoisomer is shown or named herein, it will be understood by those skilled in the art that minor amounts of other stereoisomers may be present in the compositions unless otherwise indicated, provided that the desired utility of the composition as a whole is not eliminated by the presence of such other isomers.

The compositions of the present disclosure include compounds of the formulae shown below. Pharmaceutical compositions and methods of the present disclosure also contemplate compounds of the following formulae.

Formula A

Embodiments of the compounds are represented by the following formula (A):

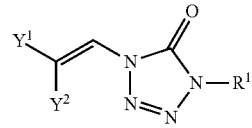

(A)

wherein either $Y^1$ is $X^a$ and $Y^2$ is hydrogen, or $Y^2$ is $X^a$ and $Y^1$ is hydrogen;

wherein $X^a$ is selected from carboxylic acid, carboxyl ester, heterocyclyl, substituted heterocyclyl, heteroaryl and substituted heteroaryl; and $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (A);

or a salt or stereoisomer thereof.

Formulae (Ia) and (Ib)

In some embodiments of formula (A), the compounds are represented by formula (Ia) or (Ib):

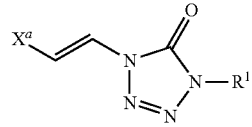

(Ia)

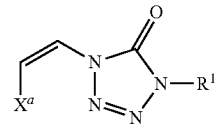

(Ib)

wherein $X^a$ is selected from carboxylic acid, carboxyl ester, heterocyclyl, substituted heterocyclyl, heteroaryl and substituted heteroaryl; and $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (Ia) or (Ib);

or a salt or stereoisomer thereof.

Embodiments of the present disclosure include a compound of formula (Ia):

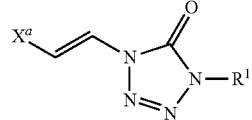

(Ia)

wherein

X$^a$ is selected from carboxylic acid, carboxyl ester, heterocyclyl, substituted heterocyclyl, heteroaryl and substituted heteroaryl; and R$^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —R$^{15}$, or a salt or stereoisomer thereof.

Embodiments of the present disclosure include a compound of formula (Ib):

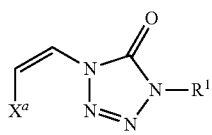

(Ib)

wherein

X$^a$ is selected from carboxylic acid, carboxyl ester, heterocyclyl, substituted heterocyclyl, heteroaryl and substituted heteroaryl; and R$^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —R$^{15}$, or a salt or stereoisomer thereof.

In some embodiments of formulae (Ia) and (Ib), the compound is a dimer, where R$^{15}$ includes a linking group and a compound of formulae (Ia) or (Ib). In certain embodiments, the compound is a symmetrical dimer. In certain embodiments, the compound is an unsymmetrical dimer. In some instances of formulae (Ia) and (Ib), R$^{15}$ includes a linking group and a compound of formula (Ia). In some instances of formulae (Ia) and (Ib), R$^{15}$ includes a linking group and a compound of formula (Ib).

In certain embodiments, X$^a$ is selected from carboxylic acid, carboxyl ester, heterocyclyl, substituted heterocyclyl, heteroaryl and substituted heteroaryl. In certain embodiments, X$^a$ is a carboxylic acid. In certain embodiments, X$^a$ is a carboxyl ester. In certain embodiments, X$^a$ is heterocyclyl or substituted heterocyclyl. In certain embodiments, X$^a$ is heteroaryl or substituted heteroaryl.

In certain embodiments, X$^a$ is a heterocyclyl or a heteroaryl as described above. In certain embodiments, the heterocyclyl or heteroaryl described above is substituted with one or more substituents. For example, in certain embodiments, the substituent on X$^a$ is a C$_{1-6}$ alkyl or a progroup. In certain embodiments, the substituent on X$^a$ is C$_{1-6}$ alkyl. In certain embodiments, the substituent on X$^a$ is methyl. In certain embodiments, the substituent on X$^a$ is ethyl. In certain embodiments, the substituent on X$^a$ is propyl. In certain embodiments, the substituent on X$^a$ is butyl. In certain embodiments, the substituent on X$^a$ is pentyl. In certain embodiments, the substituent on X$^a$ is hexyl. The C$_{1-6}$ alkyl may be unbranched or branched. For example, the substituent on X$^1$ may be propyl, such as n-propyl or iso-propyl. For example, the substituent on X$^1$ may be butyl, such as n-butyl, sec-butyl (1-methylpropyl), iso-butyl (2-methylpropyl) or tert-butyl (1,1-dimethylethyl).

In certain embodiments, the substituent on X$^a$ is a progroup. For example, the compounds described herein can be provided in prodrug form. "Prodrug" refers to a derivative of an active compound (e.g., a drug) that undergoes a transformation under the conditions of use, such as within the body, to release the active compound. Prodrugs may be, but are not necessarily, pharmacologically inactive until converted into the active drug. Prodrugs may be obtained by masking a functional group in the drug believed to be in part required for activity with a progroup to form a promoiety which undergoes a transformation, such as cleavage, under the specified conditions of use to release the functional group, and hence the active drug. The cleavage of the promoiety can proceed spontaneously, such as by way of a hydrolysis reaction, or it can be catalyzed or induced by another agent, such as by an enzyme, by light, by acid, or by a change of or exposure to a physical or environmental parameter, such as a change of temperature. The agent can be endogenous to the conditions of use, such as an enzyme present in the cells to which the prodrug is administered or the acidic conditions of the stomach, or it can be supplied exogenously. In certain cases, compounds that include a progroup may facilitate an increase in gastrointestinal permeability, an increase in gastrointestinal absorption, and/or an increase in solubility of the compound. In certain cases, compounds that include a progroup may facilitate removal of the progroup at a desired site of action for the pharmaceutically active form of the compound, or after a desired amount of time after administration of the compound (e.g., delayed release formulations, controlled release formulations, and the like). A wide variety of progroups, as well as the resultant promoieties, suitable for masking functional groups in the active drugs to yield prodrugs may be used. For example, a hydroxyl functional group can be masked as a sulfonate, ester or carbonate promoiety, which can be hydrolyzed in vivo to provide the hydroxyl group. An amino functional group can be masked as an amide, carbamate, imine, urea, phosphenyl, phosphoryl or sulfenyl promoiety, which can be hydrolyzed in vivo to provide the amino group. A carboxyl group can be masked as an ester (including silyl esters and thioesters), amide or hydrazide promoiety, which can be hydrolyzed in vivo to provide the carboxyl group. Specific examples of suitable progroups and their respective promoieties will be apparent to those of skill in the art. Embodiments of progroups according to the present disclosure are also described in more detail below.

In certain embodiments, X$^a$ is a heterocyclyl or a heteroaryl as described above. Examples of heterocyclyl and heteroaryl groups include, but are not limited to, oxazole, oxadiazole (e.g., 1,2,3-oxadiazole, 1,3,4-oxadiazole, 1,2,4-oxadiazole), tetrazole, tetrazolone, thiazole, thiadiazole (e.g., 1,2,3-thiadiazole, 1,3,4-thiadiazole, 1,2,4-thiadiazole), and the like. In certain embodiments, the substituent on X$^a$ may be X$^1$ as described in more detail below regarding compounds of formula (IIa) and (IIb). For example, compounds of formula (Ia) may be selected from the following compounds:

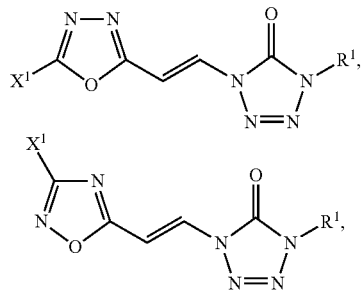

-continued
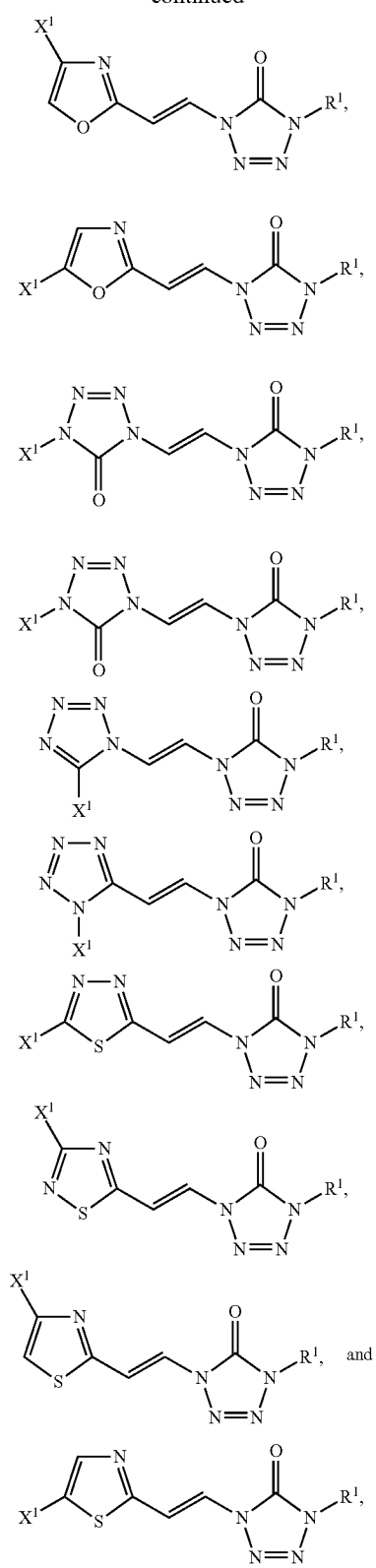
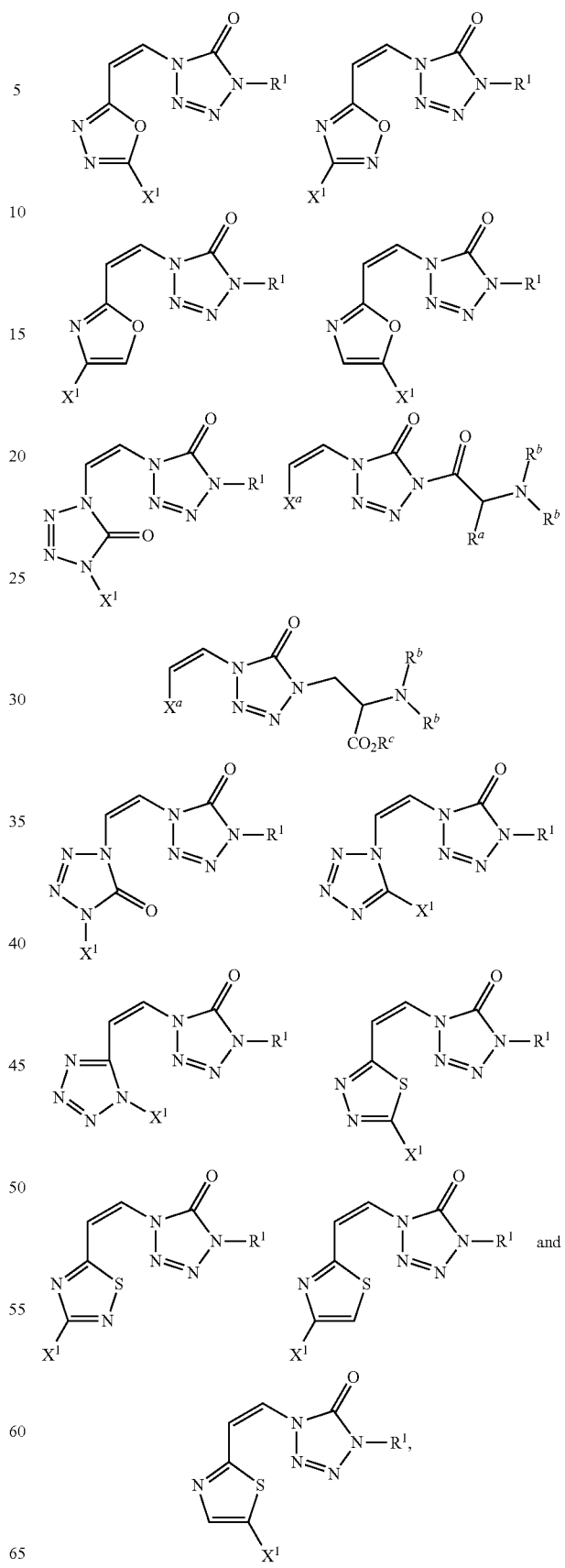
wherein $X^1$ and $R^1$ are as described below regarding compounds of formulae (Ia), (Ib), (IIa) and (IIb).
In some embodiments, compounds of formula (Ib) may be selected from the following compounds:

wherein $X^1$ and $R^1$ are as described below regarding compounds of formulae (Ia), (b), (IIa) and (IIb).

In certain embodiments, $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$.

In certain embodiments, $R^1$ is hydrogen. In certain embodiments, $R^1$ is alkyl or substituted alkyl. In certain embodiments, $R^1$ is alkenyl or substituted alkenyl. In certain embodiments, $R^1$ is alkynyl or substituted alkynyl. In certain embodiments, $R^1$ is cycloalkyl or substituted cycloalkyl. In certain embodiments, $R^1$ is cyclohexyl or substituted cyclohexyl. In certain embodiments, $R^1$ is cyclopentyl or substituted cyclopentyl. In certain embodiments, $R^1$ is cyclobutyl or substituted cyclobutyl. In certain embodiments, $R^1$ is cyclopropyl or substituted cyclopropyl. In certain embodiments, $R^1$ is heterocyclyl or substituted heterocyclyl. In certain embodiments, $R^1$ is 4-tetrahydropyranyl or substituted 4-tetrahydropyranyl. In certain embodiments, $R^1$ is aryl or substituted aryl. In certain embodiments, $R^1$ is phenyl or substituted phenyl. In certain embodiments, $R^1$ is heteroaryl or substituted heteroaryl. In certain embodiments, $R^1$ is pyridyl or substituted pyridyl. In certain embodiments, $R^1$ is a 2-pyridyl, a 3-pyridyl or 4-pyridyl. In certain embodiments, $R^1$ is a substituted 2-pyridyl, a substituted 3-pyridyl or a substituted 4-pyridyl.

In certain embodiments, $R^1$ is a substituted alkenyl. In certain embodiments, the compound is of one of the following formulae:

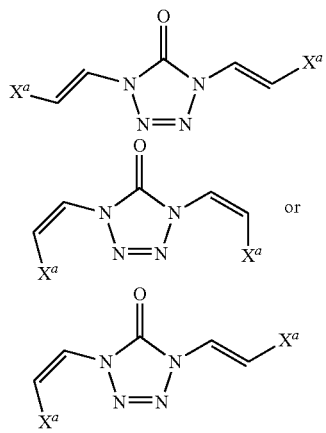

wherein each $X^a$ is as described above; or a salt or stereoisomer thereof.

In certain embodiments, $R^1$ is a substituted alkenyl. In certain embodiments, the compound is of one of the following formulae:

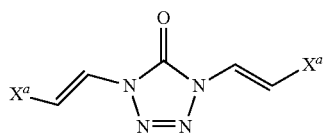

wherein each $X^a$ is as described above, or a salt or stereoisomer thereof. In certain embodiments, the compound is a symmetrical dimer and each $X^a$ is the same. In some instances, the compound is an unsymmetrical dimer where each $X^a$ is different.

In certain embodiments of the compounds according to formula (Ia) or (Ib), $R^1$ is derived from an amino acid. In some cases, $R^1$ can have the formula:

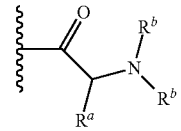

wherein $R^a$ is an amino acid side chain, e.g., —H for glycine, —$CH_3$ for alanine, and each $R^b$ is independently selected from H, $C_{1-6}$ alkyl, and —$C(O)C_{1-6}$ alkyl. For example, such compounds can have one of the following formulae:

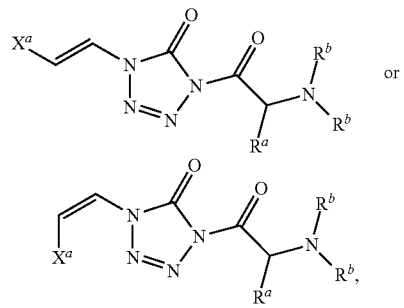

wherein $R^a$ is an amino acid side chain, e.g., —H for glycine, —$CH_3$ for alanine, and each $R^b$ is independently selected from H, $C_{1-6}$ alkyl, and —$C(O)C_{1-6}$ alkyl. Other examples of $R^1$ groups derived from amino acids include compounds of one of the following formulae:

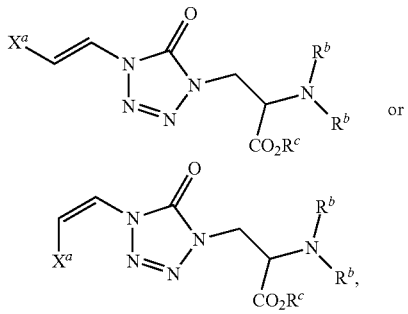

derived from serine, wherein each $R^b$ is independently selected from H, $C_{1-6}$ alkyl, and —$C(O)C_{1-6}$ alkyl and $R^c$ is selected from H and $C_{1-6}$ alkyl.

In certain embodiments of the compounds according to formula (Ia) or (Ib), $R^1$ can have the formula:

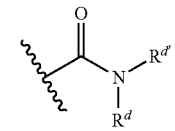

wherein $R^d$ and $R^{d'}$ are independently selected from H and $C_{1-6}$ alkyl.

An amino acid side chain includes side chains commonly found in naturally occurring amino acids (e.g., Ala or A, Cys or C, Asp or D, Glu or E, Phe or F, Gly or G, His or H, Ile or I, Lys or K, Leu or L, Met or M, Asn or N, Pro or P, Gln or Q, Arg or R, Ser or S, Thr or T, Val or V, Trp or W, Tyr or Y). Amino acid side chains may also include side chain found in amino acid analogs or unnatural amino acids. The terms "amino acid analog," "unnatural amino acid," and the like may be used interchangeably, and include amino acid-like compounds that are similar in structure and/or overall shape to one or more amino acids commonly found in naturally occurring proteins. Amino acid analogs also include natural amino acids with modified side chains or backbones. Amino acid analogs also include amino acid analogs with the same stereochemistry as in the naturally occurring D-form, as well as the L-form of amino acid analogs.

In certain embodiments, $R^1$ is alkyl, such as $C_{1-6}$ alkyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is pentyl. In certain embodiments, $R^1$ is hexyl. The $C_{1-6}$ alkyl may be unbranched or branched. For example, $R^1$ may be propyl, such as n-propyl or iso-propyl. For example, $R^1$ may be butyl, such as n-butyl, sec-butyl (1-methylpropyl), iso-butyl (2-methylpropyl) or tert-butyl (1,1-dimethylethyl).

In certain embodiments, $R^1$ is substituted alkyl, such as substituted $C_{1-6}$ alkyl. In certain embodiments, $R^1$ is substituted methyl. In certain embodiments, $R^1$ is substituted ethyl. In certain embodiments, $R^1$ is substituted propyl. In certain embodiments, $R^1$ is substituted butyl. In certain embodiments, $R^1$ is substituted pentyl. In certain embodiments, $R^1$ is substituted hexyl. Substituents on $R^1$ include, but are not limited to, halogen, alkyl, substituted alkyl, alkenyl, substituted alkenyl, alkynyl, substituted alkynyl, alkoxy, substituted alkoxy, hydroxyl, carboxyl, carboxyl ester, amino, substituted amino, acyl, aminoacyl, acylamino, thioalkoxy, sulfonyl, aminosulfonyl, sulfonylamino, cycloalkyl, substituted cycloalkyl, heterocyclyl, substituted heterocyclyl, aryl, substituted aryl, heteroaryl, and substituted heteroaryl. For example, $R^1$ may be a substituted alkyl (e.g., substituted $C_{1-6}$ alkyl), substituted by a hydroxyl. In some instances, $R^1$ is a substituted alkyl (e.g., substituted $C_{1-6}$ alkyl), substituted by alkoxy or substituted alkoxy, such as a $C_{1-6}$ alkoxy or a $C_{1-6}$ substituted alkoxy. In some instances, $R^1$ is a substituted alkyl (e.g., substituted $C_{1-6}$ alkyl), substituted by amino or substituted amino. In some instances, $R^1$ is a substituted alkyl (e.g., substituted $C_{1-6}$ alkyl), substituted by carboxyl or carboxyl ester. In some instances, $R^1$ is a substituted alkyl (e.g., substituted $C_{1-6}$ alkyl), substituted by aminoacyl or acylamino. In some instances, $R^1$ is a substituted alkyl (e.g., substituted $C_{1-6}$ alkyl), substituted by thioalkoxy or sulfonyl. In some instances, $R^1$ is a substituted alkyl (e.g., substituted $C_{1-6}$ alkyl), substituted by cycloalkyl or substituted cycloalkyl, such as, for example, $C_{3-8}$ cycloalkyl or $C_{3-8}$ substituted cycloalkyl, or $C_{3-6}$ cycloalkyl or $C_{3-6}$ substituted cycloalkyl, or $C_{3-5}$ cycloalkyl or $C_{3-5}$ substituted cycloalkyl, or $C_{3-4}$ cycloalkyl or $C_{3-4}$ substituted cycloalkyl. In some instances, $R^1$ is a substituted alkyl (e.g., substituted $C_{1-6}$ alkyl), substituted by heterocyclyl or substituted heterocyclyl, such as, for example, $C_{3-8}$ heterocyclyl or $C_{3-8}$ substituted heterocyclyl, or $C_{3-6}$ heterocyclyl or $C_{3-6}$ substituted heterocyclyl, or $C_{3-5}$ heterocyclyl or $C_{3-5}$ substituted heterocyclyl, or $C_{3-4}$ heterocyclyl or $C_{3-4}$ substituted heterocyclyl. In some instances, $R^1$ is a substituted alkyl (e.g., substituted $C_{1-6}$ alkyl), substituted by aryl or substituted aryl, such as, for example, $C_{3-6}$ aryl or $C_{3-6}$ substituted aryl, such as phenyl or substituted phenyl. In some instances, $R^1$ is a substituted alkyl (e.g., substituted $C_{1-6}$ alkyl), substituted by heteroaryl or substituted heteroaryl, such as, for example, $C_{3-6}$ heteroaryl or $C_{3-6}$ substituted heteroaryl. Combinations of the above substituents on $R^1$ are also included. Any of the $R^1$ groups described herein may be included in the compounds of formulae (Ia) or (Ib).

For example, in certain embodiments, $R^1$ is alkyl, substituted alkyl, cycloalkyl, substituted cycloalkyl, heterocyclyl, substituted heterocyclyl, aryl, substituted aryl, heteroaryl, or substituted heteroaryl, such that the compound of formula (Ia) has a structure selected from the following:

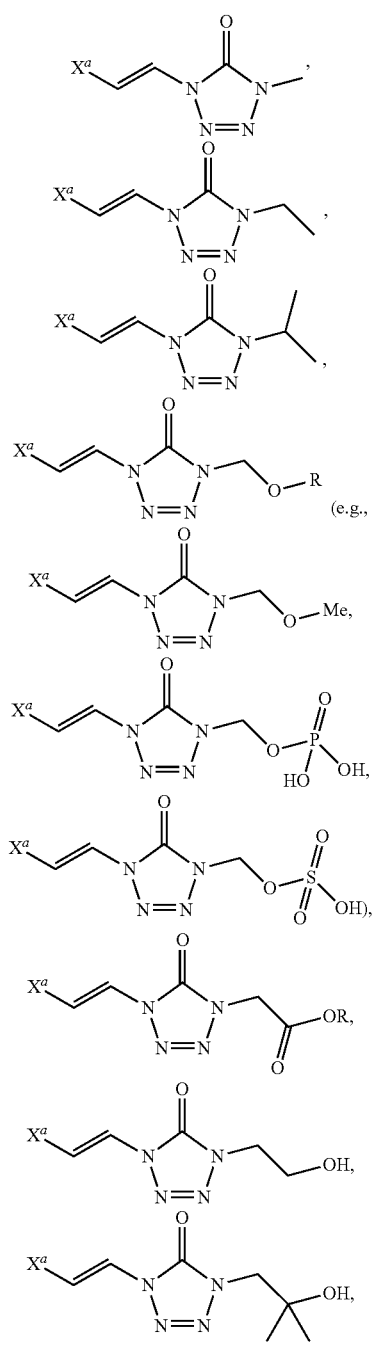

-continued

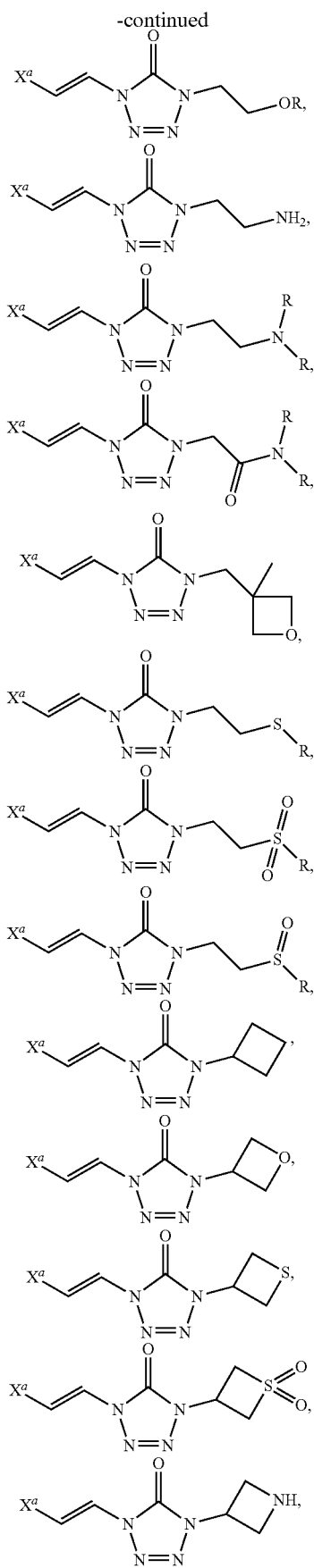

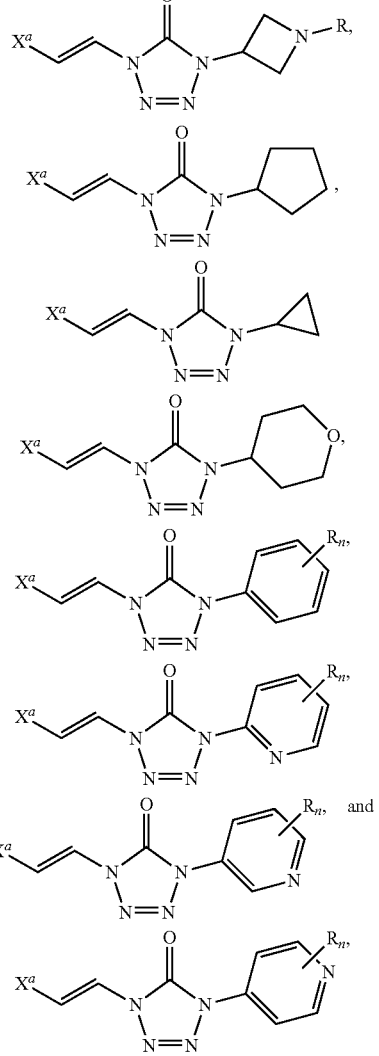

wherein

X$^a$ is as described above;

each R is independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, sulfoxy and phosphate; and n is 0, 1, 2, 3, 4 or 5;

or a salt or stereoisomer thereof.

For example, in certain embodiments, R$^1$ is alkyl, substituted alkyl, cycloalkyl, substituted cycloalkyl, heterocyclyl, substituted heterocyclyl, aryl, substituted aryl, heteroaryl, or substituted heteroaryl, such that the compound of formula (Ia) has a structure selected from the following:

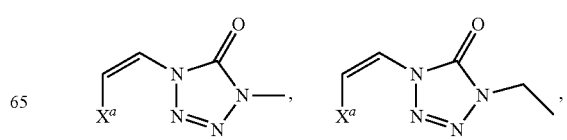

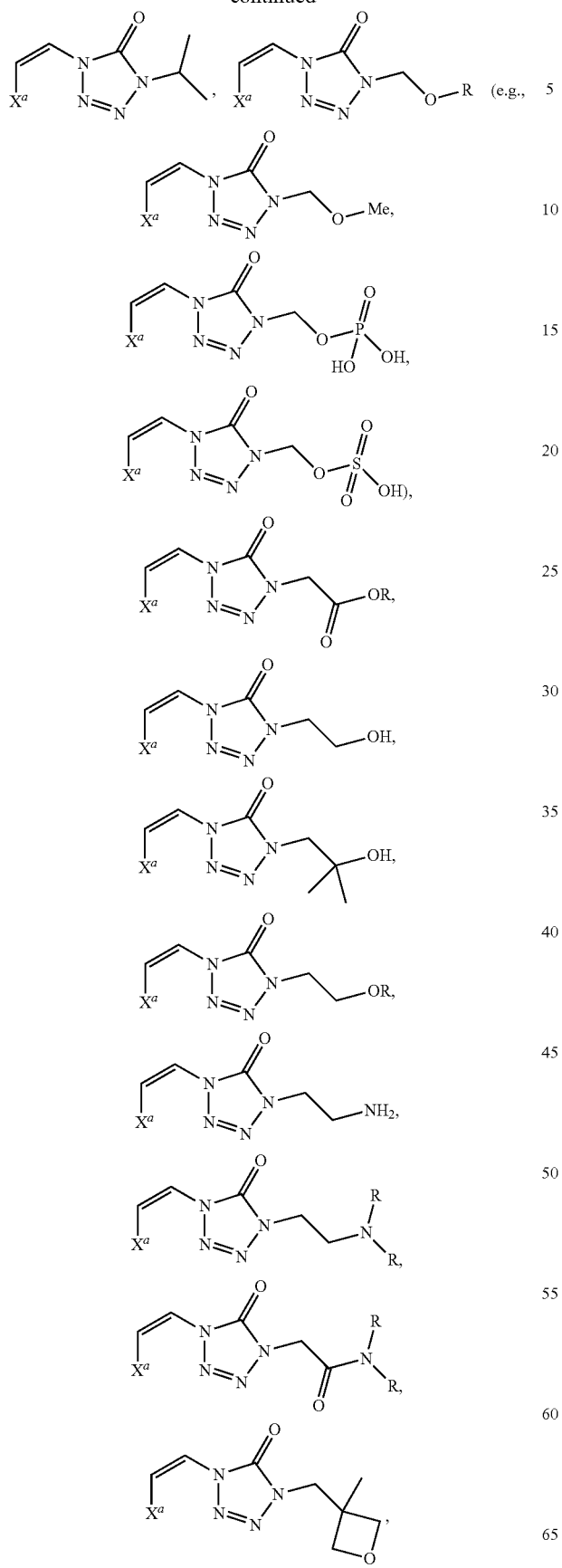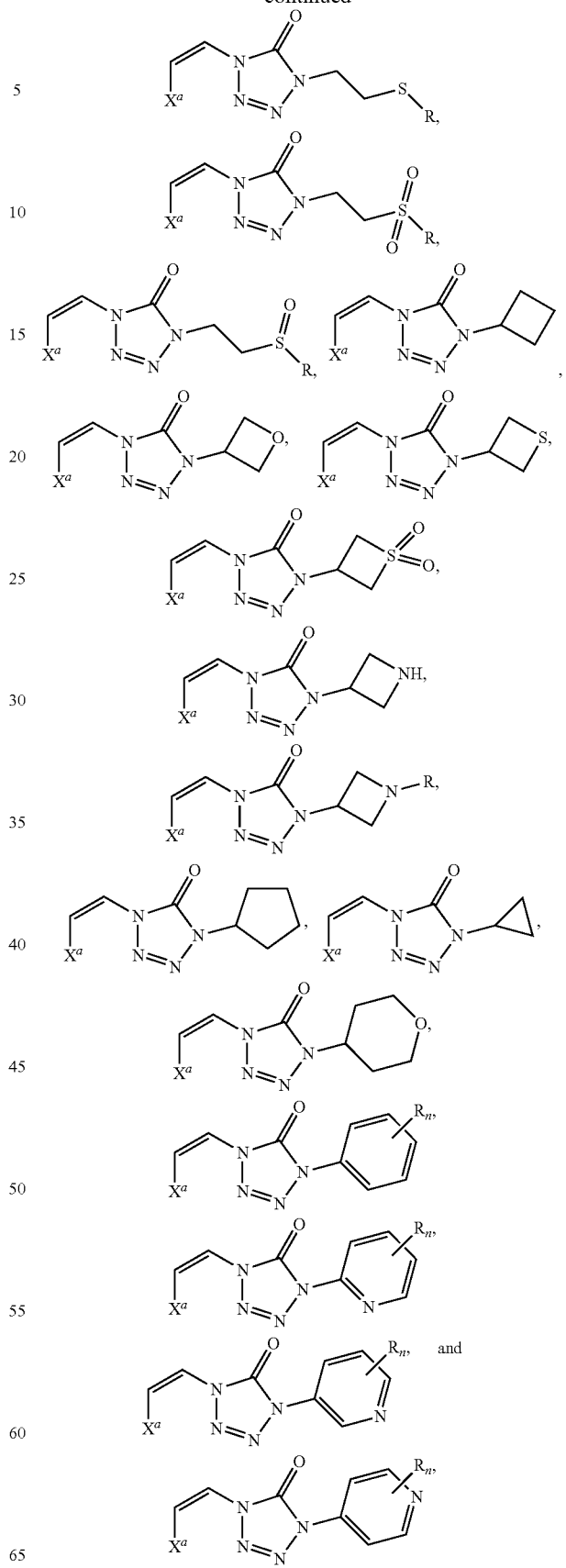

wherein

X$^a$ is as described above;

each R is independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, sulfoxy and phosphate; and n is 0, 1, 2, 3, 4 or 5;

or a salt or stereoisomer thereof.

In certain embodiments, each R is independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, R is hydrogen. In certain embodiments, R is alkyl or substituted alkyl, such as $C_{1-6}$ alkyl (e.g., methyl, ethyl, propyl, butyl, pentyl, or hexyl) or $C_{1-6}$ substituted alkyl. In certain embodiments, R is alkenyl or substituted alkenyl. In certain embodiments, R is alkynyl or substituted alkynyl. In certain embodiments, R is cycloalkyl or substituted cycloalkyl, such as $C_{3-8}$ cycloalkyl or $C_{3-8}$ substituted cycloalkyl, or $C_{3-6}$ cycloalkyl or $C_{3-6}$ substituted cycloalkyl, or $C_{3-5}$ cycloalkyl or $C_{3-5}$ substituted cycloalkyl. In certain embodiments, R is heterocyclyl or substituted heterocyclyl, such as $C_{3-8}$ heterocyclyl or $C_{3-8}$ substituted heterocyclyl, or $C_{3-6}$ heterocyclyl or $C_{3-6}$ substituted heterocyclyl, or $C_{3-5}$ heterocyclyl or $C_{3-5}$ substituted heterocyclyl. In certain embodiments, R is aryl or substituted aryl, such as $C_{3-8}$ aryl or $C_{3-8}$ substituted aryl, or $C_{3-6}$ aryl or $C_{3-6}$ substituted aryl (e.g., phenyl or substituted phenyl). In certain embodiments, R is heteroaryl or substituted heteroaryl, such as $C_{3-8}$ heteroaryl or $C_{3-8}$ substituted heteroaryl, or $C_{3-6}$ heteroaryl or $C_{3-6}$ substituted heteroaryl. In particular embodiments, R is —P(O)(OH)$_2$ or a salt thereof, and in other embodiments, R is —S(O)$_2$OH or a salt thereof.

In some embodiments, the compound is a dimer. In these embodiments, R$^1$ is R$^5$, where R$^{15}$ includes a linking group and a second compound of formula (Ia) or (Ib). By "linking group" is meant a moiety that connects two or more moieties together through one or more covalent bonds and atoms. In certain embodiments, the linking group is an alkyl linking group, such as a $C_{1-10}$ alkyl linking group, or a $C_{1-8}$ alkyl linking group, or a $C_{1-6}$ alkyl linking group, or a $C_{1-3}$ alkyl linking group. In certain embodiments, the linking group attaches a first compound of formula (Ia) or (Ib) to a second compound of formula (Ia) or (Ib). In some instances, the first compound of formula (Ia) or (Ib) has one end of the linking group attached at the R$^1$ position, and the other end of the linking group is attached at the R$^1$ position of the second compound of formula (Ia) or (Ib). In these embodiments, the two compounds of formulae (Ia) and/or (Ib) in the dimer are connected to each other at their respective R$^1$ positions through the linking group.

In certain embodiments, the linking group is has the structure: —(CH$_2$)$_n$—Z$_y$—(CH$_2$)$_m$—, wherein n is an integer from 1 to 6;

m is 0 or an integer from 1 to 6;

y is 0 or 1; and

Z is O, NH, —O—P(O)(OH)—O—, S, S(O), SO$_2$ or —O—S(O)$_2$—O—.

In certain embodiments, n is an integer from 1 to 6, such as 1, 2, 3, 4, 5 or 6.

In certain embodiments, m is 0 or an integer from 1 to 6. In certain embodiments, m is 0, and thus the —(CH$_2$)$_m$— portion of the linking group is not present. In certain embodiments, m is an integer from 1 to 6, such as 1, 2, 3, 4, 5 or 6.

In certain embodiments, y is 0 or 1. In certain embodiments, y is 0, and thus Z is not present. In certain embodiments, y is 1, and thus Z is present.

In certain embodiments, Z is O, NH, —O—P(O)(OH)—O—, S, S(O), SO$_2$ or —O—S(O)$_2$—O—. In certain embodiments, Z is O. In certain embodiments, Z is NH. In certain embodiments, Z is —O—P(O)(OH)—O—. In certain embodiments, Z is S. In certain embodiments, Z is S(O). In certain embodiments, Z is SO$_2$. In certain embodiments, Z is —O—S(O)$_2$—O—.

In certain embodiments, n is 1, m is 0 and y is 0. In certain embodiments, n is 2, m is 0 and y is 0. In certain embodiments, n is 3, m is 0 and y is 0. In certain embodiments, n is 4, m is 0 and y is 0. In certain embodiments, n is 5, m is 0 and y is 0. In certain embodiments, n is 6, m is 0 and y is 0.

In certain embodiments, n is 1, m is 1, y is 1 and Z is O. In certain embodiments, n is 2, m is 2, y is 1 and Z is O. In certain embodiments, n is 1, m is 1, y is 1 and Z is NH. In certain embodiments, n is 2, m is 2, y is 1 and Z is NH. In certain embodiments, n is 1, m is 1, y is 1 and Z is —O—P(O)(OH)—O—. In certain embodiments, n is 2, m is 2, y is 1 and Z is —O—P(O)(OH)—O—. In certain embodiments, n is 1, m is 1, y is 1 and Z is S. In certain embodiments, n is 2, m is 2, y is 1 and Z is S. In certain embodiments, n is 1, m is 1, y is 1 and Z is S(O). In certain embodiments, n is 2, m is 2, y is 1 and Z is S(O). In certain embodiments, n is 1, m is 1, y is 1 and Z is SO$_2$. In certain embodiments, n is 2, m is 2, y is 1 and Z is SO$_2$. In certain embodiments, n is 1, m is 1, y is 1 and Z is —O—S(O)$_2$—O—. In certain embodiments, n is 2, m is 2, y is 1 and Z is —O—S(O)$_2$—O—.

In certain embodiments, n is 1, m is 1, and y is 1. As such, in certain embodiments, the compound has the formula:

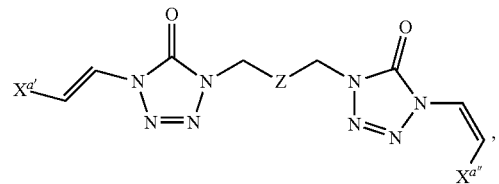

wherein

X$^{a'}$ and X$^{a''}$ are each independently X$^a$; and

Z is O, NH, —O—P(O)(OH)—O—, S, S(O), SO$_2$ or —O—S(O)$_2$—O—, or a salt or stereoisomer thereof.

In certain embodiments, n is 1, m is 1, and y is 1. As such, in certain embodiments, the compound has the formula:

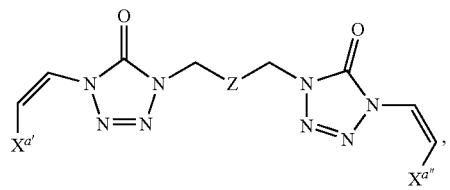

wherein

X$^{a'}$ and X$^{a''}$ are each independently X$^a$; and

Z is O, NH, —O—P(O)(OH)—O—, S, S(O), SO$_2$ or —O—S(O)$_2$—O—, or a salt or stereoisomer thereof.

In certain embodiments, n is 1, m is 1, and y is 1. As such, in certain embodiments, the compound has the formula:

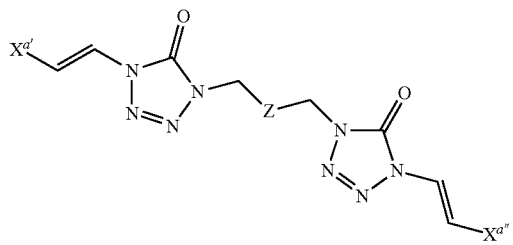

wherein
$X^{a'}$ and $X^{a'''}$ are each independently $X^a$; and
Z is O, NH, —O—P(O)(OH)—O—, S, S(O), $SO_2$ or —O—S(O)$_2$—O—,
or a salt or stereoisomer thereof.

In certain embodiments, n is 2, m is 2, and y is 1. As such, in certain embodiments, the compound has the formula:

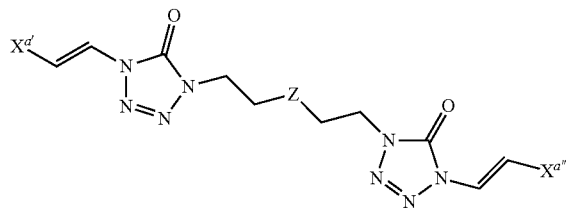

wherein
$X^{a'}$ and $X^{a''}$ are each independently $X^a$; and
Z is O, NH, —O—P(O)(OH)—O—, S, S(O), $SO_2$ or —O—S(O)$_2$—O—,
or a salt or stereoisomer thereof.

In certain embodiments, the compound has the formula:

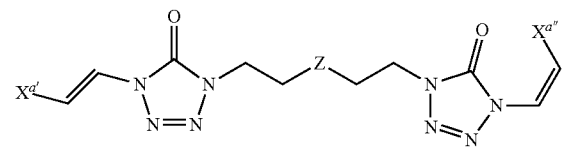

wherein
$X^{a'}$ and $X^{a''}$ are each independently $X^a$; and
Z is O, NH, —O—P(O)(OH)—O—, S, S(O), $SO_2$ or —O—S(O)$_2$—O—,
or a salt or stereoisomer thereof.

In certain embodiments, the compound has the formula:

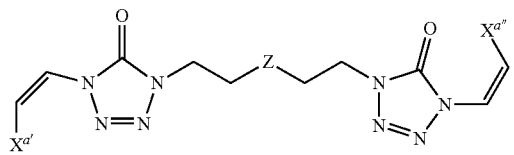

wherein
$X^{a'}$ and $X^{a''}$ are each independently $X^a$; and
Z is O, NH, —O—P(O)(OH)—O—, S, S(O), $SO_2$ or —O—S(O)$_2$—O—,
or a salt or stereoisomer thereof.

In certain embodiments, $X^{a'}$ and $X^{a''}$ are each independently $X^a$ as described above. In certain embodiments, $X^{a'}$ and $X^{a''}$ are the same. In certain embodiments, $X^{a'}$ and $X^{a''}$ are different. For example, $X^{a'}$ and $X^{a''}$ may each be independently selected from carboxyl ester, heterocyclyl, substituted heterocyclyl, heteroaryl and substituted heteroaryl. In certain embodiments, $X^{a'}$ is a carboxyl ester. In certain embodiments, $X^{a'}$ is heterocyclyl or substituted heterocyclyl. In certain embodiments, $X^{a'}$ is heteroaryl or substituted heteroaryl. In certain embodiments, $X^{a''}$ is a carboxyl ester. In certain embodiments, $X^{a''}$ is heterocyclyl or substituted heterocyclyl. In certain embodiments, $X^{a''}$ is heteroaryl or substituted heteroaryl.

In certain embodiments, $X^{a'}$ is a heterocyclyl or a heteroaryl as described above. In certain embodiments, the heterocyclyl or heteroaryl is substituted with one or more substituents. For example, in certain embodiments, the substituent on $X^{a'}$ may be $X^1$, such as a $C_{1-6}$ alkyl or a progroup as described in more detail below regarding compounds of formulae (IIa) and (IIb).

In certain embodiments, $X^{a''}$ is a heterocyclyl or a heteroaryl as described above. In certain embodiments, the heterocyclyl or heteroaryl is substituted with one or more substituents. For example, in certain embodiments, the substituent on $X^{a''}$ may be $X^1$, such as a $C_{1-6}$ alkyl or a progroup as described in more detail below regarding compounds of formulae (IIa) and (IIb).

In certain embodiments, Z is O, —O—P(O)(OH)—O—, NH, S, S(O), $SO_2$ or —O—S(O)$_2$—O—. In certain embodiments, Z is O. In certain embodiments, Z is NH. In certain embodiments, Z is —O—P(O)(OH)—O—. In certain embodiments, Z is S. In certain embodiments, Z is S(O). In certain embodiments, Z is $SO_2$. In certain embodiments, Z is —O—S(O)$_2$—O—.

In certain embodiments, the compound of formula (Ia) is a dimer selected from the following compounds:

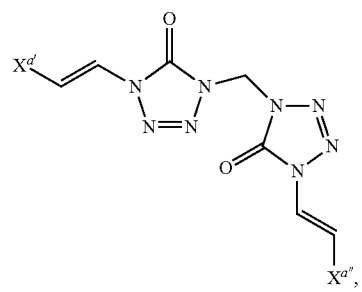

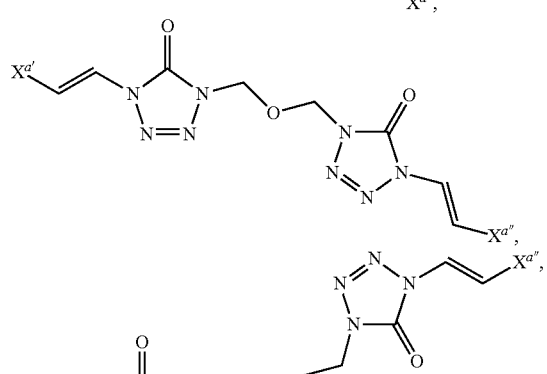

-continued

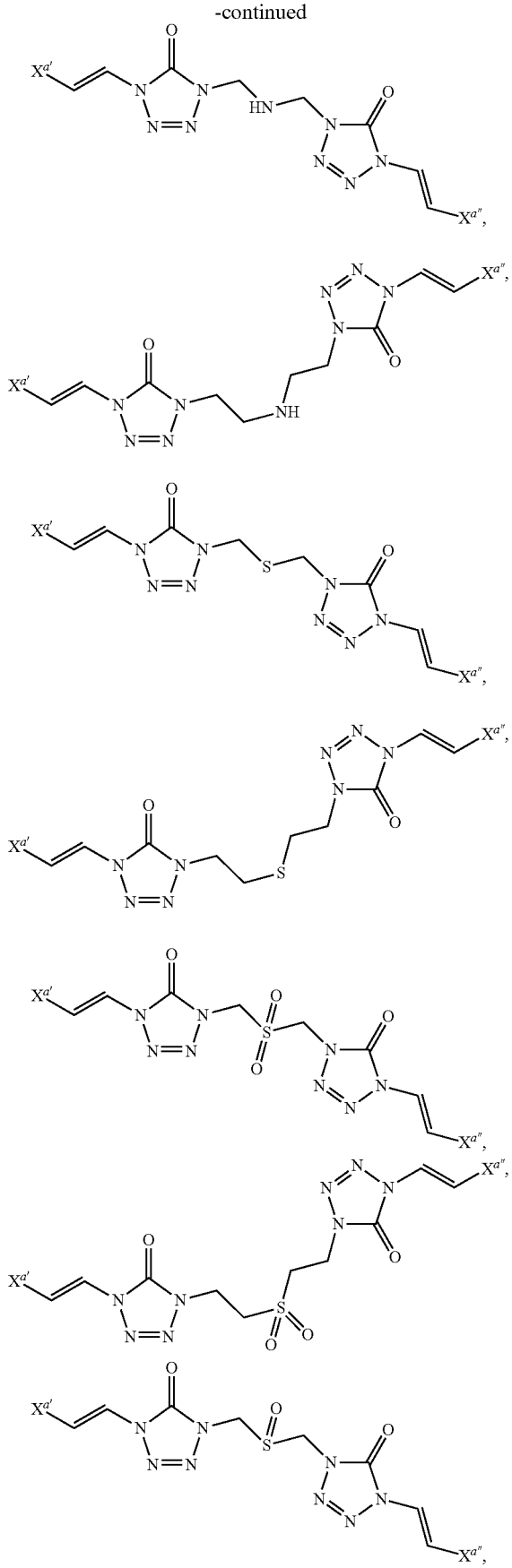

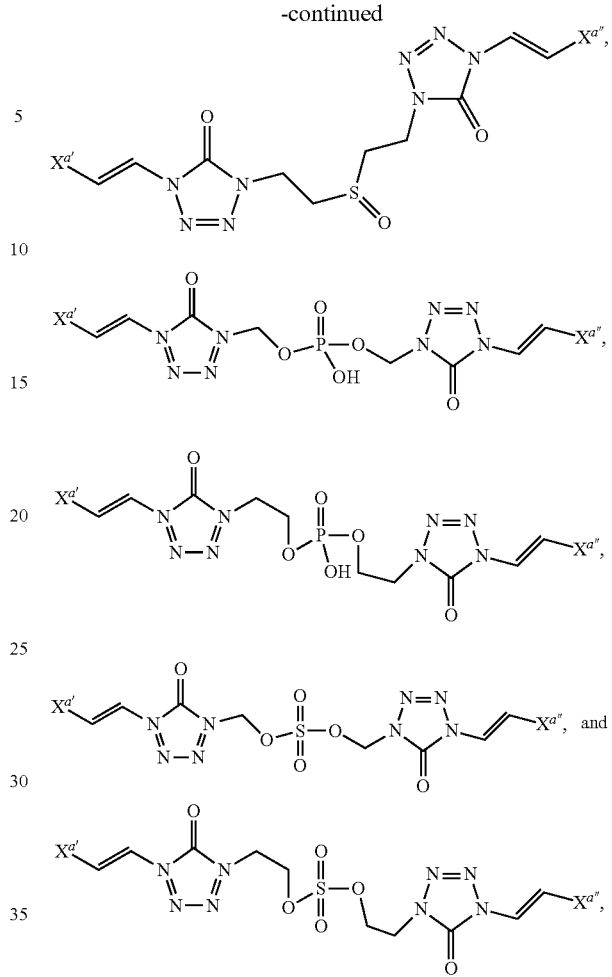

wherein $X^{a'}$ and $X^{a'}$ are as described above, or a salt or stereoisomer thereof.

In certain embodiments where the compound is a dimer, the compound may be a dimer prodrug. In these embodiments, the linking group connecting the two compounds of formula (Ia) and/or (Ib) in the dimer may be a cleavable linking group. By "cleavable" is meant that one or more covalent bonds in the linking group may be broken. In some instances, cleavage of the linking group in the dimer releases the active agent moieties (e.g., two pharmaceutically active compounds). For example, a cleavable linking group may be cleaved by hydrolysis of one or more bonds in the linking group that connect the first compound of formula I to the second compound of formula I in the dimer. In some embodiments, cleavage of the cleavable linking group may occur in vivo, for instance in the gastrointestinal tract (e.g., stomach, small intestine, large intestine, etc.), or a desired site of action of the compound. In certain cases, compounds that include a cleavable linking group may facilitate delivery of the pharmaceutically active forms of the compound at a desired site of action, or after a desired amount of time after administration of the dimer (e.g., delayed release formulations, controlled release formulations, and the like).

Formula B

In certain embodiments, the compound is a compound of formula (B):

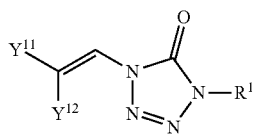

(B)

wherein either $Y^{11}$ is —C(=O)—O—$X^1$ and $Y^{12}$ is hydrogen, or $Y^{12}$ is —C(=O)—O—$X^1$ and $Y^{11}$ is hydrogen;

$R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$, wherein $R^{15}$ comprises a linking group and a compound of formula (B); and $X^1$ is a H, $C_{1-6}$ alkyl or a progroup;

or a salt or stereoisomer thereof.

Formula (IIa) and (IIb)

In certain embodiments of formula (B), the compound is a compound of formula (IIa) or (IIb):

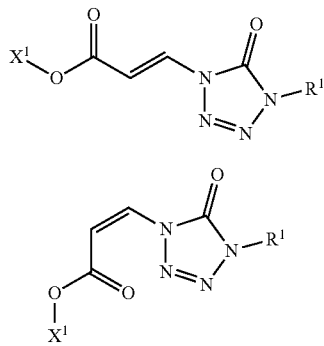

wherein $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (IIa) or (IIb); and $X^1$ is hydrogen, $C_{1-6}$ alkyl or a progroup;

or a salt or stereoisomer thereof.

In some embodiments of formula (IIa) and (IIb), the compound is a dimer, where $R^{15}$ includes a linking group and a compound of formula (IIa) or (IIb). In certain embodiments, the compound is a symmetrical dimer. In certain embodiments, the compound is an unsymmetrical dimer. In some instances, $R^{15}$ includes a linking group and a compound of formula (IIa). In some instances, $R^{15}$ includes a linking group and a compound of formula (IIb).

In certain embodiments, the compound of formula (Ia) is a compound of formula (IIa):

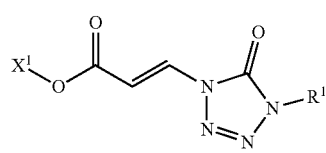

(IIa)

wherein $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$ wherein $R^{15}$ includes a linking group and a compound of formula (IIa); and $X^1$ is a H, $C_{1-6}$ alkyl or a progroup;

or a salt or stereoisomer thereof.

In certain embodiments, the compound of formula (Ib) is a compound of formula (IIb):

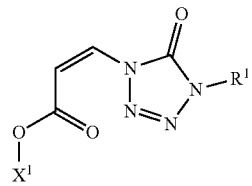

(IIb)

wherein $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$ wherein $R^{15}$ includes a linking group and a compound of formula (IIb); and $X^1$ is a H, $C_{1-6}$ alkyl or a progroup;

or a salt or stereoisomer thereof.

In certain embodiments, $R^1$ is as described above regarding compounds of formulae (Ia) and (Ib). For example, in certain embodiments, $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$R^{15}$ (e.g., as described herein).

In certain embodiments, $R^1$ is hydrogen. In certain embodiments, $R^1$ is alkyl or substituted alkyl. In certain embodiments, $R^1$ is alkenyl or substituted alkenyl. In certain embodiments, $R^1$ is alkynyl or substituted alkynyl. In certain embodiments, $R^1$ is cycloalkyl or substituted cycloalkyl. In certain embodiments, $R^1$ is cyclohexyl or substituted cyclohexyl. In certain embodiments, $R^1$ is cyclopentyl or substituted cyclopentyl. In certain embodiments, $R^1$ is cyclobutyl or substituted cyclobutyl. In certain embodiments, $R^1$ is cyclopropyl or substituted cyclopropyl. In certain embodiments, $R^1$ is heterocyclyl or substituted heterocyclyl. In certain embodiments, $R^1$ is 4-tetrahydropyranyl or substituted 4-tetrahydropyranyl. In certain embodiments, $R^1$ is aryl or substituted aryl. In certain embodiments, $R^1$ is phenyl or substituted phenyl. In certain embodiments, $R^1$ is heteroaryl or substituted heteroaryl. In certain embodiments, $R^1$ is pyridyl or substituted pyridyl. In certain embodiments, $R^1$ is a 2-pyridyl, a 3-pyridyl or 4-pyridyl. In certain embodiments, $R^1$ is a substituted 2-pyridyl, a substituted 3-pyridyl or a substituted 4-pyridyl.

In certain embodiments of any of formulae (Ia), (Ib), (IIa) or (IIb), $R^1$ is a substituted alkenyl. In certain embodiments, $R^1$ is:

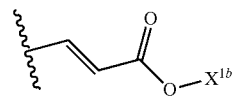

wherein $X^{1b}$ is selected from $C_{1-6}$ alkyl and a progroup.

In certain embodiments, the compound has the formula:

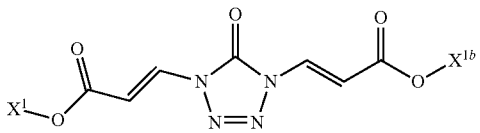

wherein $X^1$ and $X^{1b}$ are independently hydrogen, $C_{1-6}$ alkyl or a progroup; or a salt or stereoisomer thereof.

In certain embodiments, the compound has the formula:

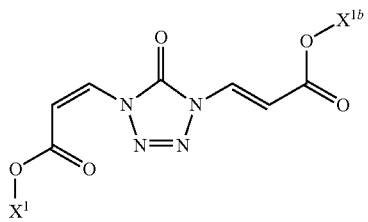

wherein $X^1$ and $X^{1b}$ are independently hydrogen, $C_{1-6}$ alkyl or a progroup; or a salt or stereoisomer thereof.

In certain embodiments, the compound has the formula:

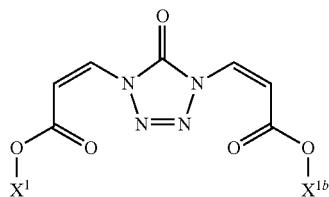

wherein $X^1$ and $X^{1b}$ are independently hydrogen, $C_{1-6}$ alkyl or a progroup; or a salt or stereoisomer thereof.

In certain embodiments, the compound is a symmetrical dimer and $X^1$ and $X^{1b}$ are the same. In some instances, the compound is an unsymmetrical dimer where $X^1$ and $X^{1b}$ are different. In some instances, $X^1$ and $X^{1b}$ are independently a $C_{1-6}$ alkyl. In some instances, $X^1$ and $X^{1b}$ are independently an alkyl or a substituted alkyl. In certain instances, the compound has the structure:

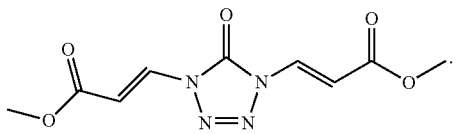

In certain embodiments, R is alkyl, such as $C_{1-6}$ alkyl. In certain embodiments, $R^1$ is methyl. In certain embodiments, $R^1$ is ethyl. In certain embodiments, $R^1$ is propyl. In certain embodiments, $R^1$ is butyl. In certain embodiments, $R^1$ is pentyl. In certain embodiments, $R^1$ is hexyl. The $C_{1-6}$ alkyl may be unbranched or branched. For example, $R^1$ may be propyl, such as n-propyl or iso-propyl. For example, $R^1$ may be butyl, such as n-butyl, sec-butyl (1-methylpropyl), isobutyl (2-methylpropyl) or tert-butyl (1,1-dimethylethyl).

In certain embodiments, $R^1$ is substituted alkyl, such as substituted $C_{1-6}$ alkyl. In certain embodiments, $R^1$ is substituted methyl. In certain embodiments, $R^1$ is substituted ethyl. In certain embodiments, $R^1$ is substituted propyl. In certain embodiments, $R^1$ is substituted butyl. In certain embodiments, $R^1$ is substituted pentyl. In certain embodiments, $R^1$ is substituted hexyl. Substituents on $R^1$ include, but are not limited to, halogen, alkyl, substituted alkyl, alkenyl, substituted alkenyl, alkynyl, substituted alkynyl, alkoxy, substituted alkoxy, hydroxyl, carboxyl, carboxyl ester, amino, substituted amino, acyl, aminoacyl, acylamino, thioalkoxy, sulfonyl, aminosulfonyl, sulfonylamino, cycloalkyl, substituted cycloalkyl, heterocyclyl, substituted heterocyclyl, aryl, substituted aryl, heteroaryl, and substituted heteroaryl. For example, $R^1$ may be a substituted alkyl (e.g., substituted $C_{1-6}$ alkyl), substituted by a hydroxyl. In some instances, $R^1$ is a substituted alkyl (e.g., substituted $C_{1-6}$ alkyl), substituted by alkoxy or substituted alkoxy, such as a $C_{1-6}$ alkoxy or a $C_{1-6}$ substituted alkoxy. In some instances, $R^1$ is a substituted alkyl (e.g., substituted $C_{1-6}$ alkyl), substituted by amino or substituted amino. In some instances, $R^1$ is a substituted alkyl (e.g., substituted $C_{1-6}$ alkyl), substituted by carboxyl or carboxyl ester. In some instances, $R^1$ is a substituted alkyl (e.g., substituted $C_{1-6}$ alkyl), substituted by aminoacyl or acylamino (e.g., —CON(R)$_2$, wherein each R is independently hydrogen, a $C_{1-6}$ alkyl or a substituted $C_{1-6}$ alkyl). In some instances, $R^1$ is a substituted alkyl (e.g., substituted $C_{1-6}$ alkyl), substituted by thioalkoxy or sulfonyl. In some instances, $R^1$ is a substituted alkyl (e.g., substituted $C_{1-6}$ alkyl), substituted by cycloalkyl or substituted cycloalkyl, such as, for example, $C_{3-8}$ cycloalkyl or $C_{3-8}$ substituted cycloalkyl, or $C_{3-6}$ cycloalkyl or $C_{3-6}$ substituted cycloalkyl, or $C_{3-5}$ cycloalkyl or $C_{3-5}$ substituted cycloalkyl, or $C_{3-4}$ cycloalkyl or $C_{3-4}$ substituted cycloalkyl. In some instances, $R^1$ is a substituted alkyl (e.g., substituted $C_{1-6}$ alkyl), substituted by heterocyclyl or substituted heterocyclyl, such as, for example, $C_{3-8}$ heterocyclyl or $C_{3-8}$ substituted heterocyclyl, or $C_{3-6}$ heterocyclyl or $C_{3-6}$ substituted heterocyclyl, or $C_{3-5}$ heterocyclyl or $C_{3-5}$ substituted heterocyclyl, or $C_{3-4}$ heterocyclyl or $C_{3-4}$ substituted heterocyclyl. In some instances, $R^1$ is a substituted alkyl (e.g., substituted $C_{1-6}$ alkyl), substituted by aryl or substituted aryl, such as, for example, $C_{3-6}$ aryl or $C_{3-6}$ substituted aryl, such as phenyl or substituted phenyl. In some instances, $R^1$ is a substituted alkyl (e.g., substituted $C_{1-6}$ alkyl), substituted by heteroaryl or substituted heteroaryl, such as, for example, $C_{3-6}$ heteroaryl or $C_{3-6}$ substituted heteroaryl. Combinations of the above substituents on $R^1$ are also included.

For example, in certain embodiments, $R^1$ is alkyl, substituted alkyl, cycloalkyl, substituted cycloalkyl, heterocyclyl, substituted heterocyclyl, aryl, substituted aryl, heteroaryl, substituted heteroaryl, such that the compound of formula (IIa) has a structure selected from the following:

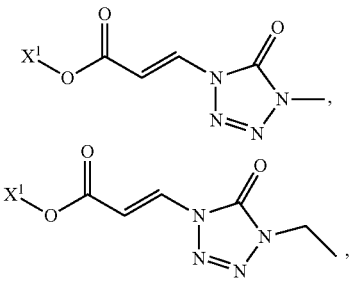

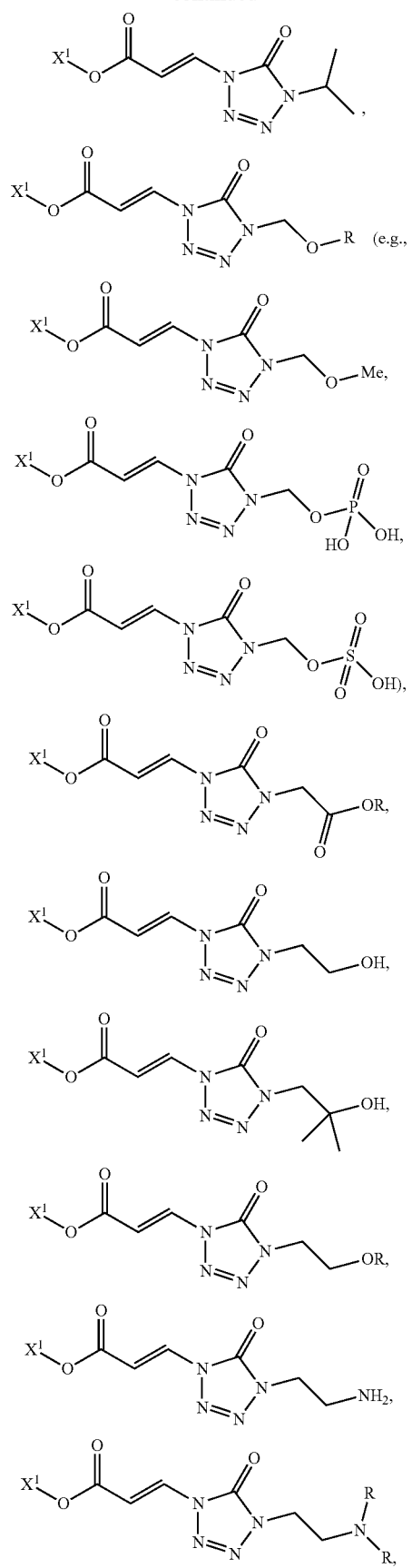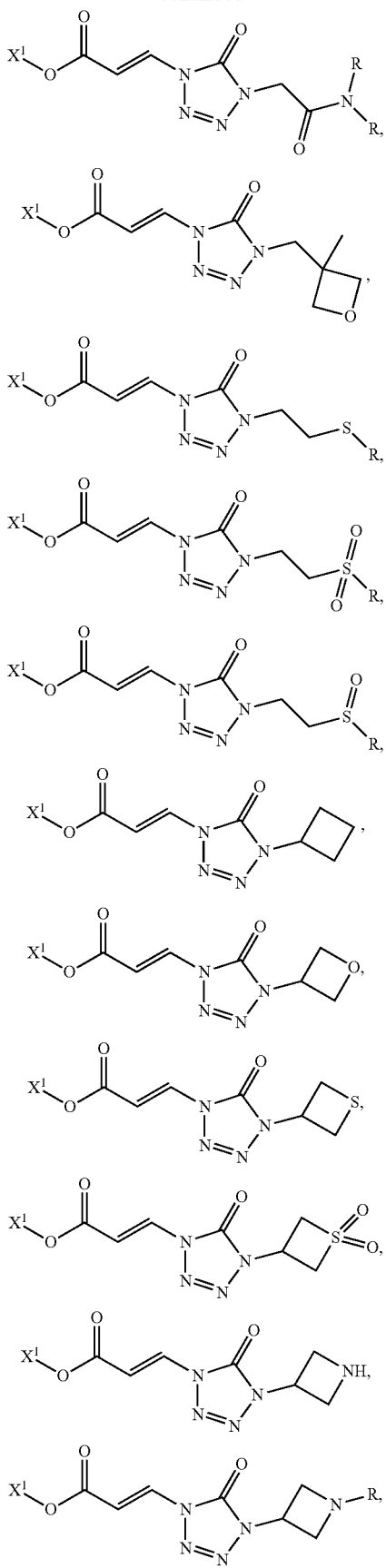

-continued

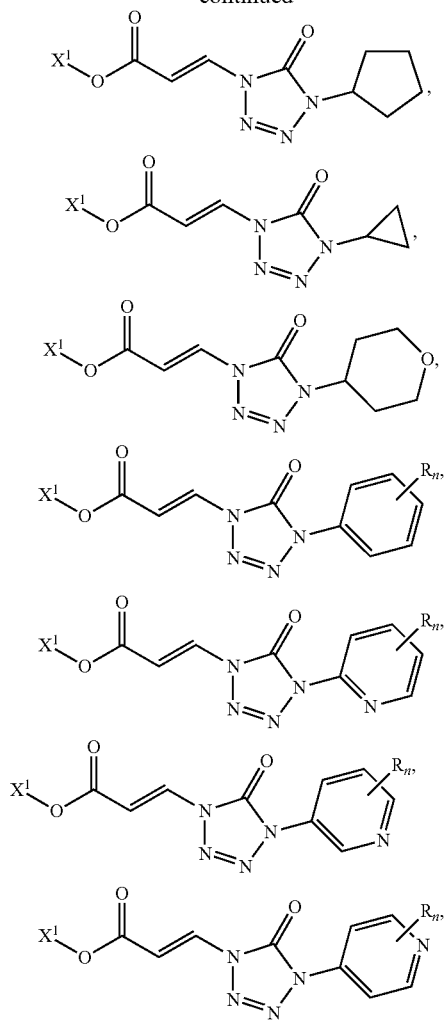

wherein

X¹ is as described below;

n is 0, 1, 2, 3, 4 or 5; and each R is independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, sulfoxy and phosphate, or a salt or stereoisomer thereof.

In certain embodiments, $R^1$ is alkyl, substituted alkyl, cycloalkyl, substituted cycloalkyl, heterocyclyl, substituted heterocyclyl, aryl, substituted aryl, heteroaryl, or substituted heteroaryl, such that the compound of formula (IIb) has a structure selected from the following:

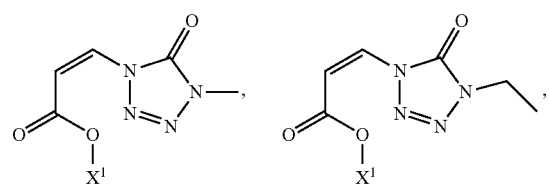

-continued

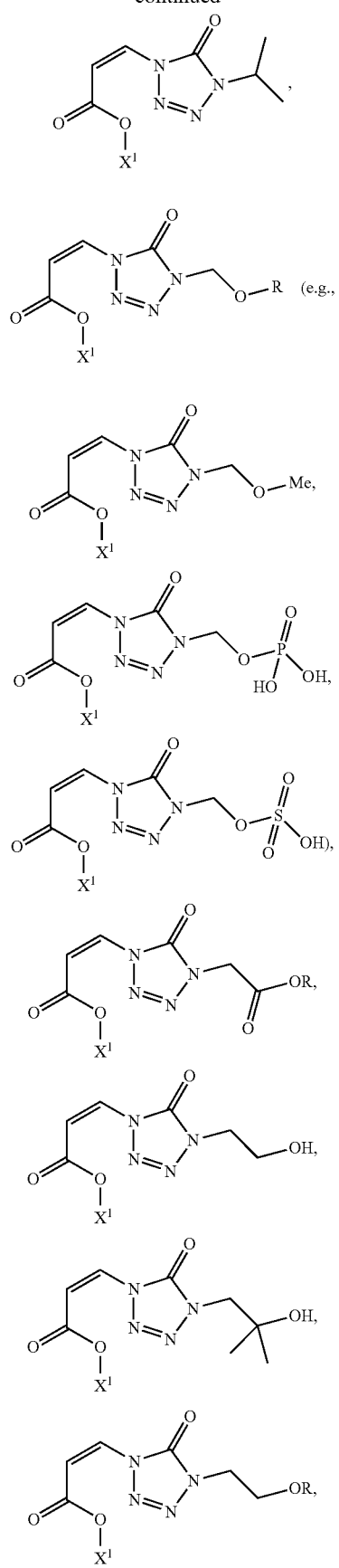

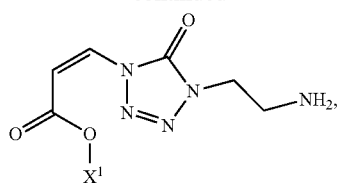
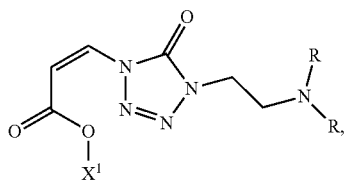
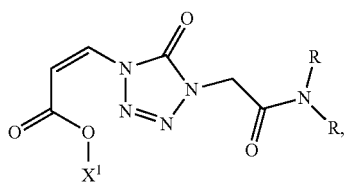
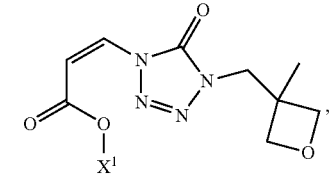
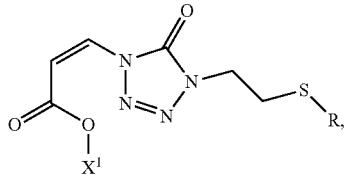
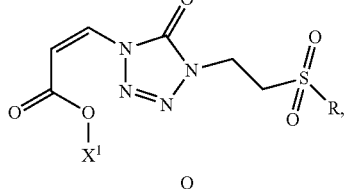
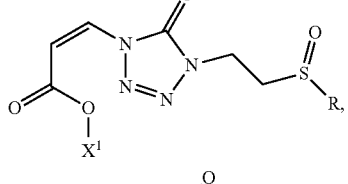
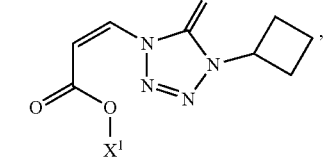
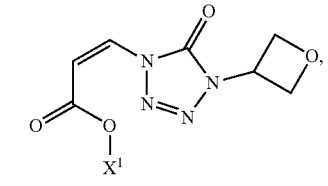
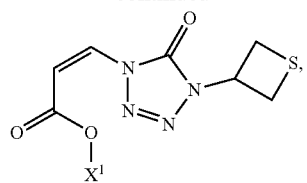
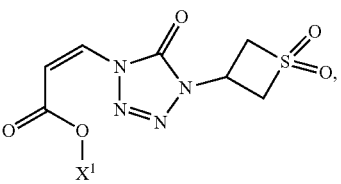
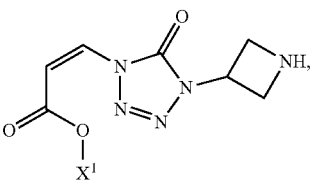
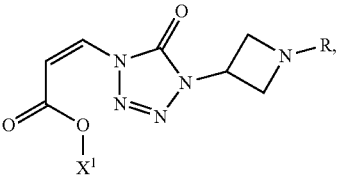
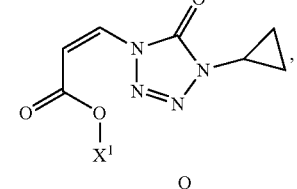
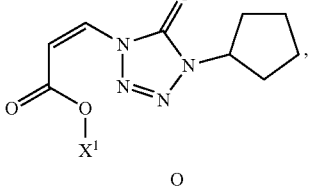
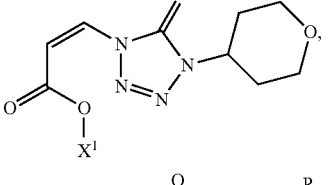
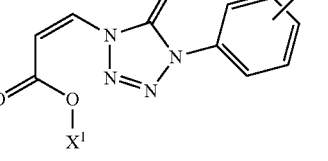
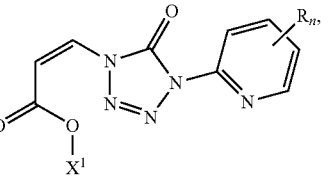

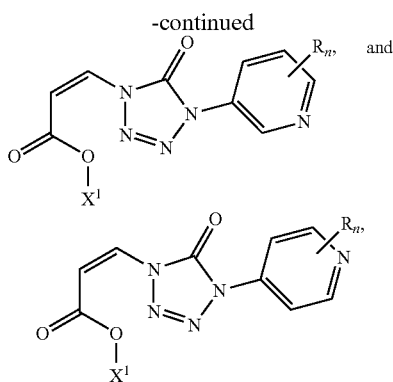

wherein
X¹ is as described below;
n is 0, 1, 2, 3, 4 or 5; and
each R is independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, sulfoxy and phosphate,
or a salt or stereoisomer thereof.

In certain embodiments, each R is independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, R is hydrogen. In certain embodiments, R is alkyl or substituted alkyl, such as $C_{1-6}$ alkyl (e.g., methyl, ethyl, propyl, butyl, pentyl, or hexyl) or $C_{1-6}$ substituted alkyl. In certain embodiments, R is alkenyl or substituted alkenyl. In certain embodiments, R is alkynyl or substituted alkynyl. In certain embodiments, R is cycloalkyl or substituted cycloalkyl, such as $C_{3-8}$ cycloalkyl or $C_{3-8}$ substituted cycloalkyl, or $C_{3-6}$ cycloalkyl or $C_{3-6}$ substituted cycloalkyl, or $C_{3-5}$ cycloalkyl or $C_{3-5}$ substituted cycloalkyl. In certain embodiments, R is heterocyclyl or substituted heterocyclyl, such as $C_{3-8}$ heterocyclyl or $C_{3-8}$ substituted heterocyclyl, or $C_{3-6}$ heterocyclyl or $C_{3-6}$ substituted heterocyclyl, or $C_{3-5}$ heterocyclyl or $C_{3-5}$ substituted heterocyclyl. In certain embodiments, R is aryl or substituted aryl, such as $C_{3-8}$ aryl or $C_{3-8}$ substituted aryl, or $C_{3-6}$ aryl or $C_{3-6}$ substituted aryl (e.g., phenyl or substituted phenyl). In certain embodiments, R is heteroaryl or substituted heteroaryl, such as $C_{3-8}$ heteroaryl or $C_{3-8}$ substituted heteroaryl, or $C_{3-6}$ heteroaryl or $C_{3-6}$ substituted heteroaryl. In particular embodiments, R is —P(O)(OH)$_2$ or a salt thereof, and in other embodiments, R is —S(O)$_2$OH or a salt thereof.

In certain embodiments, X¹ is H, $C_{1-6}$ alkyl or a progroup. In certain embodiments, X¹ is H. In certain embodiments, X¹ is $C_{1-6}$ alkyl. In certain embodiments, X¹ is methyl. In certain embodiments, X¹ is ethyl. In certain embodiments, X¹ is propyl. In certain embodiments, X¹ is butyl. In certain embodiments, X¹ is pentyl. In certain embodiments, X¹ is hexyl. The $C_{1-6}$ alkyl may be unbranched or branched. For example, X¹ may be propyl, such as n-propyl or iso-propyl. For example, X¹ may be butyl, such as n-butyl, sec-butyl (1-methylpropyl), iso-butyl (2-methylpropyl) or tert-butyl (1,1-dimethylethyl).

In certain embodiments, X¹ is a progroup.
In certain embodiments, X¹ is a progroup of the formula:

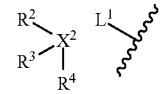

wherein
L¹ is a linking group;
X² is optional and selected from O, N and S;
R² is selected from hydrogen, alkyl, substituted alkyl, alkenyl, substituted alkenyl, alkynyl, substituted alkynyl, acyl, aminoacyl, carboxyl, carboxyl ester, cycloalkyl, substituted cycloalkyl, heterocyclyl, substituted heterocyclyl, aryl, substituted aryl, heteroaryl, and substituted heteroaryl; and
R³ and R⁴ are each independently optional and selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl; or
R² together with X² and either R³ or R⁴ form a heterocyclyl, substituted heterocyclyl, heteroaryl or substituted heteroaryl.

In certain embodiments, L¹ is a linking group. By "linking group" is meant a moiety that connects two or more portions of a compound together through one or more covalent bonds. For example, the linking group L¹ may connect X² to the rest of the compound, such as for example, the carboxyl oxygen of the compound of formula II.

In certain embodiments, L¹ is $C_{1-6}$ alkyl or substituted $C_{1-6}$ alkyl. In certain embodiments, L¹ is $C_{1-6}$ alkyl. In certain embodiments, L¹ is methyl. In certain embodiments, L¹ is ethyl. In certain embodiments, L¹ is propyl. In certain embodiments, L¹ is butyl. In certain embodiments, L¹ is pentyl. In certain embodiments, L¹ is hexyl. In certain embodiments, L¹ is substituted $C_{1-6}$ alkyl. In certain embodiments, L¹ is substituted methyl. In certain embodiments, L¹ is substituted ethyl. In certain embodiments, L¹ is substituted propyl. In certain embodiments, L¹ is substituted butyl. In certain embodiments, L¹ is substituted pentyl. In certain embodiments, L¹ is substituted hexyl. In certain embodiments, L¹ is substituted $C_{1-6}$ alkyl, where the alkyl is substituted with one or more groups selected from alkyl (e.g., $C_{1-6}$ alkyl), substituted alkyl (e.g., substituted $C_{1-6}$ alkyl), alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, L¹ is substituted $C_{1-6}$ alkyl, where the alkyl is substituted with a $C_{1-6}$ alkyl. In certain embodiments, L¹ is methyl substituted with one or two methyl groups. In certain embodiments, L¹ is ethyl substituted with one or two methyl groups.

In certain embodiments, X² is optional and selected from O, N and S. In certain embodiments, X² is not present. In embodiments where X² is not present, L¹ may be directly connected to R². In embodiments where X² is not present, L¹ may be directly connected to R³, if present. In embodiments where X² is not present, L¹ may be directly connected to R⁴, if present. In certain embodiments, X² is present. In embodiments where X² is present, X² may be O, N or S. In certain embodiments, X² is O. In some embodiments, when X² is, then $R^3$ and $R^4$ are not present. In certain embodiments, $X^2$ is N. In some embodiments, when $X^2$ is N, then $R^3$ is present and $R^4$ is not present. In certain embodiments, $X^2$ is S. In some embodiments, when $X^2$ is S, then $R^3$ and $R^4$ are present.

In certain embodiments, $R^2$ is selected from hydrogen, alkyl, substituted alkyl, alkenyl, substituted alkenyl, alkynyl, substituted alkynyl, acyl, aminoacyl, carboxyl, carboxyl ester, cycloalkyl, substituted cycloalkyl, heterocyclyl, substituted heterocyclyl, aryl, substituted aryl, heteroaryl, and substituted heteroaryl. In certain embodiments, $R^2$ is hydrogen. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is acyl. In certain embodiments, $R^2$ is aminoacyl. In certain embodiments, $R^2$ is carboxyl or carboxyl ester. In certain embodiments, $R^2$ is cycloalkyl or substituted cycloalkyl. In certain embodiments, $R^2$ is heterocyclyl or substituted heterocyclyl. In certain embodiments, $R^2$ is aryl or substituted aryl. In certain embodiments, $R^2$ is heteroaryl or substituted heteroaryl.

In certain embodiments, $R^3$ and $R^4$ are each independently optional and selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl.

In certain embodiments, $R^3$ is not present. In certain embodiments, $R^3$ is present and is selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl. In certain embodiments, $R^3$ is hydrogen. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is oxo. In certain embodiments, $R^3$ is cycloalkyl or substituted cycloalkyl. In certain embodiments, $R^3$ is heterocyclyl or substituted heterocyclyl. In certain embodiments, $R^3$ is aryl or substituted aryl. In certain embodiments, $R^3$ is heteroaryl or substituted heteroaryl.

In certain embodiments, $R^4$ is not present. In certain embodiments, $R^4$ is present and is selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl. In certain embodiments, $R^4$ is hydrogen. In certain embodiments, $R^4$ is alkyl or substituted alkyl. In certain embodiments, $R^4$ is alkenyl or substituted alkenyl. In certain embodiments, $R^4$ is alkynyl or substituted alkynyl. In certain embodiments, $R^4$ is oxo. In certain embodiments, $R^4$ is cycloalkyl or substituted cycloalkyl. In certain embodiments, $R^4$ is heterocyclyl or substituted heterocyclyl. In certain embodiments, $R^4$ is aryl or substituted aryl. In certain embodiments, $R^4$ is heteroaryl or substituted heteroaryl.

In certain embodiments, $X^2$ is N. In certain embodiments, when $X^2$ is N, then $R^3$ is present and $R^4$ is not present. In certain embodiments, $X^2$ is S. In some embodiments, when $X^2$ is S, then $R^3$ and $R^4$ are present. In certain embodiments, when $X^2$ is S, then $R^3$ and $R^4$ are both oxo.

In certain embodiments, $R^2$ together with $X^2$ and either $R^3$ or $R^4$ form a heterocyclyl, substituted heterocyclyl, heteroaryl or substituted heteroaryl. In certain embodiments, $R^2$ together with $X^2$ and either $R^3$ or $R^4$ form a heterocyclyl. In certain embodiments, $R^2$ together with $X^2$ and either $R^3$ or $R^4$ form a substituted heterocyclyl. In certain embodiments, $R^2$ together with $X^2$ and either $R^3$ or $R^4$ form a heteroaryl. In certain embodiments, $R^2$ together with $X^2$ and either $R^3$ or $R^4$ form a substituted heteroaryl. In certain embodiments, $X^2$ is N. In certain embodiments, when $X^2$ is N, then $R^3$ is present and $R^4$ is not present. As such, in certain embodiments, $R^2$ and $R^3$ together with the N to which they are attached form a heterocyclyl. In certain embodiments, $R^2$ and $R^3$ together with the N to which they are attached form a substituted heterocyclyl. In certain embodiments, $R^2$ and $R^3$ together with the N to which they are attached form a heteroaryl. In certain embodiments, $R^2$ and $R^3$ together with the N to which they are attached form a substituted heteroaryl. For example, in certain embodiments, $R^2$ and $R^3$ together with the N to which they are attached form a ring selected from piperazinyl, 1,3-oxazolidinyl, pyrrolidinyl, morpholinyl, imidazolidinyl, pyrazolidinyl, isoxazolidinyl, triazolidinyl, and piperidinyl.

In certain embodiments, $X^1$ is a progroup selected from:

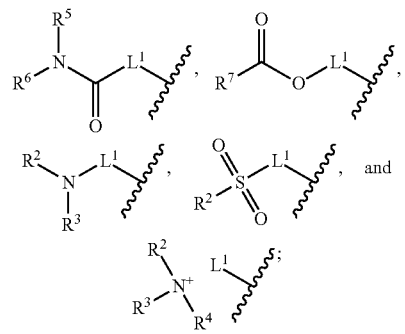

wherein $L^1$ is a $C_{1-6}$ alkyl or substituted $C_{1-6}$ alkyl;

$R^5$ and $R^6$ are each independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl; or $R^5$ and $R^6$ together with the nitrogen to which they are attached form a heterocyclyl, substituted heterocyclyl, heteroaryl or substituted heteroaryl;

$R^2$, $R^3$ and $R^4$ are as described above; and $R^7$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$OR^{14}$ where $R^{14}$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl.

As described above, in certain embodiments, $X^1$ is a progroup of the formula:

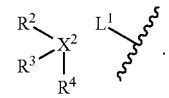

In certain embodiments, $X^2$ is not present, $R^2$ is aminoacyl, $R^3$ is not present, and $R^4$ is not present. As such, in certain embodiments, $X^1$ has the formula:

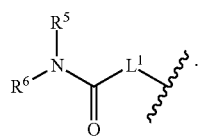

In certain embodiments, $L^1$ is $C_{1-6}$ alkyl or substituted $C_{1-6}$ alkyl. In certain embodiments, $L^1$ is $C_{1-6}$ alkyl. In certain embodiments, $L^1$ is methyl. In certain embodiments, $L^1$ is ethyl. In certain embodiments, $L^1$ is propyl. In certain embodiments, $L^1$ is butyl. In certain embodiments, $L^1$ is pentyl. In certain embodiments, $L^1$ is hexyl. In certain embodiments, $L^1$ is substituted $C_{1-6}$ alkyl. In certain embodiments, $L^1$ is substituted methyl. In certain embodiments, $L^1$ is substituted ethyl. In certain embodiments, $L^1$ is substituted propyl. In certain embodiments, $L^1$ is substituted butyl. In certain embodiments, $L^1$ is substituted pentyl. In certain embodiments, $L^1$ is substituted hexyl. In certain embodiments, $L^1$ is substituted $C_{1-6}$ alkyl, where the alkyl is substituted with one or more groups selected from alkyl (e.g., $C_{1-6}$ alkyl), substituted alkyl (e.g., substituted $C_{1-6}$ alkyl), alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $L^1$ is substituted $C_{1-6}$ alkyl, where the alkyl is substituted with a $C_{1-6}$ alkyl. In certain embodiments, $L^1$ is methyl substituted with one or two methyl groups. In certain embodiments, $L^1$ is ethyl substituted with one or two methyl groups.

In certain embodiments, $R^5$ and $R^6$ are each independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl.

In certain embodiments, $R^5$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $R^5$ is hydrogen. In certain embodiments, $R^5$ is alkyl or substituted alkyl. In certain embodiments, $R^5$ is alkenyl or substituted alkenyl. In certain embodiments, $R^5$ is alkynyl or substituted alkynyl. In certain embodiments, $R^5$ is cycloalkyl or substituted cycloalkyl. In certain embodiments, $R^5$ is heterocyclyl or substituted heterocyclyl. In certain embodiments, $R^5$ is aryl or substituted aryl. In certain embodiments, $R^5$ is heteroaryl or substituted heteroaryl.

In certain embodiments, $R^6$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $R^6$ is hydrogen. In certain embodiments, $R^6$ is alkyl or substituted alkyl. In certain embodiments, $R^6$ is alkenyl or substituted alkenyl. In certain embodiments, $R^6$ is alkynyl or substituted alkynyl. In certain embodiments, $R^6$ is cycloalkyl or substituted cycloalkyl. In certain embodiments, $R^6$ is heterocyclyl or substituted heterocyclyl. In certain embodiments, $R^6$ is aryl or substituted aryl. In certain embodiments, $R^6$ is heteroaryl or substituted heteroaryl.

In certain embodiments, $R^5$ and $R^6$ are each independently selected from hydrogen, alkyl (e.g., $C_{1-6}$ alkyl), and substituted alkyl (e.g., substituted $C_{1-6}$ alkyl). In certain embodiments, $R^5$ is hydrogen and $R^6$ is hydrogen. In certain embodiments, $R^5$ is hydrogen and $R^6$ is alkyl, such as $C_{1-6}$ alkyl (e.g., methyl, ethyl, propyl, butyl, pentyl or hexyl). In certain embodiments, $R^5$ is alkyl such as $C_{1-6}$ alkyl, and $R^6$ is alkyl such as $C_{1-6}$ alkyl. For example, in some instances, $R^5$ is methyl and $R^6$ is methyl, or one of $R^5$ and $R^6$ is methyl and the other is ethyl, or $R^5$ is ethyl and $R^6$ is ethyl. In certain embodiments, $R^5$ is hydrogen and $R^6$ is substituted alkyl, such as substituted $C_{1-6}$ alkyl (e.g., methyl, ethyl, propyl, butyl, pentyl or hexyl). In certain embodiments, $R^5$ is substituted alkyl such as substituted $C_{1-6}$ alkyl, and $R^6$ is substituted alkyl such as substituted $C_{1-6}$ alkyl.

In certain embodiments, $R^5$ is substituted $C_{1-6}$ alkyl, where the $C_{1-6}$ alkyl is substituted with one or more groups selected from alkyl, substituted alkyl, alkoxy, substituted alkoxy, oxo, acyl, acyloxy, carboxyl, carboxyl ester, amine, substituted amine, aminoacyl, acylamino, cycloalkyl, substituted cycloalkyl, heterocyclyl, substituted heterocyclyl, aryl, substituted aryl, heteroaryl, and substituted heteroaryl. For example, in certain embodiments, $R^5$ is substituted $C_{1-6}$ alkyl, such as, but not limited to, benzyl, 2-methoxyethyl, carboxymethyl, carboxypropyl, 2-(methylethoxy)ethyl, 2-ethoxyethyl, (tert-butyloxycarbonyl)methyl, (ethoxycarbonyl)methyl, (methylethyl)oxycarbonylmethyl, or ethoxycarbonylmethyl.

In certain embodiments, $R^6$ is substituted $C_{1-6}$ alkyl, where the $C_{1-6}$ alkyl is substituted with one or more groups selected from alkyl, substituted alkyl, alkoxy, substituted alkoxy, oxo, acyl, acyloxy, carboxyl, carboxyl ester, amine, substituted amine, aminoacyl, acylamino, cycloalkyl, substituted cycloalkyl, heterocyclyl, substituted heterocyclyl, aryl, substituted aryl, heteroaryl, and substituted heteroaryl. For example, in certain embodiments, $R^6$ is substituted $C_{1-6}$ alkyl, such as, but not limited to, benzyl, 2-methoxyethyl, carboxymethyl, carboxypropyl, 2-(methylethoxy)ethyl, 2-ethoxyethyl, (tert-butyloxycarbonyl)methyl, (ethoxycarbonyl)methyl, (methylethyl)oxycarbonylmethyl, or ethoxycarbonylmethyl.

In certain embodiments, $R^5$ and $R^6$ together with the nitrogen to which they are attached form a heterocyclyl, substituted heterocyclyl, heteroaryl or substituted heteroaryl. In certain embodiments, $R^5$ and $R^6$ together with the nitrogen to which they are attached form a heterocyclyl. In certain embodiments, $R^5$ and $R^6$ together with the nitrogen to which they are attached form a substituted heterocyclyl. In certain embodiments, $R^5$ and $R^6$ together with the nitrogen to which they are attached form a heteroaryl. In certain embodiments, $R^5$ and $R^6$ together with the nitrogen to which they are attached form a substituted heteroaryl. In certain embodiments, $R^5$ and $R^6$ together with the nitrogen to which they are attached form a ring selected from piperazinyl, 1,3-oxazolidinyl, 2-oxo(1,3-oxazolidinyl), pyrrolidinyl, morpholinyl, imidazolidinyl, pyrazolidinyl, isoxazolidinyl, triazolidinyl, and piperidinyl.

As described above, in certain embodiments, $X^1$ is a progroup of the formula:

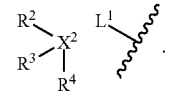

In certain embodiments, $X^2$ is O, $R^2$ is acyl, $R^3$ is not present, and $R^4$ is not present. As such, in certain embodiments, $X^1$ has the formula:

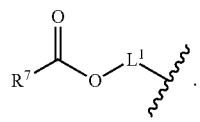

In certain embodiments, $L^1$ is $C_{1-6}$ alkyl or substituted $C_{1-6}$ alkyl. In certain embodiments, $L^1$ is $C_{1-6}$ alkyl. In certain embodiments, $L^1$ is methyl. In certain embodiments, $L^1$ is ethyl. In certain embodiments, $L^1$ is propyl. In certain embodiments, $L^1$ is butyl. In certain embodiments, $L^1$ is pentyl. In certain embodiments, $L^1$ is hexyl. In certain embodiments, $L^1$ is substituted $C_{1-6}$ alkyl. In certain embodiments, $L^1$ is substituted methyl. In certain embodiments, $L^1$ is substituted ethyl. In certain embodiments, $L^1$ is substituted propyl. In certain embodiments, $L^1$ is substituted butyl. In certain embodiments, $L^1$ is substituted pentyl. In certain embodiments, $L^1$ is substituted hexyl. In certain embodiments, $L^1$ is substituted $C_{1-6}$ alkyl, where the alkyl is substituted with one or more groups selected from alkyl (e.g., $C_{1-6}$ alkyl), substituted alkyl (e.g., substituted $C_{1-6}$ alkyl), alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $L^1$ is substituted $C_{1-6}$ alkyl, where the alkyl is substituted with a $C_{1-6}$ alkyl. In certain embodiments, $L^1$ is methyl substituted with one or two methyl groups. In certain embodiments, $L^1$ is ethyl substituted with one or two methyl groups.

In certain embodiments, $R^7$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$OR^{14}$ where $R^{14}$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $R^7$ is hydrogen. In certain embodiments, $R^7$ is alkyl or substituted alkyl. In certain embodiments, $R^7$ is alkenyl or substituted alkenyl. In certain embodiments, $R^7$ is alkynyl or substituted alkynyl. In certain embodiments, $R^7$ is cycloalkyl or substituted cycloalkyl. In certain embodiments, $R^7$ is heterocyclyl or substituted heterocyclyl. In certain embodiments, $R^7$ is aryl or substituted aryl. In certain embodiments, $R^7$ is heteroaryl or substituted heteroaryl. In certain embodiments, $R^7$ is —$OR^{14}$ where $R^{14}$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $R^{14}$ is alkyl or substituted alkyl. In certain embodiments, $R^{14}$ is alkenyl or substituted alkenyl. In certain embodiments, $R^{14}$ is alkynyl or substituted alkynyl. In certain embodiments, $R^{14}$ is cycloalkyl or substituted cycloalkyl. In certain embodiments, $R^{14}$ is heterocyclyl or substituted heterocyclyl. In certain embodiments, $R^{14}$ is aryl or substituted aryl. In certain embodiments, $R^{14}$ is heteroaryl or substituted heteroaryl.

In certain embodiments, $R^7$ is alkyl or substituted alkyl, such as $C_{1-6}$ alkyl or substituted $C_{1-6}$ alkyl. In certain embodiments, $R^7$ is $C_{1-6}$ alkyl, such as $C_{1-4}$ alkyl. For example, $R_7$ may be selected from methyl, ethyl, propyl (e.g., n-propyl or iso-propyl), and butyl (e.g., n-butyl, sec-butyl (1-methylpropyl), iso-butyl (2-methylpropyl) or tert-butyl (1,1-dimethylethyl)).

In certain embodiments, $R^7$ is substituted alkyl, such as substituted $C_{1-6}$ alkyl. In certain embodiments, $R^7$ is substituted $C_{1-6}$ alkyl, where the alkyl is substituted with one or more groups selected from alkyl, substituted alkyl, alkoxy, substituted alkoxy, oxo, acyl, acyloxy, carboxyl, carboxyl ester, amine, substituted amine, aminoacyl, acylamino, cycloalkyl, substituted cycloalkyl, heterocyclyl, substituted heterocyclyl, aryl, substituted aryl, heteroaryl, and substituted heteroaryl.

For example, in certain embodiments, $R^7$ is selected from ethoxy, methylethoxy, iso-propyl, phenyl, cyclohexyl, cyclohexyloxy, —$CH(NH_2)CH_2COOH$, —$CH_2CH(NH_2)COOH$, —$CH(NHC(O)CH_2NH_2)CH_2COOH$, and —$CH_2CH(NHC(O)CH_2NH_2)COOH$.

As described above, in certain embodiments, $X^1$ is a progroup of the formula:

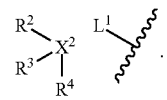

In certain embodiments, $X^2$ is N, $R^2$ is present, $R^3$ is present, and $R^4$ is not present. As such, in certain embodiments, $X^1$ has the formula:

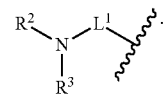

In certain embodiments, $L^1$ is $C_{1-6}$ alkyl or substituted $C_{1-6}$ alkyl. In certain embodiments, $L^1$ is $C_{1-6}$ alkyl. In certain embodiments, $L^1$ is methyl. In certain embodiments, $L^1$ is ethyl. In certain embodiments, $L^1$ is propyl. In certain embodiments, $L^1$ is butyl. In certain embodiments, $L^1$ is pentyl. In certain embodiments, $L^1$ is hexyl. In certain embodiments, $L^1$ is substituted $C_{1-6}$ alkyl. In certain embodiments, $L^1$ is substituted methyl. In certain embodiments, $L^1$ is substituted ethyl. In certain embodiments, $L^1$ is substituted propyl. In certain embodiments, $L^1$ is substituted butyl. In certain embodiments, $L^1$ is substituted pentyl. In certain embodiments, $L^1$ is substituted hexyl. In certain embodiments, $L^1$ is substituted $C_{1-6}$ alkyl, where the alkyl is substituted with one or more groups selected from alkyl (e.g., $C_{1-6}$ alkyl), substituted alkyl (e.g., substituted $C_{1-6}$ alkyl), alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $L^1$ is substituted $C_{1-6}$ alkyl, where the alkyl is substituted with a $C_{1-6}$ alkyl. In certain embodiments, $L^1$ is methyl substituted with one or two methyl groups. In certain embodiments, $L^1$ is ethyl substituted with one or two methyl groups.

In certain embodiments, $R^2$ is selected from hydrogen, alkyl, substituted alkyl, alkenyl, substituted alkenyl, alkynyl, substituted alkynyl, acyl, aminoacyl, carboxyl, carboxyl ester, cycloalkyl, substituted cycloalkyl, heterocyclyl, substituted heterocyclyl, aryl, substituted aryl, heteroaryl, and substituted heteroaryl. In certain embodiments, $R^2$ is hydrogen. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is acyl. In certain embodiments, $R^2$ is aminoacyl. In certain embodiments, $R^2$ is carboxyl or carboxyl ester. In certain embodiments, $R^2$ is cycloalkyl or substituted cycloalkyl. In certain embodiments, $R^2$ is heterocyclyl or substituted heterocyclyl. In certain embodiments, $R^2$ is aryl or substituted aryl. In certain embodiments, $R^2$ is heteroaryl or substituted heteroaryl.

For example, in some embodiments, $R^2$ is $C_{1-6}$ alkyl, such as methyl, ethyl, propyl, butyl, pentyl or hexyl. In some embodiments, $R^2$ is carboxyl or carboxyl ester, such as —$COOR^a$, where $R^a$ is hydrogen or $C_{1-6}$ alkyl. In some embodiments, $R^2$ is aryl or substituted aryl, such as phenyl or substituted phenyl.

In certain embodiments, $R^3$ is selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl. In certain embodiments, $R^3$ is hydrogen. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is oxo. In certain embodiments, $R^3$ is cycloalkyl or substituted cycloalkyl. In certain embodiments, $R^3$ is heterocyclyl or substituted heterocyclyl. In certain embodiments, $R^3$ is aryl or substituted aryl. In certain embodiments, $R^3$ is heteroaryl or substituted heteroaryl.

For example, in some embodiments, $R^3$ is $C_{1-6}$ alkyl, such as methyl, ethyl, propyl, butyl, pentyl or hexyl. In some embodiments, $R^3$ is substituted $C_{1-6}$ alkyl, such as substituted $C_{1-3}$ alkyl or substituted $C_{1-2}$ alkyl.

In certain embodiments, $R^2$ and $R^3$ together with the N to which they are attached form a heterocyclyl. In certain embodiments, $R^2$ and $R^3$ together with the N to which they are attached form a substituted heterocyclyl. In certain embodiments, $R^2$ and $R^3$ together with the N to which they are attached form a succinimidyl. In certain embodiments, $R^2$ and $R^3$ together with the N to which they are attached form a heteroaryl. In certain embodiments, $R^2$ and $R^3$ together with the N to which they are attached form a substituted heteroaryl. For example, in certain embodiments, $R^2$ and $R^3$ together with the N to which they are attached form a ring selected from piperazinyl, 1,3-oxazolidinyl, pyrrolidinyl, morpholinyl, imidazolidinyl, pyrazolidinyl, isoxazolidinyl, triazolidinyl, and piperidinyl.

As described above, in certain embodiments, $X^1$ is a progroup of the formula:

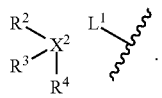

In certain embodiments, $X^2$ is S, $R^2$ is present, $R^3$ is oxo, and $R^4$ is oxo. As such, in certain embodiments, $X^1$ has the formula:

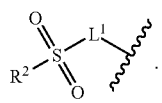

In certain embodiments, $L^1$ is $C_{1-6}$ alkyl or substituted $C_{1-6}$ alkyl. In certain embodiments, $L^1$ is $C_{1-6}$ alkyl. In certain embodiments, $L^1$ is methyl. In certain embodiments, $L^1$ is ethyl. In certain embodiments, $L^1$ is propyl. In certain embodiments, $L^1$ is butyl. In certain embodiments, $L^1$ is pentyl. In certain embodiments, $L^1$ is hexyl. In certain embodiments, $L^1$ is substituted $C_{1-6}$ alkyl. In certain embodiments, $L^1$ is substituted methyl. In certain embodiments, $L^1$ is substituted ethyl. In certain embodiments, $L^1$ is substituted propyl. In certain embodiments, $L^1$ is substituted butyl. In certain embodiments, $L^1$ is substituted pentyl. In certain embodiments, $L^1$ is substituted hexyl. In certain embodiments, $L^1$ is substituted $C_{1-6}$ alkyl, where the alkyl is substituted with one or more groups selected from alkyl (e.g., $C_{1-6}$ alkyl), substituted alkyl (e.g., substituted $C_{1-6}$ alkyl), alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $L^1$ is substituted $C_{1-6}$ alkyl, where the alkyl is substituted with a $C_{1-6}$ alkyl. In certain embodiments, $L^1$ is methyl substituted with one or two methyl groups. In certain embodiments, $L^1$ is ethyl substituted with one or two methyl groups.

In certain embodiments, $R^2$ is selected from hydrogen, alkyl, substituted alkyl, alkenyl, substituted alkenyl, alkynyl, substituted alkynyl, acyl, aminoacyl, carboxyl, carboxyl ester, cycloalkyl, substituted cycloalkyl, heterocyclyl, substituted heterocyclyl, aryl, substituted aryl, heteroaryl, and substituted heteroaryl. In certain embodiments, $R^2$ is hydrogen. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is acyl. In certain embodiments, $R^2$ is aminoacyl. In certain embodiments, $R^2$ is carboxyl or carboxyl ester. In certain embodiments, $R^2$ is cycloalkyl or substituted cycloalkyl. In certain embodiments, $R^2$ is heterocyclyl or substituted heterocyclyl. In certain embodiments, $R^2$ is aryl or substituted aryl. In certain embodiments, $R^2$ is heteroaryl or substituted heteroaryl.

For example, in some embodiments, $R^2$ is $C_{1-6}$ alkyl, such as methyl, ethyl, propyl, butyl, pentyl or hexyl.

As described above, in certain embodiments, $X^1$ is a progroup of the formula:

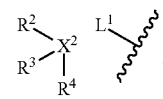

In certain embodiments, $X^2$ is N, $R^2$ is present, $R^3$ is present, and $R^4$ is present. In these embodiments, the N is a quaternary amine. As such, in certain embodiments, $X^1$ has the formula:

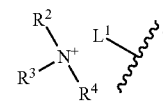

In certain embodiments, $L^1$ is $C_{1-6}$ alkyl or substituted $C_{1-6}$ alkyl. In certain embodiments, $L^1$ is $C_{1-6}$ alkyl. In certain embodiments, $L^1$ is methyl. In certain embodiments, $L^1$ is ethyl. In certain embodiments, $L^1$ is propyl. In certain embodiments, $L^1$ is butyl. In certain embodiments, $L^1$ is pentyl. In certain embodiments, $L^1$ is hexyl. In certain embodiments, $L^1$ is substituted $C_{1-6}$ alkyl. In certain embodiments, $L^1$ is substituted methyl. In certain embodiments, $L^1$ is substituted ethyl. In certain embodiments, $L^1$ is substituted propyl. In certain embodiments, $L^1$ is substituted butyl. In certain embodiments, $L^1$ is substituted pentyl. In certain embodiments, $L^1$ is substituted hexyl. In certain embodiments, $L^1$ is substituted $C_{1-6}$ alkyl, where the alkyl is substituted with one or more groups selected from alkyl (e.g., $C_{1-6}$ alkyl), substituted alkyl (e.g., substituted $C_{1-6}$ alkyl), alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl. In certain embodiments, $L^1$ is substituted $C_{1-6}$ alkyl, where the alkyl is substituted with a $C_{1-6}$ alkyl. In certain embodiments, $L^1$ is methyl substituted with one or two methyl groups. In certain embodiments, $L^1$ is ethyl substituted with one or two methyl groups.

In certain embodiments, $R^2$ is selected from hydrogen, alkyl, substituted alkyl, alkenyl, substituted alkenyl, alkynyl, substituted alkynyl, acyl, aminoacyl, carboxyl, carboxyl ester, cycloalkyl, substituted cycloalkyl, heterocyclyl, substituted heterocyclyl, aryl, substituted aryl, heteroaryl, and substituted heteroaryl. In certain embodiments, $R^2$ is hydrogen. In certain embodiments, $R^2$ is alkyl or substituted alkyl. In certain embodiments, $R^2$ is alkenyl or substituted alkenyl. In certain embodiments, $R^2$ is alkynyl or substituted alkynyl. In certain embodiments, $R^2$ is acyl. In certain embodiments, $R^2$ is aminoacyl. In certain embodiments, $R^2$ is carboxyl or carboxyl ester. In certain embodiments, $R^2$ is cycloalkyl or substituted cycloalkyl. In certain embodiments, $R^2$ is heterocyclyl or substituted heterocyclyl. In certain embodiments, $R^2$ is aryl or substituted aryl. In certain embodiments, $R^2$ is heteroaryl or substituted heteroaryl.

For example, in some embodiments, $R^2$ is $C_{1-6}$ alkyl, such as methyl, ethyl, propyl, butyl, pentyl or hexyl. In some embodiments, $R^2$ is carboxyl or carboxyl ester, such as $-COOR^a$, where $R^a$ is hydrogen or $C_{1-6}$ alkyl. In some embodiments, $R^2$ is aryl or substituted aryl, such as phenyl or substituted phenyl.

In certain embodiments, $R^3$ is selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl. In certain embodiments, $R^3$ is hydrogen. In certain embodiments, $R^3$ is alkyl or substituted alkyl. In certain embodiments, $R^3$ is alkenyl or substituted alkenyl. In certain embodiments, $R^3$ is alkynyl or substituted alkynyl. In certain embodiments, $R^3$ is oxo. In certain embodiments, $R^3$ is cycloalkyl or substituted cycloalkyl. In certain embodiments, $R^3$ is heterocyclyl or substituted heterocyclyl. In certain embodiments, $R^3$ is aryl or substituted aryl. In certain embodiments, $R^3$ is heteroaryl or substituted heteroaryl.

For example, in some embodiments, $R^3$ is $C_{1-6}$ alkyl, such as methyl, ethyl, propyl, butyl, pentyl or hexyl. In some embodiments, $R^3$ is substituted $C_{1-6}$ alkyl, such as substituted $C_{1-3}$ alkyl or substituted $C_{1-2}$ alkyl.

In certain embodiments, $R^4$ is selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl. In certain embodiments, $R^4$ is hydrogen. In certain embodiments, $R^4$ is alkyl or substituted alkyl. In certain embodiments, $R^4$ is alkenyl or substituted alkenyl. In certain embodiments, $R^4$ is alkynyl or substituted alkynyl. In certain embodiments, $R^4$ is oxo. In certain embodiments, $R^4$ is cycloalkyl or substituted cycloalkyl. In certain embodiments, $R^4$ is heterocyclyl or substituted heterocyclyl. In certain embodiments, $R^4$ is aryl or substituted aryl. In certain embodiments, $R^4$ is heteroaryl or substituted heteroaryl.

For example, in some embodiments, $R^4$ is $C_{1-6}$ alkyl, such as methyl, ethyl, propyl, butyl, pentyl or hexyl. In some embodiments, $R^4$ is substituted $C_{1-6}$ alkyl, such as substituted $C_{1-3}$ alkyl or substituted $C_{1-2}$ alkyl.

In certain embodiments, $R^2$ and $R^3$ together with the N to which they are attached form a heterocyclyl. In certain embodiments, $R^2$ and $R^3$ together with the N to which they are attached form a substituted heterocyclyl. In certain embodiments, $R^2$ and $R^3$ together with the N to which they are attached form a heteroaryl. In certain embodiments, $R^2$ and $R^3$ together with the N to which they are attached form a substituted heteroaryl. For example, in certain embodiments, $R^2$ and $R^3$ together with the N to which they are attached form a ring selected from piperazinyl, 1,3-oxazolidinyl, pyrrolidinyl, morpholinyl, imidazolidinyl, pyrazolidinyl, isoxazolidinyl, triazolidinyl, and piperidinyl.

In certain embodiments, $X^1$ is a progroup selected from:

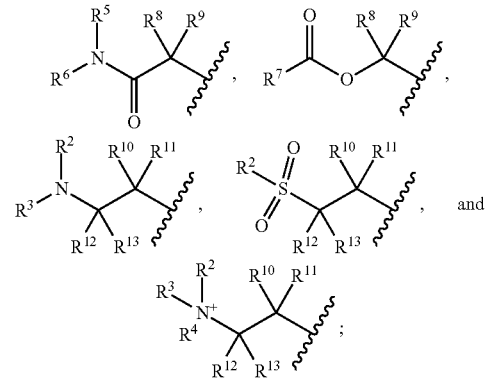

wherein $R^2$, $R^3$, $R^5$, $R^6$ and $R^7$ are as described above; and $R^8$, $R^9$, $R^{10}$, $R^{11}$, $R^{12}$ and $R^{13}$ are each independently selected from hydrogen, alkyl and substituted alkyl.

In the formulae above for $X^1$, the substituents $R^2$, $R^3$, $R^4$, $R^5$, $R^6$, and $R^7$ are as described above.

In certain embodiments, $X^1$ has the formula:

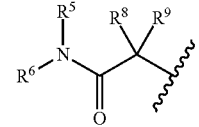

wherein $R^5$ and $R^6$ are as described above; and $R^8$ and $R^9$ are each independently selected from hydrogen, alkyl and substituted alkyl.

In the formula above for $X^1$, the substituents $R^5$ and $R^6$ are as described above.

In certain embodiments, $R^8$ is selected from hydrogen, alkyl and substituted alkyl. In certain embodiments, $R^8$ is hydrogen. In certain embodiments, $R^8$ is alkyl, such as $C_{1-6}$ alkyl (e.g., methyl, ethyl, propyl, butyl, pentyl or hexyl). In certain embodiments, $R^8$ is substituted alkyl, such as substituted $C_{1-6}$ alkyl, substituted $C_{1-3}$ alkyl, or substituted $C_{1-2}$ alkyl.

In certain embodiments, $R^9$ is selected from hydrogen, alkyl and substituted alkyl. In certain embodiments, $R^9$ is hydrogen. In certain embodiments, $R^9$ is alkyl, such as $C_{1-6}$ alkyl (e.g., methyl, ethyl, propyl, butyl, pentyl or hexyl). In certain embodiments, $R^9$ is substituted alkyl, such as substituted $C_{1-6}$ alkyl, substituted $C_{1-3}$ alkyl, or substituted $C_{1-2}$ alkyl.

In certain embodiments, $R^8$ and $R^9$ are each hydrogen. In certain embodiments, one of $R^8$ and $R^9$ is hydrogen and the other is alkyl, such as $C_{1-6}$ alkyl as described above.

In certain embodiments, $X^1$ has the formula:

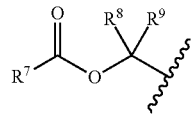

wherein $R^7$ is as described above; and $R^8$ and $R^9$ are each independently selected from hydrogen, alkyl and substituted alkyl.

In the formula above for $X^1$, the substituent $R^7$ is as described above.

In certain embodiments, R is selected from hydrogen, alkyl and substituted alkyl. In certain embodiments, $R^8$ is hydrogen. In certain embodiments, $R^8$ is alkyl, such as $C_{1-6}$ alkyl (e.g., methyl, ethyl, propyl, butyl, pentyl or hexyl). In certain embodiments, $R^8$ is substituted alkyl, such as substituted $C_{1-6}$ alkyl, substituted $C_{1-3}$ alkyl, or substituted $C_{1-2}$ alkyl.

In certain embodiments, $R^9$ is selected from hydrogen, alkyl and substituted alkyl. In certain embodiments, $R^9$ is hydrogen. In certain embodiments, $R^9$ is alkyl, such as $C_{1-6}$ alkyl (e.g., methyl, ethyl, propyl, butyl, pentyl or hexyl). In certain embodiments, $R^9$ is substituted alkyl, such as substituted $C_{1-6}$ alkyl, substituted $C_{1-3}$ alkyl, or substituted $C_{1-2}$ alkyl.

In certain embodiments, $R^8$ and $R^9$ are each hydrogen. In certain embodiments, one of $R^8$ and $R^9$ is hydrogen and the other is alkyl, such as $C_{1-6}$ alkyl as described above.

In certain embodiments, $X^1$ has the formula:

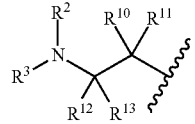

wherein $R^2$ and R are as described above; and $R^{10}$, $R^{11}$, $R^{12}$ and $R^{13}$ are each independently selected from hydrogen, alkyl and substituted alkyl.

In the formula above for $X^1$, the substituent $R^2$ and $R^3$ are as described above.

In certain embodiments, $R^{10}$ is selected from hydrogen, alkyl and substituted alkyl. In certain embodiments, $R^{10}$ is hydrogen. In certain embodiments, $R^{10}$ is alkyl, such as $C_{1-6}$ alkyl (e.g., methyl, ethyl, propyl, butyl, pentyl or hexyl). In certain embodiments, $R^{10}$ is substituted alkyl, such as substituted $C_{1-6}$ alkyl, substituted $C_{1-3}$ alkyl, or substituted $C_{1-2}$ alkyl.

In certain embodiments, $R^{11}$ is selected from hydrogen, alkyl and substituted alkyl. In certain embodiments, $R^{11}$ is hydrogen. In certain embodiments, $R^{11}$ is alkyl, such as $C_{1-6}$ alkyl (e.g., methyl, ethyl, propyl, butyl, pentyl or hexyl). In certain embodiments, $R^{11}$ is substituted alkyl, such as substituted $C_{1-6}$ alkyl, substituted $C_{1-3}$ alkyl, or substituted $C_{1-2}$ alkyl.

In certain embodiments, $R^{12}$ is selected from hydrogen, alkyl and substituted alkyl. In certain embodiments, $R^{12}$ is hydrogen. In certain embodiments, $R^{12}$ is alkyl, such as $C_{1-6}$ alkyl (e.g., methyl, ethyl, propyl, butyl, pentyl or hexyl). In certain embodiments, $R^{12}$ is substituted alkyl, such as substituted $C_{1-6}$ alkyl, substituted $C_{1-3}$ alkyl, or substituted $C_{1-2}$ alkyl.

In certain embodiments, $R^{13}$ is selected from hydrogen, alkyl and substituted alkyl. In certain embodiments, $R^{13}$ is hydrogen. In certain embodiments, $R^{13}$ is alkyl, such as $C_{1-6}$ alkyl (e.g., methyl, ethyl, propyl, butyl, pentyl or hexyl). In certain embodiments, $R^{13}$ is substituted alkyl, such as substituted $C_{1-6}$ alkyl, substituted $C_{1-3}$ alkyl, or substituted $C_{1-2}$ alkyl.

In certain embodiments, $R^{10}$, $R^{11}$, $R^{12}$ and $R^{13}$ are each independently selected from hydrogen and $C_{1-6}$ alkyl. In certain embodiments, $R^{10}$, $R^{11}$, $R^{12}$ and $R^{13}$ are each hydrogen. In certain embodiments, one of $R^{10}$, $R^{11}$, $R^{12}$ and $R^{13}$ is $C_{1-6}$ alkyl and the remaining are hydrogen. For example, in some instances, one of $R^{10}$, $R^{11}$, $R^{12}$ and $R^{13}$ is methyl and the remaining are hydrogen. In some instances, $R^{10}$ is $C_{1-6}$ alkyl (e.g., methyl) and $R^{11}$, $R^{12}$ and $R^{13}$ are hydrogen. In some instances, $R^{11}$ is $C_{1-6}$ alkyl (e.g., methyl) and $R^{10}$, $R^{12}$ and $R^{13}$ are hydrogen. In some instances, $R^{12}$ is $C_{1-6}$ alkyl (e.g., methyl) and $R^{10}$, $R^{11}$ and $R^{13}$ are hydrogen. In some instances, $R^{13}$ is $C_{1-6}$ alkyl (e.g., methyl) and $R^{10}$, $R^{11}$ and $R^{12}$ are hydrogen. In certain embodiments, two of $R^{10}$, $R^{11}$, $R^{12}$ and $R^{13}$ are methyl and the remaining are hydrogen. For example, in some instances, two of $R^{10}$, $R^{11}$, $R^{12}$ and $R^{13}$ are methyl and the remaining are hydrogen. In some instances, $R^{10}$ and $R^{11}$ are $C_{1-6}$ alkyl (e.g., methyl) and $R^{12}$ and $R^{13}$ are hydrogen. In some instances, $R^{10}$ and $R^{12}$ are $C_{1-6}$ alkyl (e.g., methyl) and $R^{11}$ and $R^{13}$ are hydrogen. In some instances, $R^{10}$ and $R^{13}$ are $C_{1-6}$ alkyl (e.g., methyl) and $R^{11}$ and $R^{12}$ are hydrogen. In some instances, $R^{11}$ and $R^{12}$ are $C_{1-6}$ alkyl (e.g., methyl) and R and $R^{13}$ are hydrogen. In some instances, $R^{11}$ and $R^{13}$ are $C_{1-6}$ alkyl (e.g., methyl) and $R^{10}$ and $R^{12}$ are hydrogen. In some instances, $R^{12}$ and $R^{13}$ are $C_{1-6}$ alkyl (e.g., methyl) and $R^{10}$ and $R^1$ are hydrogen.

In certain embodiments, $X^1$ has the formula:

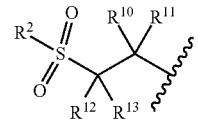

wherein $R^2$ is as described above; and $R^{10}$, $R^{11}$, $R^{12}$ and $R^{13}$ are each independently selected from hydrogen, alkyl and substituted alkyl.

In the formula above for $X^1$, the substituent $R^2$ is as described above.

In certain embodiments, $R^{10}$ is selected from hydrogen, alkyl and substituted alkyl. In certain embodiments, $R^{10}$ is hydrogen. In certain embodiments, $R^{10}$ is alkyl, such as $C_{1-6}$ alkyl (e.g., methyl, ethyl, propyl, butyl, pentyl or hexyl). In certain embodiments, $R^{10}$ is substituted alkyl, such as substituted $C_{1-6}$ alkyl, substituted $C_{1-3}$ alkyl, or substituted $C_{1-2}$ alkyl.

In certain embodiments, $R^{11}$ is selected from hydrogen, alkyl and substituted alkyl. In certain embodiments, $R^{11}$ is hydrogen. In certain embodiments, $R^{11}$ is alkyl, such as $C_{1-6}$ alkyl (e.g., methyl, ethyl, propyl, butyl, pentyl or hexyl). In certain embodiments, $R^{11}$ is substituted alkyl, such as substituted $C_{1-6}$ alkyl, substituted $C_{1-3}$ alkyl, or substituted $C_{1-2}$ alkyl.

In certain embodiments, $R^{12}$ is selected from hydrogen, alkyl and substituted alkyl. In certain embodiments, $R^{12}$ is hydrogen. In certain embodiments, $R^{12}$ is alkyl, such as $C_{1-6}$ alkyl (e.g., methyl, ethyl, propyl, butyl, pentyl or hexyl). In certain embodiments, $R^{12}$ is substituted alkyl, such as substituted $C_{1-6}$ alkyl, substituted $C_{1-3}$ alkyl, or substituted $C_{1-2}$ alkyl.

In certain embodiments, $R^{13}$ is selected from hydrogen, alkyl and substituted alkyl. In certain embodiments, $R^{13}$ is hydrogen. In certain embodiments, $R^{13}$ is alkyl, such as $C_{1-6}$ alkyl (e.g., methyl, ethyl, propyl, butyl, pentyl or hexyl). In certain embodiments, $R^{13}$ is substituted alkyl, such as substituted $C_{1-6}$ alkyl, substituted $C_{1-3}$ alkyl, or substituted $C_{1-2}$ alkyl.

In certain embodiments, $R^{10}$, $R^{11}$, $R^{12}$ and $R^{13}$ are each independently selected from hydrogen and $C_{1-6}$ alkyl. In certain embodiments, $R^{10}$, $R^{11}$, $R^{12}$ and $R^{13}$ are each hydrogen. In certain embodiments, one of $R^{10}$, $R^{11}$, $R^{12}$ and $R^{13}$ is $C_{1-6}$ alkyl and the remaining are hydrogen. For example, in some instances, one of $R^{10}$, $R^{11}$, $R^{12}$ and $R^{13}$ is methyl and the remaining are hydrogen. In some instances, $R^{10}$ is $C_{1-6}$ alkyl (e.g., methyl) and $R^{11}$, $R^{12}$ and $R^{13}$ are hydrogen. In some instances, $R^{11}$ is $C_{1-6}$ alkyl (e.g., methyl) and $R^{10}$, $R^{12}$ and $R^{13}$ are hydrogen. In some instances, $R^{12}$ is $C_{1-6}$ alkyl (e.g., methyl) and $R^{10}$, $R^{11}$ and $R^{13}$ are hydrogen. In some instances, $R^{13}$ is $C_{1-6}$ alkyl (e.g., methyl) and $R^{10}$, $R^{11}$ and $R^{12}$ are hydrogen. In certain embodiments, two of $R^{10}$, $R^{11}$, $R^{12}$ and $R^{13}$ are methyl and the remaining are hydrogen. For example, in some instances, two of $R^{10}$, $R^{11}$, $R^{12}$ and $R^{13}$ are methyl and the remaining are hydrogen. In some instances, $R^{10}$ and $R^{11}$ are $C_{1-6}$ alkyl (e.g., methyl) and $R^{12}$ and $R^{13}$ are hydrogen. In some instances, $R^{10}$ and $R^{12}$ are $C_{1-6}$ alkyl (e.g., methyl) and $R^{11}$ and $R^{13}$ are hydrogen. In some instances, $R^{10}$ and $R^{13}$ are $C_{1-6}$ alkyl (e.g., methyl) and $R^{11}$ and $R^{12}$ are hydrogen. In some instances, $R^{11}$ and $R^{12}$ are $C_{1-6}$ alkyl (e.g., methyl) and $R^{10}$ and $R^{13}$ are hydrogen. In some instances, $R^{11}$ and $R^{13}$ are $C_{1-6}$ alkyl (e.g., methyl) and $R^{10}$ and $R^{12}$ are hydrogen. In some instances, $R^{12}$ and $R^{13}$ are $C_{1-6}$ alkyl (e.g., methyl) and $R^{10}$ and $R^{11}$ are hydrogen.

In certain embodiments, $X^1$ has the formula:

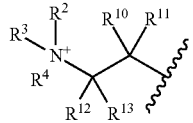

wherein $R^2$, $R^3$ and $R^4$ are as described above; and $R^{10}$, $R^{11}$, $R^{12}$ and $R^{13}$ are each independently selected from hydrogen, alkyl and substituted alkyl.

In the formula above for $X^1$, the substituents $R^2$, $R^3$ and $R^4$ are as described above.

In certain embodiments, $R^{10}$ is selected from hydrogen, alkyl and substituted alkyl. In certain embodiments, $R^{10}$ is hydrogen. In certain embodiments, $R^{10}$ is alkyl, such as $C_{1-6}$ alkyl (e.g., methyl, ethyl, propyl, butyl, pentyl or hexyl). In certain embodiments, $R^{10}$ is substituted alkyl, such as substituted $C_{1-6}$ alkyl, substituted $C_{1-3}$ alkyl, or substituted $C_{1-2}$ alkyl.

In certain embodiments, $R^{11}$ is selected from hydrogen, alkyl and substituted alkyl. In certain embodiments, $R^{11}$ is hydrogen. In certain embodiments, $R^{11}$ is alkyl, such as $C_{1-6}$ alkyl (e.g., methyl, ethyl, propyl, butyl, pentyl or hexyl). In certain embodiments, $R^{11}$ is substituted alkyl, such as substituted $C_{1-6}$ alkyl, substituted $C_{1-3}$ alkyl, or substituted $C_{1-2}$ alkyl.

In certain embodiments, $R^{12}$ is selected from hydrogen, alkyl and substituted alkyl. In certain embodiments, $R^{12}$ is hydrogen. In certain embodiments, $R^{12}$ is alkyl, such as $C_{1-6}$ alkyl (e.g., methyl, ethyl, propyl, butyl, pentyl or hexyl). In certain embodiments, $R^{12}$ is substituted alkyl, such as substituted $C_{1-6}$ alkyl, substituted $C_{1-3}$ alkyl, or substituted $C_{1-2}$ alkyl.

In certain embodiments, $R^{13}$ is selected from hydrogen, alkyl and substituted alkyl. In certain embodiments, $R^{13}$ is hydrogen. In certain embodiments, $R^{13}$ is alkyl, such as $C_{1-6}$ alkyl (e.g., methyl, ethyl, propyl, butyl, pentyl or hexyl). In certain embodiments, $R^{13}$ is substituted alkyl, such as substituted $C_{1-6}$ alkyl, substituted $C_{1-3}$ alkyl, or substituted $C_{1-2}$ alkyl.

In certain embodiments, $R^{10}$, $R^{11}$, $R^{12}$ and $R^{13}$ are each independently selected from hydrogen and $C_{1-6}$ alkyl. In certain embodiments, $R^{10}$, $R^{11}$, $R^{12}$ and $R^{13}$ are each hydrogen. In certain embodiments, one of $R^{10}$, $R^{11}$, $R^{12}$ and $R^{13}$ is $C_{1-6}$ alkyl and the remaining are hydrogen. For example, in some instances, one of $R^{10}$, $R^{11}$, $R^{12}$ and $R^{13}$ is methyl and the remaining are hydrogen. In some instances, $R^{10}$ is $C_{1-6}$ alkyl (e.g., methyl) and $R^{11}$, $R^{12}$ and $R^{13}$ are hydrogen. In some instances, $R^{11}$ is $C_{1-6}$ alkyl (e.g., methyl) and $R^{10}$, $R^{12}$ and $R^{13}$ are hydrogen. In some instances, $R^{12}$ is $C_{1-6}$ alkyl (e.g., methyl) and $R^{10}$, $R^{11}$ and $R^{13}$ are hydrogen. In some instances, $R^{13}$ is $C_{1-6}$ alkyl (e.g., methyl) and $R^{10}$, $R^{11}$ and $R^{12}$ are hydrogen. In certain embodiments, two of $R^{10}$, $R^{11}$, $R^{12}$ and $R^{13}$ are methyl and the remaining are hydrogen. For example, in some instances, two of $R^{10}$, $R^{11}$, $R^{12}$ and $R^{13}$ are methyl and the remaining are hydrogen. In some instances, $R^{10}$ and $R^{11}$ are $C_{1-6}$ alkyl (e.g., methyl) and $R^{12}$ and $R^{13}$ are hydrogen. In some instances, $R^{10}$ and $R^{12}$ are $C_{1-6}$ alkyl (e.g., methyl) and $R^{11}$ and $R^{13}$ are hydrogen. In some instances, $R^{10}$ and $R^{13}$ are $C_{1-6}$ alkyl (e.g., methyl) and $R^{11}$ and $R^{12}$ are hydrogen. In some instances, $R^{11}$ and $R^{12}$ are $C_{1-6}$ alkyl (e.g., methyl) and $R^{10}$ and $R^{13}$ are hydrogen. In some instances, $R^{11}$ and $R^{13}$ are $C_{1-6}$ alkyl (e.g., methyl) and $R^{10}$ and $R^{12}$ are hydrogen. In some instances, $R^{12}$ and $R^{13}$ are $C_{1-6}$ alkyl (e.g., methyl) and $R^{10}$ and $R^{11}$ are hydrogen.

In some embodiments, the compound is a dimer. In these embodiments, $R^1$ is $R^{15}$, where $R^{15}$ includes a linking group and a second compound of formula (IIa) or (IIb). In certain embodiments, the linking group is an alkyl linking group, such as a $C_{1-10}$ alkyl linking group, or a $C_{1-8}$ alkyl linking group, or a $C_{1-6}$ alkyl linking group, or a $C_{1-3}$ alkyl linking group. In certain embodiments, the linking group attaches a first compound of formula (IIa) or (IIb) to a second compound of formula (IIa) or (IIb). In some instances, the first compound of formula (IIa) or (IIb) has one end of the linking group attached at the $R^1$ position, and the other end of the linking group is attached at the $R^1$ position of the second compound of formula (IIa) or (IIb). In these embodiments, the two compounds of formula (IIa) and/or (IIb) in the dimer are connected to each other at their respective $R^1$ positions through the linking group. In certain embodiments, the compound is a symmetrical dimer. In some instances, the compound is an unsymmetrical dimer. In certain embodiments, two compounds of formula (IIa) are connected to each other in the dimer at their respective $R^1$ positions through the linking group. In certain embodiments, two compounds of formula (IIb) are connected to each other in the dimer at their respective $R^1$ positions through the linking group.

In certain embodiments, the linking group is has the structure: —$(CH_2)_n$—$Z_y$—$(CH_2)_m$—, wherein n is an integer from 1 to 6;

m is 0 or an integer from 1 to 6;

y is 0 or 1; and

Z is O, NH, —O—P(O)(OH)—O—, S, S(O), $SO_2$ or —O—S(O)$_2$—O—.

In certain embodiments, n is an integer from 1 to 6, such as 1, 2, 3, 4, 5 or 6.

In certain embodiments, m is 0 or an integer from 1 to 6. In certain embodiments, m is 0, and thus the $-(CH_2)_m-$ portion of the linking group is not present. In certain embodiments, m is an integer from 1 to 6, such as 1, 2, 3, 4, 5 or 6.

In certain embodiments, y is 0 or 1. In certain embodiments, y is 0, and thus Z is not present. In certain embodiments, y is 1, and thus Z is present.

In certain embodiments, Z is O, NH, $-O-P(O)(OH)-O-$, S, S(O), $SO_2$ or $-O-S(O)_2-O-$. In certain embodiments, Z is O. In certain embodiments, Z is NH. In certain embodiments, Z is $-O-P(O)(OH)-O-$. In certain embodiments, Z is S. In certain embodiments, Z is S(O). In certain embodiments, Z is $SO_2$. In certain embodiments, Z is $-O-S(O)_2-O-$.

In certain embodiments, n is 1, m is 0 and y is 0. In certain embodiments, n is 2, m is 0 and y is 0. In certain embodiments, n is 3, m is 0 and y is 0. In certain embodiments, n is 4, m is 0 and y is 0. In certain embodiments, n is 5, m is 0 and y is 0. In certain embodiments, n is 6, m is 0 and y is 0.

In certain embodiments, n is 1, m is 1, y is 1 and Z is O. In certain embodiments, n is 2, m is 2, y is 1 and Z is O. In certain embodiments, n is 1, m is 1, y is 1 and Z is NH. In certain embodiments, n is 2, m is 2, y is 1 and Z is NH. In certain embodiments, n is 1, m is 1, y is 1 and Z is $-O-P(O)(OH)-O-$. In certain embodiments, n is 2, m is 2, y is 1 and Z is $-O-P(O)(OH)-O-$. In certain embodiments, n is 1, m is 1, y is 1 and Z is S. In certain embodiments, n is 2, m is 2, y is 1 and Z is S. In certain embodiments, n is 1, m is 1, y is 1 and Z is S(O). In certain embodiments, n is 2, m is 2, y is 1 and Z is S(O). In certain embodiments, n is 1, m is 1, y is 1 and Z is $SO_2$. In certain embodiments, n is 2, m is 2, y is 1 and Z is $SO_2$. In certain embodiments, n is 1, m is 1, y is 1 and Z is $-O-S(O)_2-O-$. In certain embodiments, n is 2, m is 2, y is 1 and Z is $-O-S(O)_2-O-$.

In certain embodiments, n is 1, m is 1, and y is 1. As such, in certain embodiments, the compound has the formula:

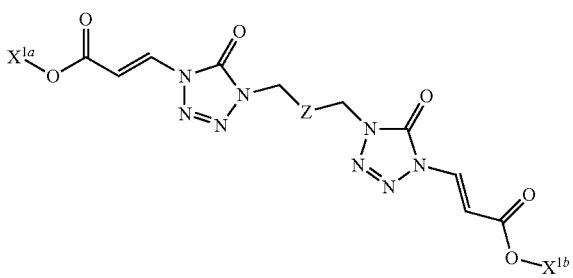

wherein $X^{1a}$ and $X^{1b}$ are each independently selected from H, $C_{1-6}$ alkyl and a progroup; and Z is O, NH, $-O-P(O)(OH)-O-$, S, S(O), $SO_2$ or $-O-S(O)_2-O-$, or a salt or stereoisomer thereof.

In certain embodiments, the compound has the formula:

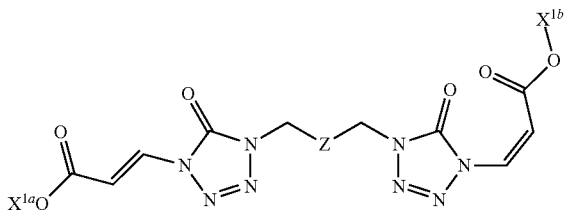

wherein $X^{1a}$ and $X^{1b}$ are each independently selected from H, $C_{1-6}$ alkyl and a progroup; and Z is O, NH, $-O-P(O)(OH)-O-$, S, S(O), $SO_2$ or $-O-S(O)_2-O-$, or a salt or stereoisomer thereof.

In certain embodiments, the compound has the formula:

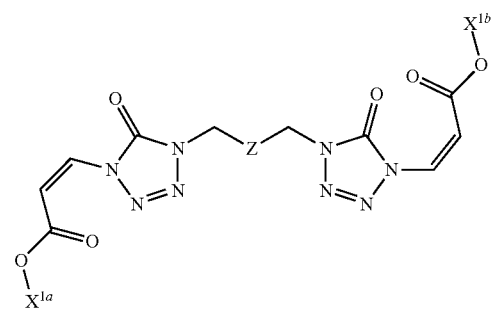

wherein $X^{1a}$ and $X^{1b}$ are each independently selected from H, $C_{1-6}$ alkyl and a progroup; and Z is O, NH, $-O-P(O)(OH)-O-$, S, S(O), $SO_2$ or $-O-S(O)_2-O-$, or a salt or stereoisomer thereof.

In certain embodiments, n is 2, m is 2, and y is 1. As such, in certain embodiments, the compound has the formula:

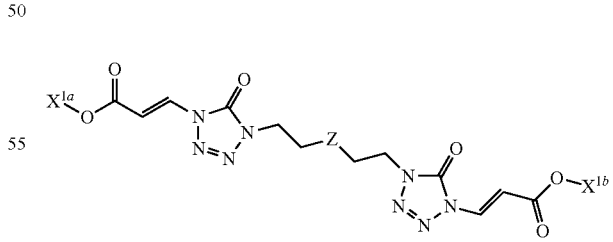

wherein $X^{1a}$ and $X^{1b}$ are each independently selected from H, $C_{1-6}$ alkyl and a progroup; and Z is O, NH, $-O-P(O)(OH)-O-$, S, S(O) $SO_2$ or $-O-S(O)_2-O-$, or a salt or stereoisomer thereof.

In certain embodiments, the compound has the formula:

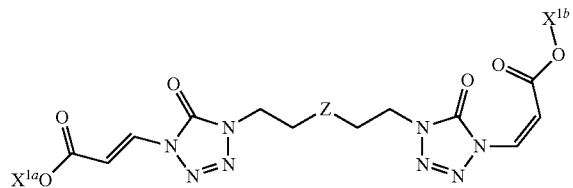

wherein
$X^{1a}$ and $X^{1b}$ are each independently selected from H, $C_{1-6}$ alkyl and a progroup; and
Z is O, NH, —O—P(O)(OH)—O—, S, S(O) $SO_2$ or —O—S(O)$_2$—O—,
or a salt or stereoisomer thereof.

In certain embodiments, the compound has the formula:

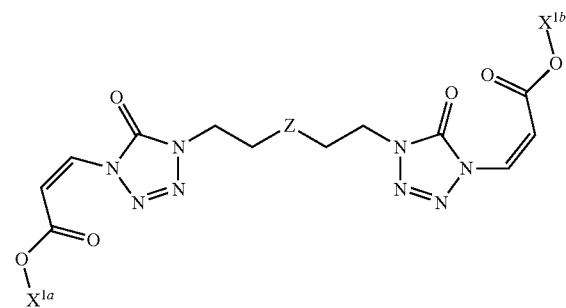

wherein
$X^{1a}$ and $X^{1b}$ are each independently selected from H, $C_{1-6}$ alkyl and a progroup; and
Z is O, NH, —O—P(O)(OH)—O—, S, S(O) $SO_2$ or —O—S(O)$_2$—O—,
or a salt or stereoisomer thereof.

In certain embodiments, n is 1, m is 1 and y is 1. In one such embodiment, Z is a phosphate ester and the compound has the formula:

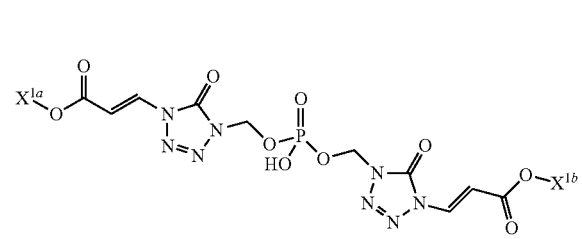

or a salt thereof, and wherein $X^{1a}$ and $X^{1b}$ are each independently selected from H, $C_{1-6}$ alkyl and a progroup.

In certain embodiments, $X^{1a}$ and $X^{1b}$ are each independently selected from H, $C_{1-6}$ alkyl and a progroup. In certain embodiments, $X^{1a}$ and $X^{1b}$ are each H. In certain embodiments, one of $X^{1a}$ and $X^{1b}$ is H, and the other is $C_{1-6}$ alkyl or a progroup. In certain embodiments, $X^{1a}$ and $X^{1b}$ are each $C_{1-6}$ alkyl. In these embodiments, the $C_{1-6}$ alkyl groups for $X^{1a}$ and $X^{1b}$ may be the same or different. In certain embodiments, $X^{1a}$ and $X^{1b}$ are each a progroup. In these embodiments, the progroups for $X^{1a}$ and $X^{1b}$ may be the same or different. In certain embodiments, $X^{1a}$ is $C_{1-6}$ alkyl and $X^{1b}$ is a progroup. In certain embodiments, $X^{1a}$ is a progroup and $X^{1b}$ is $C_{1-6}$ alkyl. The progroup for $X^{1a}$ and $X^{1b}$ are described in more detail above. For example, the progroup for $X^{1a}$ and $X^{1b}$ may each independently be $X^1$ as described in more detail above.

In certain embodiments, Z is O, NH, —O—P(O)(OH)—O—, S, S(O), $SO_2$ or —O—S(O)$_2$—O—. In certain embodiments, Z is O. In certain embodiments, Z is NH. In certain embodiments, Z is —O—P(O)(OH)—O—. In certain embodiments, Z is S. In certain embodiments, Z is S(O). In certain embodiments, Z is $SO_2$. In certain embodiments, Z is —O—S(O)$_2$—O—.

In certain embodiments, the compound of formula (IIa) is a dimer selected from the following compounds:

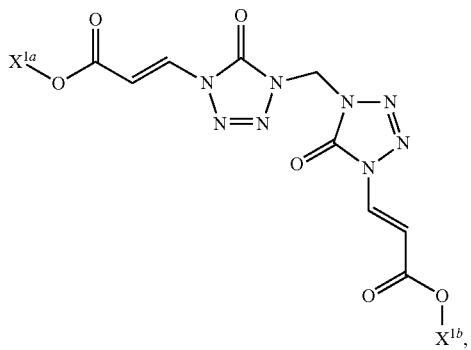

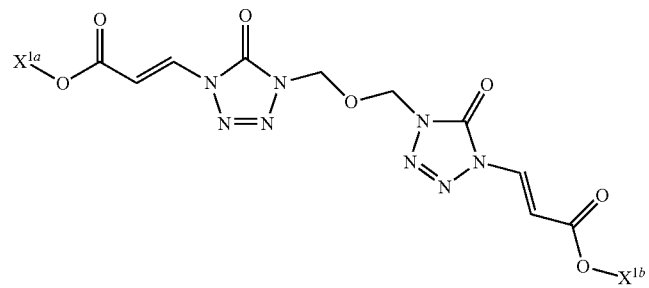

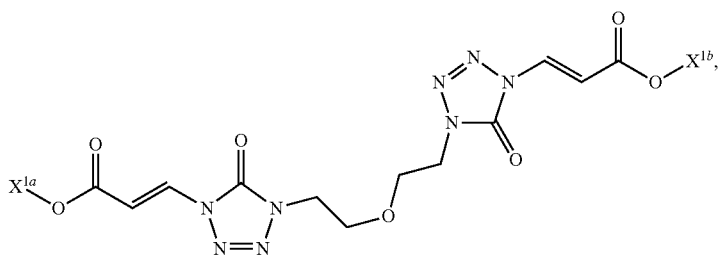

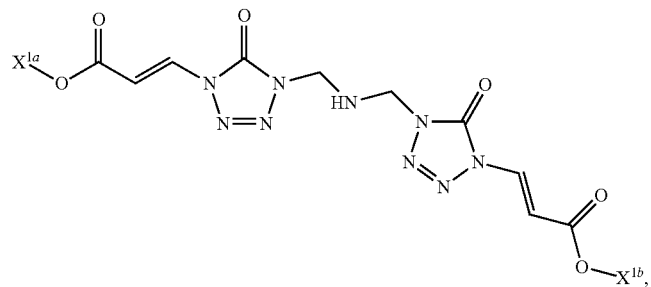
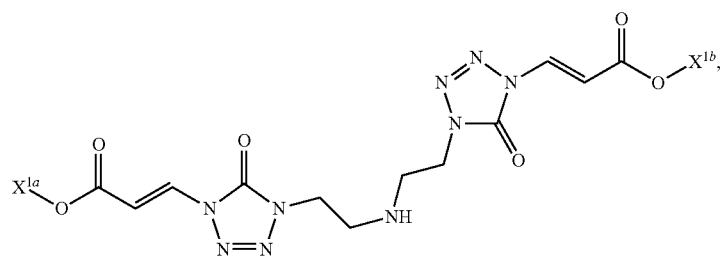
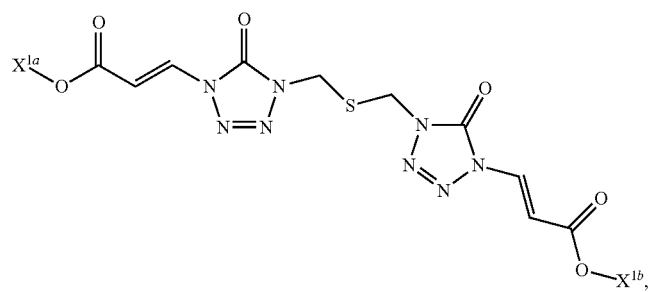
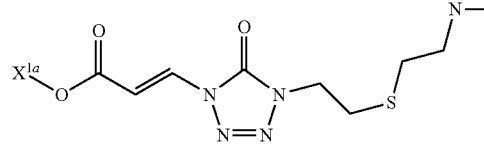
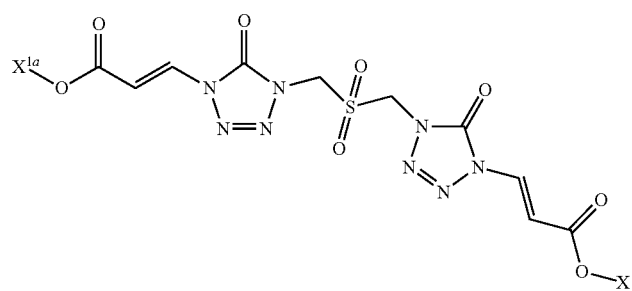
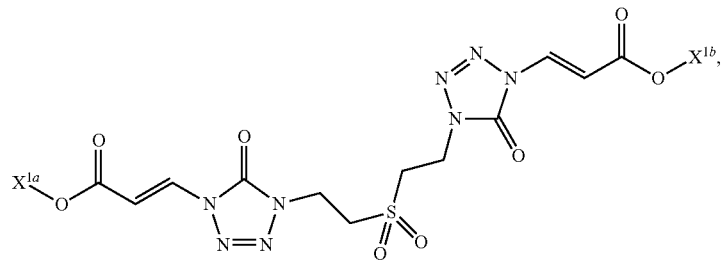

-continued

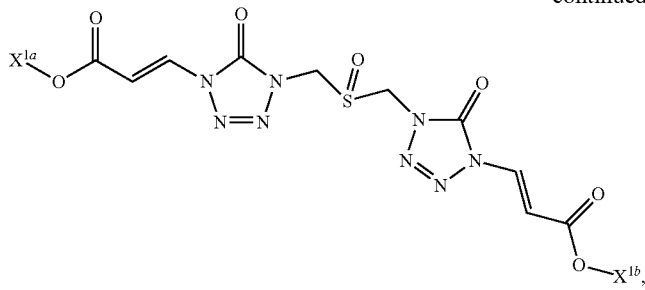

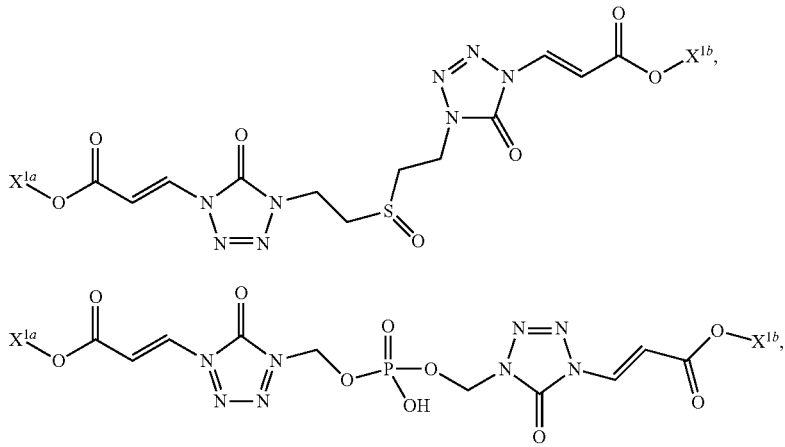

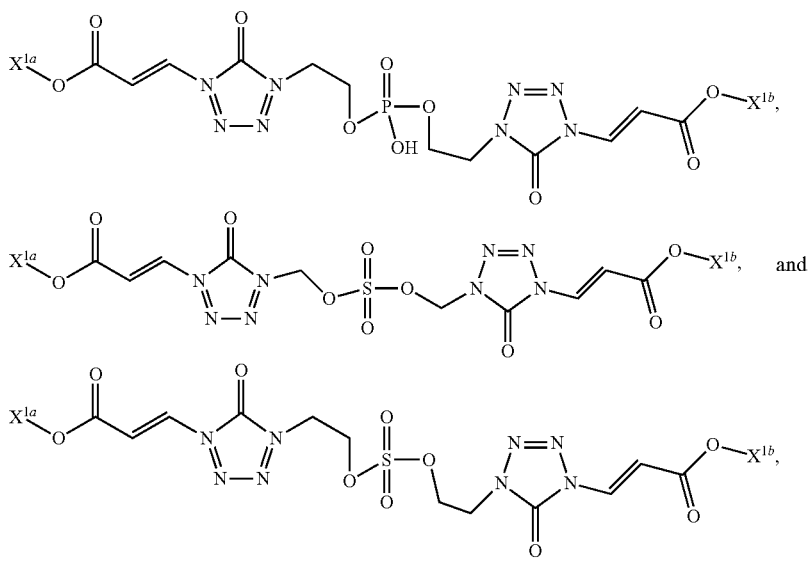

wherein $X^{1a}$ and $X^{1b}$ are as described above, or a salt or stereoisomer thereof.

For example, $X^{1a}$ and $X^{1b}$ may each be independently selected from H, $C_{1-6}$ alkyl and a progroup. In some instances, the progroup for $X^{1a}$ and $X^{1b}$ may each independently be $X^1$ as described in more detail above.

In certain embodiments, the linking group connecting the two compounds of formula II in a dimer may be a cleavable linking group. In some instances, cleavage of the linking group in the dimer releases the active agent moieties (e.g., two pharmaceutically active compounds). For example, a cleavable linking group may be cleaved by hydrolysis of one or more bonds in the linking group that connect the first compound of formula (IIa) or (IIb) to the second compound of formula (IIa) or (IIb) in the dimer. In some embodiments, cleavage of the cleavable linking group may occur in vivo, for instance in the gastrointestinal tract (e.g., stomach, small intestine, large intestine, etc.), or a desired site of action of the compound. In certain cases, compounds that include a cleavable linking group may facilitate delivery of the pharmaceutically active forms of the compound at a desired site of action, or after a desired amount of time after administration of the dimer (e.g., delayed release formulations, controlled release formulations, and the like).

Embodiments of the compounds of formulae (Ia), (Ib), (IIa) and (IIb) are shown in the following tables.

TABLE 1

| Compound | X¹ | R¹ |
|---|---|---|
| 1 | —CH₃ | H |
| 2 | —CH₃ | —CH₃ |
| 3 | H | H |
| 4 | H | —CH₃ |
| 5 | —CH₃ | —CH₂CH₃ |
| 6 | —CH₃ | —CH(CH₃)₂ |
| 7 | —CH₃ | (3-methyloxetan-3-yl)methyl |
| 8 | —CH₃ | —CH₂C(O)NH₂ |
| 9 | —CH₃ | —CH₂OCH₃ |
| 10 | —CH₃ | —C(O)N(CH₃)₂ |
| 11 | —CH₃ | -cyclopentyl |
| 12 | —CH₃ | 4-tetrahydropyranyl |
| 13 | —CH₃ | —CH₂CH₂OCH₃ |
| 14 | —CH₃ | —CH₂C(O)OCH₃ |
| 15 | -tert-butyl | —CH₃ |
| 16 | —CH₃ | phenyl |
| 17 | —CH₃ | 3-pyridyl |
| 18 | 2-(2,5-dioxopyrrolidin-1-yl)ethyl | —CH₃ |
| 19 | —CH₃ | —CH₂C(CH₃)₂OH |
| 20 | —CH₃ | (E)-4-methoxy-4-oxobut-2-en-1-yl |
| 21 | —CH₃ | cyclopropyl |
| 24 | —CH₃ | —CD₃ |
| 25 | —CH₃ | —CD(CD₃)₂ |
| 26 | —CH₃ | —CH₂CH₂N(CH₃)₂ |

TABLE 2

| Compound | X¹ | R¹ |
|---|---|---|
| 22 | —CH₃ | —CH₂CH₃ |
| 23 | tert-butyl | —CH₃ |

Particular compounds disclosed herein, and salts or solvates or stereoisomers thereof, include: Compound 1: methyl (E)-3-(5-oxo-4,5-dihydro-1H-tetrazol-1-yl)acrylate; Compound 2: methyl (E)-3-(4-methyl-5-oxo-4,5-dihydro-1H-tetrazol-1-yl)acrylate; Compound 3: (E)-3-(5-oxo-4,5-dihydro-1H-tetrazol-1-yl)acrylic acid; Compound 4: (E)-3-(4-methyl-5-oxo-4,5-dihydro-1H-tetrazol-1-yl)acrylic acid; Compound 5: methyl (E)-3-(4-ethyl-5-oxo-4,5-dihydro-1H-tetrazol-1-yl)acrylate; Compound 6: methyl (E)-3-(4-isopropyl-5-oxo-4,5-dihydro-1H-tetrazol-1-yl)acrylate; Compound 7: methyl (E)-3-(4-((3-methyloxetan-3-yl)methyl)-5-oxo-4,5-dihydro-1H-tetrazol-1-yl)acrylate; Compound 8: methyl (E)-3-(4-(2-amino-2-oxoethyl)-5-oxo-4,5-dihydro-1H-tetrazol-1-yl)acrylate; Compound 9: methyl (E)-3-(4-(methoxymethyl)-5-oxo-4,5-dihydro-1H-tetrazol-1-yl)acrylate; Compound 10: Preparation of Methyl (E)-3-(4-(dimethylcarbamoyl)-5-oxo-4,5-dihydro-1H-tetrazol-1-yl)acrylate; Compound 11: methyl (E)-3-(4-cyclopentyl-5-oxo-4,5-dihydro-1H-tetrazol-1-yl)acrylate; Compound 12: methyl (E)-3-(5-oxo-4-(tetrahydro-2H-pyran-4-yl)-4,5-dihydro-1H-tetrazol-1-yl)acrylate; Compound 13: methyl (E)-3-(4-(2-methoxyethyl)-5-oxo-4,5-dihydro-1H-tetrazol-1-yl)acrylate; Compound 14: methyl (E)-3-(4-(2-methoxy-2-oxoethyl)-5-oxo-4,5-dihydro-1H-tetrazol-1-yl)acrylate; Compound 15: tert-butyl (E)-3-(4-methyl-5-oxo-4,5-dihydro-1H-tetrazol-1-yl)acrylate; Compound 16: methyl (E)-3-(5-oxo-4-phenyl-4,5-dihydro-1H-tetrazol-1-yl)acrylate; Compound 17: methyl (E)-3-(5-oxo-4-(pyridin-3-yl)-4,5-dihydro-1H-tetrazol-1-yl)acrylate; Compound 18: 2-(2,5-dioxopyrrolidin-1-yl)ethyl (E)-3-(4-methyl-5-oxo-4,5-dihydro-1H-tetrazol-1-yl)acrylate; Compound 19: methyl (E)-3-(4-(2-hydroxy-2-methylpropyl)-5-oxo-4,5-dihydro-1H-tetrazol-1-yl)acrylate; Compound 20: dimethyl 3,3'-(5-oxo-1H-tetrazole-1,4(5H)-diyl)(2E,2'E)-diacrylate; Compound 21: methyl (E)-3-(4-cyclopropyl-5-oxo-4,5-dihydro-1H-tetrazol-1-yl)acrylate; Compound 22: methyl (Z)-3-(4-ethyl-5-oxo-4,5-dihydro-1H-tetrazol-1-yl)acrylate; Compound 23: tert-butyl (Z)-3-(4-methyl-5-oxo-4,5-dihydro-1H-tetrazol-1-yl)acrylate; Compound 24: methyl (E)-3-(4-deuteriomethyl-5-oxo-4,5-dihydro-1H-tetrazol-1-yl)acrylate; Compound 25: methyl (E)-3-(4-deuterioisopropyl-5-oxo-4,5-dihydro-1H-tetrazol-1-yl)acrylate and Compound 26: methyl (E)-3-(4-(2-(dimethylamino)ethyl)-5-oxo-4,5-dihydro-1H-tetrazol-1-yl)acrylate.

In certain embodiments, the compound has the structure:

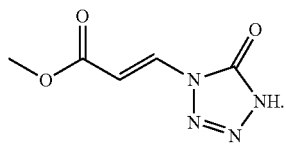

In certain embodiments, the compound has the structure:

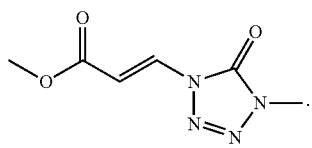

In certain embodiments, the compound has the structure:

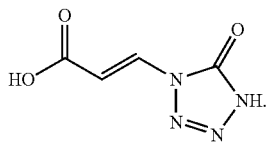

In certain embodiments, the compound has the structure:

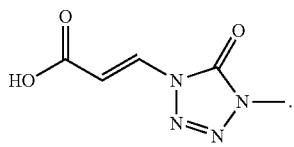

In certain embodiments, the compound has the structure:

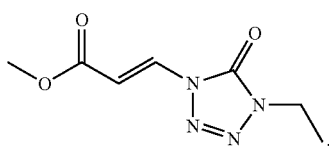

In certain embodiments, the compound has the structure:

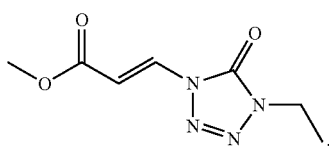

In certain embodiments, the compound has the structure:

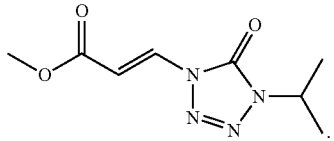

In certain embodiments, the compound has the structure:

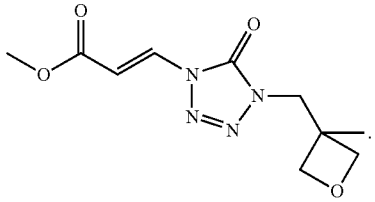

In certain embodiments, the compound has the structure:

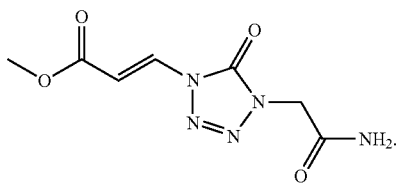 [SMILES: COC(=O)/C=C/n1nnn(CC(N)=O)c1=O]

In certain embodiments, the compound has the structure:

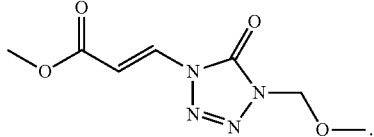

In certain embodiments, the compound has the structure:

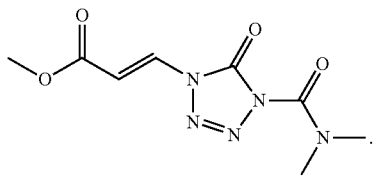

In certain embodiments, the compound has the structure:

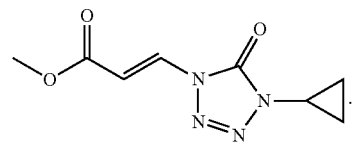

In certain embodiments, the compound has the structure:

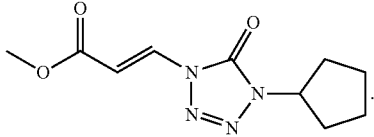 [SMILES: COC(=O)/C=C/n1nnn(C2CCCC2)c1=O]

In certain embodiments, the compound has the structure:

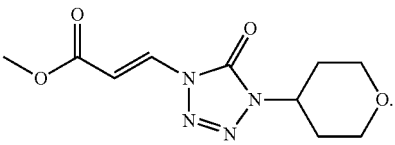 [SMILES: COC(=O)/C=C/n1nnn(C2CCOCC2)c1=O]

In certain embodiments, the compound has the structure:

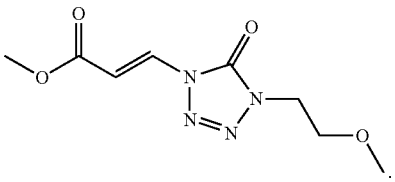

In certain embodiments, the compound has the structure:

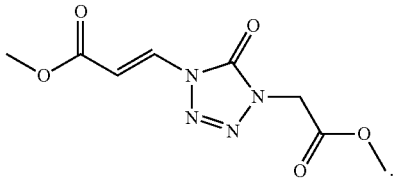

In certain embodiments, the compound has the structure:

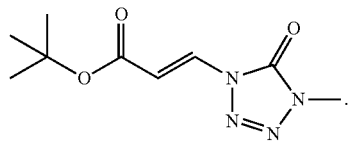 [SMILES: Cn1nnn(/C=C/C(=O)OC(C)(C)C)c1=O]

In certain embodiments, the compound has the structure:

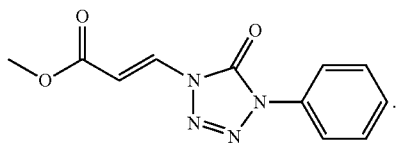 [SMILES: COC(=O)/C=C/n1nnn(-c2ccccc2)c1=O]

In certain embodiments, the compound has the structure:

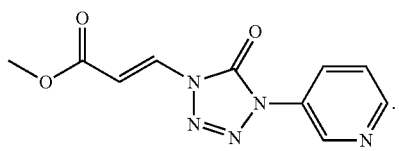 [SMILES: COC(=O)/C=C/n1nnn(-c2cccnc2)c1=O]

In certain embodiments, the compound has the structure:

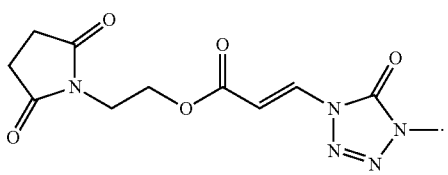

In certain embodiments, the compound has the structure:

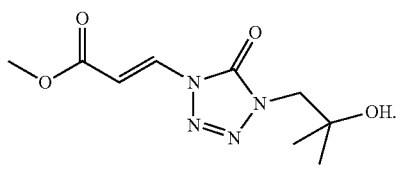 [SMILES: COC(=O)/C=C/n1nnn(CC(C)(C)O)c1=O]

In certain embodiments, the compound has the structure:

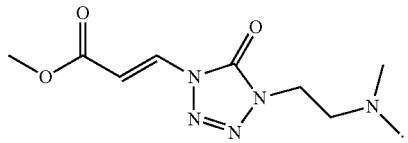

In certain embodiments, the compound has the structure:

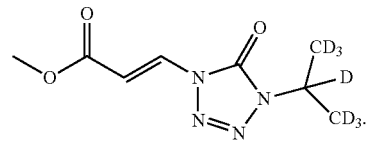 [SMILES: [2H]C([2H])([2H])C([2H])(n1nnn(/C=C/C(=O)OC)c1=O)C([2H])([2H])[2H]]

In certain embodiments, the compound has the structure:

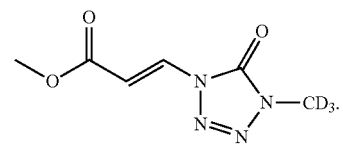 [SMILES: [2H]C([2H])([2H])n1nnn(/C=C/C(=O)OC)c1=O]

In certain embodiments, the compound has the structure:

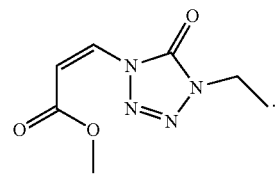

In certain embodiments, the compound has the structure:

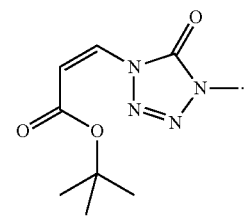

The compounds described also include isotopically labeled compounds where one or more atoms have an atomic mass different from the atomic mass conventionally found in nature. Examples of isotopes that may be incorporated into the compounds disclosed herein include, but are not limited to, $^{2}H$, $^{3}H$, $^{11}C$, $^{13}C$, $^{14}C$, $^{15}N$, $^{18}O$, $^{17}O$, etc. Thus, the disclosed compounds may be enriched in one or more of these isotopes relative to the natural abundance of such isotope. By way of example, deuterium ($^{2}H$; D) has a natural abundance of about 0.015%. Accordingly, for approximately every 6,500 hydrogen atoms occurring in nature, there is one deuterium atom. Specifically contemplated herein are compounds enriched in deuterium at one or more positions. Thus, deuterium containing compounds of the disclosure have deuterium at one or more positions (as the case may be) in an abundance of greater than 0.015%. In some embodiments, one or more (e.g., 1, 2, 3, 4, 5, 6, 7 or more) hydrogen atoms of an $R^1$ group of any one of the subject compounds described herein are substituted with a deuterium.

Pharmaceutical Compositions

In certain embodiments, the disclosed compounds are useful for the treatment of a disease or disorder, such as an autoimmune or an inflammatory disease or disorder. Accordingly, pharmaceutical compositions comprising at least one disclosed compound are also described herein. For example, the present disclosure provides pharmaceutical compositions that include a pharmaceutically acceptable carrier and a therapeutically effective amount of a compound of the present disclosure or a pharmaceutically acceptable salt or solvate or stereoisomer thereof.

A pharmaceutical composition that includes a subject compound may be administered to a patient alone, or in combination with other supplementary active agents. For example, one or more compounds according to formula I or formula II can be administered to a patient with or without supplementary active agents. By way of example supplementary active agents include dimethyl fumarate and monomethylfumarate and salts thereof. The pharmaceutical compositions may be manufactured using any of a variety of processes, including, but not limited to, conventional mixing, dissolving, granulating, dragee-making, levigating, emulsifying, encapsulating, entrapping, lyophilizing, and the like. The pharmaceutical composition can take any of a variety of forms including, but not limited to, a sterile solution, suspension, emulsion, spray dried dispersion, lyophilisate, tablet, microtablets, pill, pellet, capsule, powder, syrup, elixir or any other dosage form suitable for administration.

A subject compound may be administered to a subject using any convenient means capable of resulting in the desired reduction in disease condition or symptom. Thus, a subject compound can be incorporated into a variety of formulations for therapeutic administration. More particularly, a subject compound can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, aerosols, and the like.

Formulations for pharmaceutical compositions are described in, for example, Remington's Pharmaceutical Sciences, by E. W. Martin, Mack Publishing Co., Easton, Pa., 19th Edition, 1995, which describes examples of formulations (and components thereof) suitable for pharmaceutical delivery of disclosed compounds. Pharmaceutical compositions that include at least one of the subject compounds can be formulated for use in human or veterinary medicine. Particular formulations of a disclosed pharmaceutical composition may depend, for example, on the mode of administration and/or on the location of the subject to be treated. In some embodiments, formulations include a pharmaceutically acceptable carrier in addition to at least one active ingredient, such as a subject compound. In other embodiments, other medicinal or pharmaceutical agents, for example, with similar, related or complementary effects on the disease or condition being treated can also be included as active ingredients in a pharmaceutical composition.

Pharmaceutically acceptable carriers useful for the disclosed methods and compositions may depend on the particular mode of administration being employed. For example, parenteral formulations may include injectable fluids, such as, but not limited to, pharmaceutically and physiologically acceptable fluids such as water, physiological saline, balanced salt solutions, aqueous dextrose, glycerol or the like as a vehicle. For solid compositions (e.g., powder, pill, tablet, or capsule forms), non-toxic solid carriers can include, for example, pharmaceutical grades of mannitol, lactose, starch, or magnesium stearate. In addition to biologically neutral carriers, pharmaceutical compositions to be administered can optionally contain minor amounts of non-toxic auxiliary substances (e.g., excipients), such as wetting or emulsifying agents, preservatives, and pH buffering agents and the like; for example, sodium acetate or sorbitan monolaurate. Other examples of excipients include, nonionic solubilizers, such as cremophor, or proteins, such as human serum albumin or plasma preparations.

Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) water (e.g., pyrogen-free water); (17) isotonic saline; (18) Ringer's solution; (19) ethyl alcohol; (20) pH buffered solutions; (21) polyesters, polycarbonates and/or polyanhydrides; and (22) other non-toxic compatible substances employed in pharmaceutical formulations.

The disclosed pharmaceutical compositions may be formulated as a pharmaceutically acceptable salt of a disclosed compound. Examples of pharmaceutically acceptable salts include non-toxic salts of a free base form of a compound that possesses the desired pharmacological activity of the free base. These salts may be derived from inorganic or organic acids. Non-limiting examples of suitable inorganic acids are hydrochloric acid, nitric acid, hydrobromic acid, sulfuric acid, hydroiodic acid, and phosphoric acid. Non-limiting examples of suitable organic acids are acetic acid, propionic acid, glycolic acid, lactic acid, pyruvic acid, malonic acid, succinic acid, malic acid, maleic acid, fumaric acid, tartaric acid, citric acid, benzoic acid, cinnamic acid, mandelic acid, methanesulfonic acid, ethanesulfonic acid, methyl sulfonic acid, salicylic acid, formic acid, trichloroacetic acid, trifluoroacetic acid, gluconic acid, asparagic acid, aspartic acid, benzenesulfonic acid, para-toluenesulfonic acid, naphthalenesulfonic acid, combinations thereof, and the like. In certain embodiments, the pharmaceutically acceptable salt includes formic acid. Other examples of pharmaceutically acceptable salts include non-toxic salts of a free acid form of compounds according to formula I or formula II. Such salts are derived from inorganic or organic bases. Pharmaceutically acceptable base addition salts include those derived from inorganic bases such as sodium, potassium, lithium, ammonium, calcium, magnesium, iron, zinc, copper, manganese, aluminum salts, combinations thereof, and the like. Examples of salts are the ammonium, potassium, sodium, calcium, and magnesium salts. Salts of the presently disclosed compounds can be derived from pharmaceutically acceptable organic non-toxic bases including, but not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, 2-amino-2-hydroxymethyl-propane-1,3-diol ("Tris" salt), dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, combinations thereof, and the like. Pharmaceutically acceptable salts are described further in S. M. Berge, et al., "Pharmaceutical Salts," J. Pharm. Sci., 1977; 66:1-19 and Remington's Pharmaceutical Sciences, 19th Edition, Mack Publishing Company, Easton, Pa., 1995.

A subject compound can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents. Such preparations can be used for oral administration.

A subject compound can be formulated into preparations for injection by dissolving, suspending or emulsifying the compound in an aqueous or nonaqueous solvent, such as vegetable or other similar oils, synthetic aliphatic acid glycerides, esters of higher aliphatic acids or propylene glycol; and if desired, with conventional additives such as solubilizers, isotonic agents, suspending agents, emulsifying agents, stabilizers and preservatives. The preparation may also be emulsified or the active ingredient encapsulated in liposome vehicles. Formulations suitable for injection can be administered by an intravitreal, intraocular, intramuscular, subcutaneous, sublingual, or other route of administration, e.g., injection into the gum tissue or other oral tissue. Such formulations are also suitable for topical administration.

In some embodiments, a subject compound can be delivered by a continuous delivery system. The term "continuous delivery system" is used interchangeably herein with "controlled delivery system" and encompasses continuous (e.g., controlled) delivery devices (e.g., pumps) in combination with catheters, injection devices, and the like, a wide variety of which are known in the art.

A subject compound can be utilized in aerosol formulation to be administered via inhalation. A subject compound can be formulated into pressurized acceptable propellants such as dichlorodifluoromethane, propane, nitrogen and the like.

Furthermore, a subject compound can be made into suppositories by mixing with a variety of bases such as emulsifying bases or water-soluble bases. A subject compound can be administered rectally via a suppository. The suppository can include vehicles such as cocoa butter, carbowaxes and polyethylene glycols, which melt at body temperature, yet are substantially solid at room temperature.

The term "unit dosage form," as used herein, refers to physically discrete units suitable as unitary dosages for human and animal subjects, each unit containing a predetermined quantity of a subject compound calculated in an amount sufficient to produce the desired effect in association with a pharmaceutically acceptable diluent, carrier or vehicle. The specifications for a subject compound depend on the particular compound employed and the effect to be achieved, and the pharmacodynamics associated with each compound in the host.

The dosage form of a disclosed pharmaceutical composition may be determined by the mode of administration chosen. For example, in addition to injectable fluids, topical or oral dosage forms may be employed. Topical preparations may include eye drops, ointments, sprays and the like. Oral formulations may be liquid (e.g., syrups, solutions or suspensions), or solid (e.g., powders, pills, tablets, or capsules). Methods of preparing such dosage forms are known, or will be apparent, to those skilled in the art.

Certain embodiments of the pharmaceutical compositions that include a subject compound may be formulated in unit dosage form suitable for individual administration of precise dosages. The amount of active ingredient administered may depend on the subject being treated, the severity of the affliction, and the manner of administration, and is known to those skilled in the art. In certain instances, the formulation to be administered contains a quantity of the compounds disclosed herein in an amount effective to achieve the desired effect in the subject being treated.

Each therapeutic compound can independently be in any dosage form, such as those described herein, and can also be administered in various ways, as described herein. For example, the compounds may be formulated together, in a single dosage unit (that is, combined together in one form such as capsule, tablet, powder, or liquid, etc.) as a combination product. Alternatively, when not formulated together in a single dosage unit, an individual subject compound may be administered at the same time as another therapeutic compound or sequentially, in any order thereof.

A disclosed compound can be administered alone, as the sole active pharmaceutical agent, or in combination with one or more additional compounds of the present disclosure or in conjunction with other agents. When administered as a combination, the therapeutic agents can be formulated as separate compositions that are administered simultaneously or at different times, or the therapeutic agents can be administered together as a single composition combining two or more therapeutic agents. Thus, the pharmaceutical compositions disclosed herein containing a compound of the present disclosure optionally include other therapeutic agents. Accordingly, certain embodiments are directed to such pharmaceutical compositions, where the composition further includes a therapeutically effective amount of an agent selected as is known to those of skill in the art.

Methods of Administration

The subject compounds find use for treating a disease or disorder in a subject, such as an autoimmue or an inflammatory disease or disorder. The route of administration may be selected according to a variety of factors including, but not limited to, the condition to be treated, the formulation and/or device used, the patient to be treated, and the like. Routes of administration useful in the disclosed methods include but are not limited to oral and parenteral routes, such as intravenous (iv), intraperitoneal (ip), rectal, topical, ophthalmic, nasal, and transdermal. Formulations for these dosage forms are described herein.

An effective amount of a subject compound may depend, at least, on the particular method of use, the subject being treated, the severity of the affliction, and the manner of administration of the therapeutic composition. A "therapeutically effective amount" of a composition is a quantity of a specified compound sufficient to achieve a desired effect in a subject (e.g., patient) being treated. For example, this may be the amount of a subject compound necessary to prevent, inhibit, reduce or relieve a disease or disorder in a subject, such as an autoimmue or an inflammatory disease or disorder. Ideally, a therapeutically effective amount of a compound is an amount sufficient to prevent, inhibit, reduce or relieve a disease or disorder in a subject without causing a substantial cytotoxic effect on host cells in the subject.

Therapeutically effective doses of a subject compound or pharmaceutical composition can be determined by one of skill in the art, with a goal of achieving local (e.g., tissue) concentrations that are at least as high as the $EC_{50}$ of an applicable compound disclosed herein.

An example of a dosage range is from 0.1 to 200 mg/kg body weight orally in single or divided doses. In some embodiments, a dosage range is from 1.0 to 100 mg/kg body weight orally in single or divided doses, including from 1.0 to 50 mg/kg body weight, from 1.0 to 25 mg/kg body weight, from 1.0 to 10 mg/kg body weight (assuming an average body weight of approximately 70 kg; values may be adjusted accordingly for persons weighing more or less than average). For oral administration, the compositions are, for example, provided in the form of a tablet containing from about 10 to about 1000 mg of the active ingredient, such as 25 to 750 mg, or 50 to 500 mg, for example 75 mg, 100 mg, 200 mg, 250 mg, 400 mg, 500 mg, 600 mg, 750 mg, or 1000 mg of the active ingredient for the symptomatic adjustment of the dosage to the subject being treated. In certain embodiments of an oral dosage regimen, a tablet containing from 500 mg to 1000 mg active ingredient is administered once (e.g., a loading dose) followed by administration of ½ (i.e., half) dosage tablets (e.g., from 250 to 500 mg) each 6 to 24 hours for 3 days or more.

The specific dose level and frequency of dosage for any particular subject may be varied and may depend upon a variety of factors, including the activity of the subject compound, the metabolic stability and length of action of that compound, the age, body weight, general health, sex and diet of the subject, mode and time of administration, rate of excretion, drug combination, and severity of the condition of the host undergoing therapy.

Embodiments of the present disclosure also include combinations of one or more disclosed compounds with one or more other agents or therapies useful in the treatment of a disease or disorder. In certain instances, the disease or disorder is an autoimmune or an inflammatory disease or disorder. In certain instances, the disease or disorder is psoriasis, such as plaque psoriasis. In certain instances, the disease or disorder is multiple sclerosis. For example, one or more disclosed compounds may be administered in combination with therapeutically effective doses of other medicinal and pharmaceutical agents, or in combination other non-medicinal therapies, such as hormone (e.g., corticosteroids) or radiation therapy (e.g., phototherapy). The term "administration in combination with" refers to both concurrent and sequential administration of the active agents.

Methods of Treatment

The subject compounds are useful for treating a disease or disorder, such as an autoimmue or an inflammatory disease or disorder, in a subject in need of treatment. In certain instances, the disease or disorder is an autoimmue or an inflammatory disease or disorder. In certain instances, the disease or disorder is psoriasis, such as plaque psoriasis. In certain instances, the disease or disorder is multiple sclerosis. Other diseases that can be treated with the compounds disclosed herein include pulmonary arterial hypertension (PAH), non-alcoholic and alcoholic steatohepatitis, traumatic brain injury, radiation exposure and exposure to toxic chemicals such as cyanide.

Accordingly, the present disclosure provides methods of treating an inflammatory disease in a subject by administering an effective amount of a subject compound, including a salt or solvate or stereoisomer thereof, so as to treat inflammation. For example, the present disclosure provides a method of treating an inflammatory disease in a subject. In certain embodiments, the method includes administering to the subject (e.g., patient) a compound of the present disclosure, or a salt or solvate or stereoisomer thereof.

In addition, the present disclosure also provides methods of treating an autoimmune disease in a subject by administering to the subject an effective amount of a subject compound, including a salt or solvate or stereoisomer thereof, so as to treat the autoimmune disease. For example, the present disclosure also provides a method of treating an autoimmune disease in a subject. In certain embodiments, the method includes administering to the subject (e.g., patient) a compound of the present disclosure, or a salt or solvate or stereoisomer thereof.

In some embodiments, the subject compounds are resistant to degradation in vivo. In certain embodiments, the subject compound is stable in vivo. In certain instances, the compound includes an $R^1$ group (e.g., as described herein) that is attached to a core tetrazolone ring of the compound via a covalent bond that is not cleaved in vivo. In certain cases, the subject compound has an extended in vivo half life, e.g., a half life of 4 hours or more, such as 6 hours or more, 8 hours or more, 12 hours or more, 1 day or more, 2 days or more, 3 days or more, 4 days or more, 5 days or more, 6 days or more, 1 week or more, 2 weeks or more, 4 weeks or more, or even more. As used herein, the term "in vivo half life" refers to the time that it takes for the concentration in blood plasma of a substance of interest to reach one-half of its steady-state value.

Diseases or conditions for treatment according to the present disclosure include, but are not limited to, psoriasis, multiple sclerosis, inflammatory bowel disease, asthma, chronic obstructive pulmonary disease, and arthritis. For example, diseases or conditions for treatment according to the present disclosure include, but are not limited to, immunological, autoimmune, and/or inflammatory diseases including: psoriasis such as plaque psoriasis; asthma; chronic obstructive pulmonary diseases (COPD) such as bronchitis, emphysema, as well as other lung disorders such as asbestosis, pneumoconiosis, and pulmonary neoplasms; arthritis such as inflammatory arthritis, including rheumatoid arthritis, juvenile rheumatoid arthritis (juvenile idiopathic arthritis), psoriatic arthritis, and ankylosing spondylitis produce joint inflammation; cardiac insufficiency including left ventricular insufficiency, myocardial infarction and angina pectoris; mitochondrial and neurodegenerative diseases such as Parkinson's disease, Alzheimer's disease, Huntington's disease, amyotrophic lateral sclerosis (ALS or Lou Gehrig's Disease), retinopathia pigmentosa and mitochondrial encephalomyopathy; transplantation rejection; autoimmune diseases including multiple sclerosis, ischemia and reperfusion injury, AGE-induced genome damage; inflammatory bowel diseases (IBD) such as Crohn's disease and ulcerative colitis; and NF-κB mediated diseases.

Further diseases or conditions for treatment according to the present disclosure include, but are not limited to, rheumatica, granuloma annulare, lupus, autoimmune carditis, eczema, sarcoidosis, and autoimmune diseases including acute disseminated encephalomyelitis, Addison's disease, alopecia areata, ankylosing spondylitis, antiphospholipid antibody syndrome, autoimmune hemolytic anemia, autoimmune hepatitis, autoimmune inner ear disease, bullous pemphigoid, Behcet's disease, celiac disease, Chagas disease, chronic obstructive pulmonary disease, Crohn's disease, dermatomyositis, diabetes mellitus type I, endometriosis, Goodpasture's syndrome, Graves' disease, Guillain-Barre syndrome, Hashimoto's disease, hidradenitis suppurativea, Kawasaki disease, IgA neuropathy, idiopathic thrombocytopenic purpura, interstitial cystitis, lupus erythematosus, mixed connective tissue disease, morphea, multiple sclerosis, myasthenia gravis, narcolepsy, neuromyotonia, pemphigus vulgaris, pernicious anaemia, psoriasis, psonatic arthritis, polymyositis, primary biliary cirrhosis, rheumatoid arthritis, schizophrena, scleroderma, Sjogren's syndrome, stiff person syndrome, temporal arteritis, ulcerative colitis, vasculitis, vitiligo, and Wegener's granulomatosis.

Additional diseases or conditions for treatment according to the present disclosure include, but are not limited to, necrobiosis lipodica, granuloma annulare, sarcoidosis, alopecia areata, cheilitis granulomatosa, recurrent oral aphthae, non-infectious chronic uveitis, *pityriasis rubra* pilaris, annular elastolytic giant cell granuloma, and the like. Diseases or conditions for treatment according to the present disclosure also include Huntington's disease, malaria, HIV, HIV-associated neurodegenerative disorders, bronchial asthma, myocardial infarction, chronic obstructive pulmonary disease, HSV1 keratitis, and immunosuppression due to organ transplantation.

In certain embodiments, the subject compounds are useful for treating a disease or disorder, such as cell proliferative disorders. Cell proliferative disorders treatable with the subject compound disclosed herein relate to any disorder characterized by aberrant cell proliferation. These include various tumors and cancers, benign or malignant, metastatic or non-metastatic. Specific properties of cancers, such as tissue invasiveness or metastasis, can be targeted using the methods described herein. Cell proliferative disorders include a variety of cancers, including, among others, breast cancer, colon cancer, melanoma, glioblastoma, ovarian cancer, renal cancer, gastrointestinal cancer, kidney cancer, bladder cancer, pancreatic cancer, lung squamous carcinoma, and adenocarcinoma.

Compounds of the present disclosure may also find use as research tools. Accordingly, the present disclosure also provides for a method for using a compound of the present disclosure or a salt or solvate or stereoisomer thereof as a research tool for studying a biological system or sample, or for discovering new chemical compounds having use for treating a an autoimmue or an inflammatory disease or disorder in a subject.

Embodiments are also directed to a compound of the present disclosure or a salt or solvate or stereoisomer thereof, for use in therapy or as a medicament. For instance, embodiments include the use of a compound of the present disclosure or a salt or solvate or stereoisomer thereof, for the manufacture of a medicament; for example, for the manufacture of a medicament for the treatment of an autoimmune or inflammatory disease or disorder. In some cases, the embodiments are also directed to the use of a compound of the present disclosure or a salt or solvate or stereoisomer thereof for the manufacture of a medicament for the treatment of an autoimmune disease, such as multiple sclerosis. The embodiments are also directed to the use of a compound of the present disclosure or a salt or solvate or stereoisomer thereof for the manufacture of a medicament for the treatment of an inflammatory disease or disorder, such as psoriasis. Further diseases or conditions for treatment according to the present disclosure are discussed above.

Characterization of Functional Properties

The following are examples of assays useful in characterizing activities of a compound of the present disclosure.

A. In Vitro

1. Glutathione Depletion Assay

In one aspect the present compounds exert their therapeutic effects by acting as a Michael acceptor for reactive thiol groups in vivo. See, for example, Lehmann et al. Dimethyfumarate Induces Immunosuppression via Glutathione Depletion and Subsequent Induction of Heme Oxygenase 1, *Journal of Investigative Dermatology* (2007) 127, 835-845. Accordingly, the present compounds may be assessed in vitro by reaction with glutathione as follows:

A mixture of dimethylfumarate (5.2 mg, 3.6 mmol) and reduced glutathione (22.4 mg, 7.3 mmol; 2 equiv.) in $d_6$-DMSO (1.2 mL) were combined in a screw-top vial and the mixture was stirred at 35° C. (with the top securely fastened). Aliquots of sample were removed at intermittent timepoints and a $^1$H NMR taken [note: after analysis by $^1$H NMR, the sample can be returned to the heated vial and reaction continued). $^1$H NMR indicates majority reaction with glutathione (by Michael addition to the double bond) after 3 hr, and complete reaction by 27 hr.

The above reaction was repeated using monomethylfumarate (11.4 mg, 8.8 mmol) and reduced glutathione (55.5 mg, 18.0 mmol) in $d_6$-DMSO (3.0 mL) at 35° C. As judged by $^1$H NMR, majority reaction was observed by 27 hr.

The above reaction was repeated using methyl (E)-3-(5-oxo-4,5-dihydro-1H-tetrazol-1-yl)acrylate (6.2 mg, 3.6 mmol) and reduced glutathione (22.4 mg, 7.2 mmol) in $d_6$-DMSO (1.2 mL) at 35° C. As judged by $^1$H NMR, majority reaction was observed by 30 hr.

The above reaction was repeated using methyl (E)-3-(4-methyl-5-oxo-4,5-dihydro-1H-tetrazol-1-yl)acrylate (6.6 mg, 3.6 mmol) and reduced glutathione (22.4 mg, 7.2 mmol) in $d_6$-DMSO (1.2 mL) at 35° C. As judged by $^1$H NMR, majority reaction was observed by 30 hr.

In all the above cases, dis-appearance of the alkene proton signals from the starting material are used to determine the extent of Michael reaction with glutathione.

As would be understood by those of skill in the art, the above experiments can be repeated by varying the equivalents of reduced glutathione (0.5 to 2 equivalents); the reactions can also be run in a mixture of $d_6$-DMSO and $D_2O$; and the temperature of the reaction can also be varied from room temperature to 35° C. (35° C. being used to mimic body temperature). As used herein "majority reaction" means a greater than 50% reduction in alkene proton signal as observed by $^1$H NMR.

Other in vitro assays well known to those of skill in the art can be used to demonstrate the anti-inflammatory efficacy of the present compounds. For example, certain compounds blocked production of the inflammatory cytokine IL-23 in THP 1 cells stimulated with LPS.

B. In Vivo

1. Mouse Experimental Autoimmune Encephalomyelitis Assay

The in vivo efficacy of a compound towards autoimmune diseases can be demonstrated in a mouse model of experimental autoimmune encephalomyelitis (EAE).

Model Description:

EAE is a useful model for multiple sclerosis (MS), an autoimmune disease of the CNS that is caused by immune-cell infiltration of the CNS white matter. Inflammation and subsequent destruction of myelin cause progressive paralysis. Like the human disease, EAE is associated with peripheral activation of T cells autoreactive with myelin proteins, such as myelin basic protein (MBP), proteolipid protein (PLP), or myelin oligodendrocyte protein (MOG). Activated neuroantigen-specific T cells pass the blood-brain barrier, leading to focal mononuclear cell infiltration and demyelination. EAE can be induced in susceptible mouse strains by immunization with myelin-specific proteins in combination with adjuvant. In the SJL mouse model used in these studies, hind limb and tail paralysis is apparent by Day 10 after immunization, the peak of disease severity can be observed between Days 10 and 14, and a cycle of partial spontaneous remission followed by relapse can be observed up to Day 35. The results can demonstrate the potential of a compound to suppress disease severity and prevent relapse of disease symptoms that may be the result of FcγR-mediated cytokine release from immune cells.

Study Protocol:

In the SJL murine model of EAE, each mouse is sensitized with proteolipid protein (PLP)/complete Freund's adjuvant (CFA). (150 μg $PLP_{139-151}$ with 200 μg CFA in 0.05 ml of homogenate on four sites of hind flank for a total of 0.2 ml emulsion is used to induce EAE). In a suppression protocol, either vehicle or various doses of a test compound are administered via oral gavage starting on the day of immunization (Day 0). In a treatment protocol, at onset of disease, animals are separated to achieve groups with a similar mean clinical score at onset and administered vehicle or various dose frequencies of test compounds via oral gavage. In both protocols, clinical scores are monitored daily, and body weights are measured twice weekly.

Determination of Results:

By 10 days after PLP immunization, SJL mice can develop clinical EAE, as evidenced by an increase in their mean clinical scores. The paralytic score can gradually increase in the animals treated with vehicle only from the day of immunization (Day 0), and by Day 14 the mean score can reach a peak of about 5.1. At disease peak (e.g., Day 14), the mean clinical score in animals treated with either daily or twice daily can be significantly reduced. By Day 16, animals can exhibit a partial remission of mean clinical severity, which is a characteristic of the SJL model. The lower clinical scores in animals treated twice daily with a test compound can remain significant throughout the experiment until the animals are sacrificed on Day 30. These lower scores throughout the treatment period are reflected in the significantly lower cumulative disease index (CDI) and increase in cumulative weight index (CWI).

SJL mice treated with a test compound at disease onset (e.g., Day 11) can show a significant decrease in CDI. Further, there can be a decrease in the number of relapses in animals treated with a test compound compared with the number of relapses in animals treated with vehicle.

2. Experimental Autoimmune Encephalomyelitis Animal Model

The in vivo therapeutic efficacy of a compound for treating autoimmune diseases, such as multiple sclerosis, can be assessed in an experimental autoimmune encephalomyelitis (EAE) animal model.

Animals and EAE Induction:

Female C57BL/6 mice, 8-10 weeks old are immunized subcutaneously in the flanks and mid-scapular region with 200 μg of myelin oligodendrocyte glycoprotein peptide ($MOG_{35-55}$) emulsified (1:1 volume ratio) with complete Freund's adjuvant (CFA) (containing 4 mg/mL *Mycobacterium tuberculosis*). The emulsion is prepared by the syringe-extrusion method with two glass Luer-Lock syringes connected by a 3-way stopcock. Mice are also given an intraperitoneal injection of 200 ng pertussis toxin on the day of immunization and on day two post immunization. Mice are weighed and examined daily for clinical signs of experimental autoimmune encephalomyelitis (EAE). Food and water is provided ad libitum and once animals start to show disease, food is provided on the cage bottom.

Treatment Protocol:

Solutions containing various concentrations of a test compound are administered by oral gavage twice daily to different treatment groups starting from day 3 post-immunization until termination. Dexamethasone is dissolved in 1×PBS buffer (1 mg/kg) and administered subcutaneously once daily.

Clinical Evaluation:

Mice are scored daily beginning on day 7 post immunization. The clinical scoring scale is as follows: 0=normal; 1=limp tail or hind limb weakness (defined by foot slips between bars of cage top while walking); 2=limp tail and hind limb weakness; 3=partial hind limb paralysis (defined as no weight bearing on hind limbs but can still move one or both hind limbs to some extent); 4=complete hind limb paralysis; 5=moribund state (includes forelimb paralysis) or death. In some embodiments, compound 1 (methyl (E)-3-(5-oxo-4,5-dihydro-1H-tetrazol-1-yl)acrylate) significantly prevents the onset of disease paralysis when dosed at 60 mg/kg beginning on the day of immunization.

3. Animal Model to Assess Therapeutic Efficacy in Treating Psoriasis

The in vivo therapeutic efficacy of a compound for treating psoriasis can be assessed in an experimental animal model. For example, the severe, combined immunodeficient (SCID) mouse model can be used to evaluate the efficacy of compounds for treating psoriasis in humans.

SCID mice are used as tissue recipients. One biopsy for each normal or psoriatic volunteer is transplanted onto the dorsal surface of a recipient mouse. Treatment is initiated 1 to 2 weeks after transplantation. Animals with the human skin transplants are divided into treatment groups. Animals are treated twice daily for 14 days. At the end of treatment, animals are photographed and then euthanized. The transplanted human tissue along with the surrounding mouse skin is surgically removed and fixed in 10% formalin and samples obtained for microscopy. Epidermal thickness is measured. Tissue sections are stained with an antibody to the proliferation-associated antigen Ki-67 and with an anti-human CD3+ monoclonal antibody to detect human T lymphocytes in the transplanted tissue. Sections are also probed with antibodies to c-myc and β-catenin. A positive response to treatment is reflected by a reduction in the average epiderma thickness of the psoriatic skin transplants. A positive response is also associated with reduced expression of Ki-67 in keratinocytes.

4. Animal Model to Assess Therapeutic Efficacy in Treating Multiple Sclerosis

The in vivo therapeutic efficacy of a compound for treating multiple sclerosis can be assessed in an experimental animal model.

Experiments are conducted on female C57BL/6 mice aged 4-6 weeks and weighing 17-20 g. Experimental autoimmune encephalomyelitis (EAE) is actively induced using ≥95% pure synthetic myelin oligodendrocyte glycoprotein peptide 35-55 ($MOG_{35-55}$, MEVGWYRSPFSRVVH-LYRNGK) (SEQ ID NO: 1). Each mouse is anesthetized and receives 200 μg of MOG peptide and 15 μg of Saponin extract from Quilija bark emulsified in 100 μL of phosphate-buffered saline. A 25 μL volume is injected subcutaneously over four flank areas. Mice are also intraperitoneally injected with 200 ng of pertussis toxin in 200 μL of PBS. A second, identical injection of pertussis toxin is given after 48 h.

A test compound is administered at varying doses. Control animals receive 25 μL of DMSO. Daily treatment extends from day 26 to day 36 post-immunization. Clinical scores are obtained daily from day 0 post-immunization until day 60. Clinical signs are scored using the following protocol: 0, no detectable signs; 0.5, distal tail limpness, hunched appearance and quiet demeanor; 1, completely limp tail; 1.5, limp tail and hindlimb weakness (unsteady gait and poor grip with hindlimbs); 2, unilateral partial hindlimb paralysis; 2.5, bilateral hindlimb paralysis; 3, complete bilateral hindlimb paralysis; 3.5, complete hindlimb paralysis and unilateral forelimb paralysis; 4, total paralysis of hindlimbs and forelimbs.

Inflammation and demyelination are assessed by histology on sections from the CNS of EAE mice. Mice are euthanized after 30 or 60 days and whole spinal cords are removed and placed in 0.32 M sucrose solution at 4° C. overnight. Tissues are prepared and sectioned. Luxol fast blue stain is used to observe areas of demyelination. Haematoxylin and eosin staining is used to highlight areas of inflammation by darkly staining the nuclei of mononuclear cells. Immune cells stained with H&E are counted in a blinded manner under a light microscope. Sections are separated into gray and white matter and each sector is counted manually before being combined to give a total for the section. T cells are immunolabeled with anti-CD3$^+$ monoclonal antibody. After washing, sections are incubated with goat anti-rat HRP secondary antibody. Sections are then washed and counterstained with methyl green. Splenocytes isolated from mice at 30 and 60 days post-immunization are treated with lysis buffer to remove red blood cells. Cells are then resuspended in PBS and counted. Cells at a density of about $3 \times 10^6$ cells/mL are incubated overnight with 20 μg/mL of MOG peptide. Supernatants from stimulated cells are assayed for IFN-γ protein levels using an appropriate mouse IFN-γ immunoassay system.

Research Applications

Since subject compounds find use for the treatment of autoimmune and inflammatory diseases and disorders, such compounds are also useful as research tools. The present disclosure also provides a method for using the subject compounds as a research tool for studying a biological system or sample, or for discovering new chemical compounds that can be used for the treatment of autoimmune and inflammatory diseases and disorders, such as psoriasis or multiple sclerosis.

The disclosure provides for a method of studying a biological system or sample known to be associated with an autoimmune or inflammatory disease or disorder, the method comprising: (a) contacting the biological sample with a compound of the present disclosure or a salt or solvate or stereoisomer thereof; and (b) determining the efficacy of the compound on treating the biological sample.

Any suitable biological sample can be employed in such studies which can be conducted either in vitro or in vivo. Representative biological samples suitable for such studies include, but are not limited to, cells, cellular extracts, plasma membranes, tissue samples, isolated organs, mammals (such as mice, rats, guinea pigs, rabbits, dogs, pigs, humans, and so forth), and the like, with mammals being of particular interest.

When used as a research tool, a biological sample is typically contacted with a pharmaceutically effective amount of a subject compound. After the biological sample is exposed to the compound, the effects of the compound are determined using conventional procedures and equipment, such as the assays disclosed herein. Exposure encompasses contacting the biological sample with the compound or administering the compound to a subject. The determining step can involve measuring a response (a quantitative analysis) or can involve making an observation (a qualitative analysis). Measuring a response involves, for example, determining the effects of the compound on the biological sample using conventional procedures and equipment, such as radioligand binding assays and measuring ligand-mediated changes in functional assays. The assay results can be used to determine the activity level as well as the amount of compound necessary to achieve the desired result, that is, a pharmaceutically effective amount.

Additionally, the subject compounds can be used as research tools for evaluating other chemical compounds, and thus are also useful in screening assays to discover, for example, new compounds useful for the treatment of an autoimmune or inflammatory disease or disorder. In this manner, a subject compound can be used as a standard in an assay to allow comparison of the results obtained with a test compound and with the subject compounds to identify those test compounds that have about equal or superior activity, if any. For example, $EC_{50}$ data for a test compound or a group of test compounds is compared to the $EC_{50}$ data for a subject compound to identify those test compounds that have the desired properties, for example, test compounds having an $EC_{50}$ about equal or superior to a subject compound, if any.

This aspect includes, as separate embodiments, both the generation of comparison data (using the appropriate assays) and the analysis of test data to identify test compounds of interest. Thus, a test compound can be evaluated in a biological assay, by a method comprising the steps of: (a) conducting a biological assay with a test compound to provide a first assay value; (b) conducting the biological assay with a subject compound to provide a second assay value; where step (a) is conducted either before, after or concurrently with step (b); and (c) comparing the first assay value from step (a) with the second assay value from step (b). The assays that can be used for generation of comparison data are disclosed herein, such as the mouse EAE assays.

General Synthetic Procedures

Many general references providing commonly known chemical synthetic schemes and conditions useful for synthesizing the disclosed compounds are available (see, e.g., Smith and March, March's Advanced Organic Chemistry: Reactions, Mechanisms, and Structure, Fifth Edition, Wiley-Interscience, 2001; or Vogel, A Textbook of Practical Organic Chemistry, Including Qualitative Organic Analysis, Fourth Edition, New York: Longman, 1978).

Compounds as described herein can be purified by any purification protocol known in the art, including chromatography, such as HPLC, preparative thin layer chromatography, flash column chromatography and ion exchange chromatography. Any suitable stationary phase can be used, including normal and reversed phases as well as ionic resins. In certain embodiments, the disclosed compounds are purified via silica gel and/or alumina chromatography. See, e.g., Introduction to Modern Liquid Chromatography, 2nd Edition, ed. L. R. Snyder and J. J. Kirkland, John Wiley and Sons, 1979; and Thin Layer Chromatography, ed E. Stahl, Springer-Verlag, New York, 1969.

During any of the processes for preparation of the subject compounds, it may be necessary and/or desirable to protect sensitive or reactive groups on any of the molecules concerned. This may be achieved by means of conventional protecting groups as described in standard works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999, in "The Peptides"; Volume 3 (editors: E. Gross and J. Meienhofer), Academic Press, London and New York 1981, in "Methoden der organischen Chemie", Houben-Weyl, 4$^{th}$ edition, Vol. 15/1, Georg Thieme Verlag, Stuttgart 1974, in H.-D. Jakubke and H. Jescheit, "Aminosauren, Peptide, Proteine", Verlag Chemie, Weinheim, Deerfield Beach, and Basel 1982, and/or in Jochen Lehmann, "Chemie der Kohlenhydrate: Monosaccharide and Derivate", Georg Thieme Verlag, Stuttgart 1974. The protecting groups may be removed at a convenient subsequent stage using methods known from the art.

The subject compounds can be synthesized via a variety of different synthetic routes using commercially available starting materials and/or starting materials prepared by conventional synthetic methods. All of the compounds described herein (including prodrugs) can be prepared by adaptation of these methods.

Examples of synthetic routes that can be used to synthesize the compounds disclosed herein are described in the Examples below.

Stereoisomers of the compounds can be isolated by procedures known to those skilled in the art. The individual stereoisomers may be obtained, for instance, by a resolution technique or by chromatography techniques (e.g., silica gel chromatography, chiral chromatography, etc.).

Although the synthetic schemes discussed herein may not illustrate the use of protecting groups, skilled artisans will recognize that in some instances certain substituents may include functional groups requiring protection. The exact identity of the protecting group used will depend upon, among other things, the identity of the functional group being protected and the reaction conditions used in the particular synthetic scheme, and will be apparent to those of skill in the art. Guidance for selecting protecting groups, their attachment and removal suitable for a particular application can be found, for example, in Greene & Wuts, supra.

Prodrugs as described herein can be prepared by routine modification of the methods described herein. Alternatively, such prodrugs can be prepared by reacting a suitably protected compound with a suitable progroup. Conditions for carrying out such reactions and for deprotecting the product to yield prodrugs as described herein are well-known.

In certain embodiments, in the above methods, the method further includes separating isomers with a resolution technique. In certain embodiments, in the above methods, the method further includes separating isomers with chiral chromatography. In certain embodiments, the disclosure provides a method for preparing an optically active compound.

In some embodiments, the above methods further include the step of forming a salt of a compound disclosed herein. Embodiments are directed to the other processes described herein, and to the product prepared by any of the processes described herein.

EXAMPLES

The following examples are put forth so as to provide those of ordinary skill in the art with a complete disclosure and description of how to make and use the embodiments, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. As will be understood, by those of skill in the art of organic synthesis and medicinal chemistry the specific conditions set forth below are exemplary and can be varied or adapted to other reagents and products in routine fashion. Unless indicated otherwise, parts are parts by weight, molecular weight is weight average molecular weight, temperature is in degrees Celsius, and pressure is at or near atmospheric. Standard abbreviations may be used.

Example 1

Preparation of Compounds

Preparation of methyl (E)-3-(5-oxo-4,5-dihydro-1H-tetrazol-1-yl)acrylate

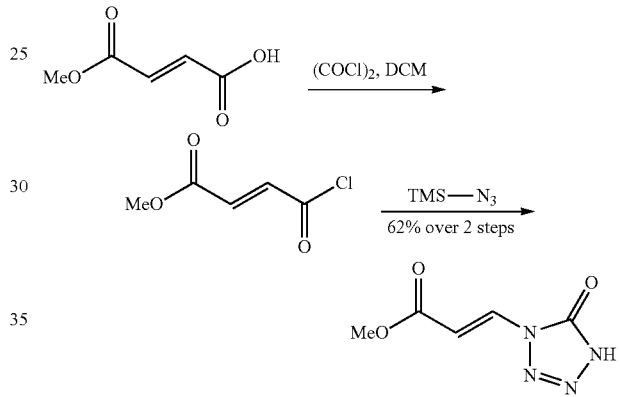

Oxalyl chloride (2.0 M in CH$_2$Cl$_2$; 15.2 mL, 30.3 mmol) was added dropwise over 2-3 min to a stirred suspension of monomethylfumarate (2.63 g, 20.2 mmol) in CH$_2$Cl$_2$ (80 mL) at 0° C. under nitrogen. After complete addition, the mixture was stirred at 0° C. for 5 min then allowed to warm to room temperature and stirred for 3 hr (a yellow solution developed). A small aliquot was removed and quenched with MeOH. TLC of the reaction mixture indicated no acid was remaining. The mixture was concentrated under vacuum and CH$_2$Cl$_2$ (50 mL) was added to the residue and the mixture concentrated under vacuum once more to leave the acid chloride, which was used directly in the tetrazolone-forming step (yield assumed quantitative=3.0 g). A safety notice for the procedure: Azide compounds are potentially explosive. This reaction was performed behind a blast shield.

Azidotrimethylsilane (16.1 mL, 121.2 mmol) was added in one portion to the acid chloride from the above procedure (3.0 g, 20.2 mmol) at room temperature (gas evolution was noted). The mixture was place under nitrogen and heated from room temperature to 100° C. (block temperature), then stirred at 100° C. for 90 min. After cooling to room temperature, the excess solvent was removed under vacuum to leave a crude residue. EtOAc (150 mL) and saturated NaHCO$_3$ (150 mL) were added to the residue. A solid formed and the mixture was filtered. The filter cake was dissolved in H$_2$O (350 mL) and then combined with the saturated NaHCO$_3$ layer of the filtrate. EtOAc (150 mL) was added to the combined aqueous system and the mixture was acidified to about pH 3 with 1N HCl. The aqueous and organic layers were partitioned and the aqueous layer was extracted with EtOAc (2×100 mL). The combined organic extracts were dried over $Na_2SO_4$, filtered and the solvent removed under vacuum to leave a crude residue (2.6 g; about 90% purity of desired product). The residue was purified by column chromatography on silica gel using $CH_2Cl_2$/MeOH (1:0 to 9:1) as eluent to give the product (2.14 g, 62% over 2 steps) as a solid. $^1$H NMR (DMSO-$d_6$, 300 MHz): δ 7.73 (d, J=14.4 Hz, 1H), 6.49 (d, J=14.4 Hz, 1H), 3.71 (s, 3H), −1.0 (br. s, 1H) $^{13}$C NMR (DMSO-$d_6$, 75 MHz): δ 165.7, 149.8, 132.3, 106.3, 51.9; m/z=169.34 [M−H]+; HRMS (EI): [M+H]$^+$ calc'd for $C_5H_6N_4O_3$ m/z 171.0518. found 171.0522.

The above reaction can be scaled-up without loss of yield. The tetrazolone-forming step with TMS-$N_3$ can also be conducted in solvents such as 1,4-dioxane, without loss of yield. Additionally, after purification by column chromatography, the tetrazolone product can be triturated with MeOH and filtered, if required.

Preparation of methyl (E)-3-(4-methyl-5-oxo-4,5-dihydro-1H-tetrazol-1-yl)acrylate

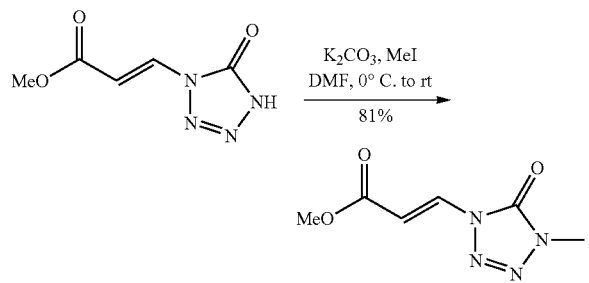

$K_2CO_3$ (1.92 g, 14.0 mmol) was added in one portion to a stirred mixture of methyl (E)-3-(5-oxo-4,5-dihydro-1H-tetrazol-1-yl)acrylate (0.95 g, 5.6 mmol) and iodomethane (0.7 mL, 11.2 mmol) in DMF (15 mL) at 0° C. under nitrogen. The mixture was stirred at 0° C. for 20 min, then allowed to warm to room temperature and stirred overnight. LC/MS indicated complete reaction, so the mixture was poured in to $H_2O$ (150 mL) and EtOAc (50 mL). The aqueous and organic layers were partitioned and the aqueous layer was extracted with EtOAc (2×30 mL). The combined organic layers were dried ($Na_2SO_4$), filtered and the solvent removed under vacuum to leave a crude residue, which was dry-loaded on to silica gel. The residue was purified by column chromatography on silica gel using hexanes/EtOAc (1:0 to 1:1) as eluent to give the desired product (834 mg, 81%) as a solid. $^1$H NMR (CDCl$_3$, 300 MHz) δ 7.88 (dd, J=14.4, 0.6 Hz, 1H), 6.68 (d, J=14.4 Hz, 1H), 3.80 (s, 3H), 3.65 (s, 3H); $^{13}$C NMR (CDCl$_3$, 75 MHz) δ 166.2, 148.7, 132.2, 108.6, 52.2, 31.6; m/z=no parent-ion by LC/MS or HRMS. The above reaction can be scaled-up without loss of yield.

The following compounds can also be prepared using the above method. Each reaction utilized methyl (E)-3-(5-oxo-4,5-dihydro-1H-tetrazol-1-yl)acrylate (170 mg, 1.0 mmol), alkylating agent (2 mmol) and $K_2CO_3$ (346 mg, 2.5 mmol) in DMF (3 mL) at room temperature (no prior cooling to 0° C.).

Preparation of methyl (E)-3-(4-deuteriomethyl-5-oxo-4,5-dihydro-1H-tetrazol-1-yl)acrylate

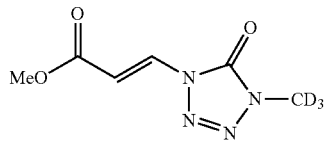 [SMILES: [2H]C([2H])([2H])n1nnn(/C=C/C(=O)OC)c1=O]

Product (159 mg, 85%) isolated as a solid after column chromatography [hexanes/EtOAc (1:0 to 3:2) as eluent]. $^1$H NMR (CDCl$_3$, 300 MHz) δ 7.90 (d, J=14.4 Hz, 1H), 6.70 (d, J=14.4 Hz, 1H), 3.82 (s, 3H); $^{13}$C NMR (CDCl$_3$, 75 MHz) δ 166.2, 148.7, 132.2, 108.6, 52.2 (note: $^{13}$C of $CD_3$ not observed, or weak signal, under $^{13}$C NMR acquisition conditions); m/z=188.20 [M+H]$^+$; HRMS (EI): [M+MeCN+H]$^+$ calc'd for $C_6H_5D_3N_4O_3$+MeCN m/z 229.1128. found 229.1138.

Preparation of methyl (E)-3-(4-deuterioisopropyl-5-oxo-4,5-dihydro-1H-tetrazol-1-yl)acrylate

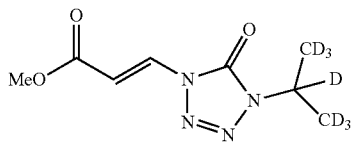 [SMILES: [2H]C([2H])([2H])C([2H])(n1nnn(/C=C/C(=O)OC)c1=O)C([2H])([2H])[2H]]

Reaction stirred at room temperature overnight, then heated to 50° C. and stirred for 2 hr. Product (60 mg, 27%) isolated as an oil after column chromatography [hexanes/EtOAc (1:0 to 3:2) as eluent]. $^1$H NMR (CDCl$_3$, 300 MHz) δ 7.91 (d, J=14.4 Hz, 1H), 6.70 (d, J=14.4 Hz, 1H), 3.82 (s, 3H); $^{13}$C NMR (CDCl$_3$, 75 MHz) δ 166.2, 147.9, 132.3, 108.3, 52.1 (note: $^{13}$C of $CD_3$ (×2), or CD not observed, or weak signals, under $^{13}$C NMR acquisition conditions); m/z=220.21 [M+H]$^+$; HRMS (EI): [M+H+MeCN]$^+$ calc'd for $C_8H_5D_7N_4O_3$+MeCN m/z 261.1693. found 261.1703.

Preparation of methyl (E)-3-(4-(2-(dimethylamino)ethyl)-5-oxo-4,5-dihydro-1H-tetrazol-1-yl)acrylate

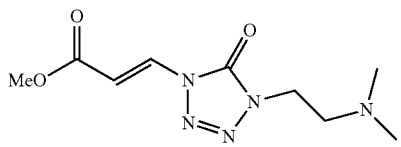 [SMILES: COC(=O)/C=C/n1nnn(CCN(C)C)c1=O]

Reaction stirred at room temperature overnight, then heated to 50° C. and stirred for 2 hr. Product (60 mg, 25%) isolated as a solid after column chromatography [DCM/2N $NH_3$ in MeOH (1:0 to 95:5) as eluent]. $^1$H NMR (CDCl$_3$, 300 MHz) δ 7.90 (d, J=14.4 Hz, 1H), 6.69 (d, J=14.4 Hz, 1H), 4.07 (t, J=6.3 Hz, 2H), 3.81 (s, 3H), 2.74 (t, J=6.3 Hz, 2H), 2.28 (s, 6H); $^{13}$C NMR (CDCl$_3$, 75 MHz) δ 166.3, 148.6, 132.3, 108.5, 56.9, 52.2, 45.4, 43.2; m/z=242.17 [M+H]$^+$; HRMS (EI): [M+H]$^+$ calc'd for $C_9H_{15}N_5O_3$ m/z 242.1253. found 242.1250.

General Procedure for the Alkylation of methyl (E)-3-(5-oxo-4,5-dihydro-1H-tetrazol-1-yl)acrylate with Alkyliodides or Alkylbromides Leading to methyl (E)-3-(4-alkyl-5-oxo-4,5-dihydro-1H-tetrazol-1-yl)acrylate

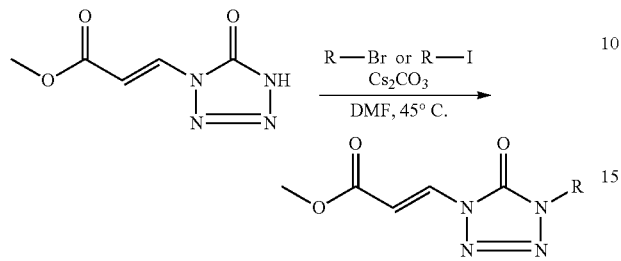

A stirring mixture of methyl (E)-3-(5-oxo-4,5-dihydro-1H-tetrazol-1-yl)acrylate (1 eq), corresponding alkyliodide or alkylbromide (1.3 eq), Cs$_2$CO$_3$ (1.1 eq) and dry DMF (1 mL/1 mmol) in a screw capped vial was heated at 45° C. for 4 h. Subsequently, reaction mixture was cooled to room temperature, diluted with EtOAc/H$_2$O and organic layer was separated. Upon extracting aqueous layer with EtOAc, the combined organic layers were washed with water (5 mL) and brine (3 mL) successively, stirred over anhydrous MgSO$_4$, filtered and concentrated by rotary evaporator under vacuum. Silica gel column chromatographic (Combiflash Teledyne® with RediSep® silica gel column) purification of thus obtained crude concentrate provided methyl (E)-3-(4-alkyl-5-oxo-4,5-dihydro-1H-tetrazol-1-yl)acrylates. The following analogs can also be prepared in the similar manner as described herein.

Compound 6: Methyl (E)-3-(4-isopropyl-5-oxo-4,5-dihydro-1H-tetrazol-1-yl)acrylate

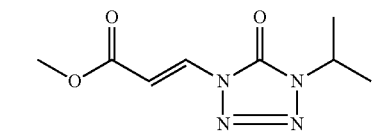

$^1$H NMR (300 MHz, CDCl$_3$) δ 7.87 (d, J=14.4 Hz, 1H), 6.65 (d, J=14.4 Hz, 1H), 4.50 (hept, J=6.8 Hz, 1H), 3.79 (s, 3H), 1.50 (d, J=6.8 Hz, 7H). $^{13}$C NMR (75 MHz, CDCl$_3$) δ 166.31, 148.01, 132.35, 108.47, 52.21, 49.03, 21.20. LC/MS: rt 4.62 min (B), purity 98%, MS (m/e) 213 (MH$^+$).

Compound 13: Methyl (E)-3-(4-(2-methoxyethyl)-5-oxo-4,5-dihydro-1H-tetrazol-1-yl)acrylate

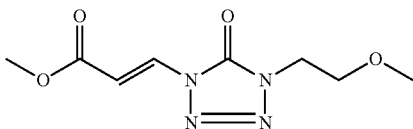

$^1$H NMR (300 MHz, CDCl$_3$) δ 7.87 (d, J=14.4 Hz, 1H), 6.66 (d, J=14.4 Hz, 1H), 4.16 (t, J=5.4 Hz, 2H), 3.80 (s, 3H), 3.75 (t, J=5.4 Hz, 2H), 3.35 (s, 3H). $^{13}$C NMR (75 MHz, CDCl$_3$) δ 166.04, 148.43, 132.11, 108.44, 68.70, 58.82, 52.02, 44.84. LC/MS: rt 5.51 min (A), purity 98%, MS (m/e) 229 (MH$^+$).

Compound 14: Methyl (E)-3-(4-(2-methoxy-2-oxoethyl)-5-oxo-4,5-dihydro-1H-tetrazol-1-yl)acrylate

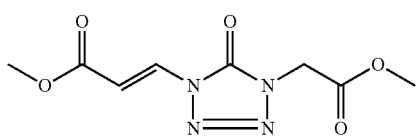

$^1$H NMR (300 MHz, CDCl$_3$) δ 7.89 (d, J=14.4 Hz, 1H), 6.69 (d, J=14.4 Hz, 1H), 4.77 (s, 2H), 3.83 (s, 3H), 3.82 (s, 3H). $^{13}$C NMR (75 MHz, CDCl$_3$) δ 165.88, 165.83, 148.12, 131.97, 108.85, 53.21, 52.07, 45.44. LC/MS: rt 5.71 min (A), purity 98%, MS (m/e) 243 (MH$^+$).

Compound 11: Synthesis of Methyl (E)-3-(4-cyclopentyl-5-oxo-4,5-dihydro-1H-tetrazol-1-yl)acrylate

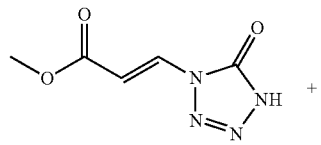

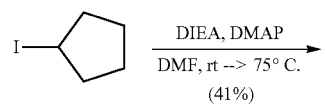

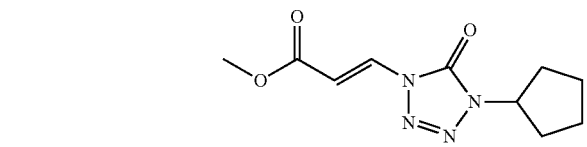

To a solution of methyl (E)-3-(5-oxo-4,5-dihydro-1H-tetrazol-1-yl)acrylate (1, 50 mg, 0.3 mmol) and cyclopentyl iodide (2, 68 μL, 115 mg, 0.6 mmol) in DMF (1 mL), DIEA (70 μL, 52 mg, 0.4 mmol)) was added. The reaction mixture was allowed to stir at 75° C. for 1.5 h, cooled down to room temperature and diluted with brine (20 mL). The resulting aqueous layer was then extracted with DCM (3×15 mL), and the combined organic layer was dried (MgSO$_4$), filtered and concentrated to give 125 mg of a brown residue. Column chromatography (Combiflash Isco; 12 g Redisep column; eluted with hexanes for 5 min, 50% EtOAc/hexanes over 10 min till the desired compound eluted) provided 29 mg (41%) of a clear oil. $^1$H NMR (300 MHz, CDCl$_3$) δ 7.87 (d, J=14.4 Hz, 1H), 6.66 (d, J=14.4 Hz, 1H), 4.63 (ddd, J=14.2, 7.8, 6.1 Hz, 1H), 3.80 (s, 3H), 2.20-1.83 (m, 6H), 1.82-1.67 (m, 2H). $^{13}$C NMR (75 MHz, CDCl$_3$) δ 166.47, 148.41, 132.52, 108.60, 57.45, 52.34, 31.87, 24.52. MS m/e: 239 (M+H)$^+$.

Compound 12: Synthesis of Methyl (E)-3-(5-oxo-4-(tetrahydro-2H-pyran-4-yl)-4,5-dihydro-1H-tetrazol-1-yl)acrylate

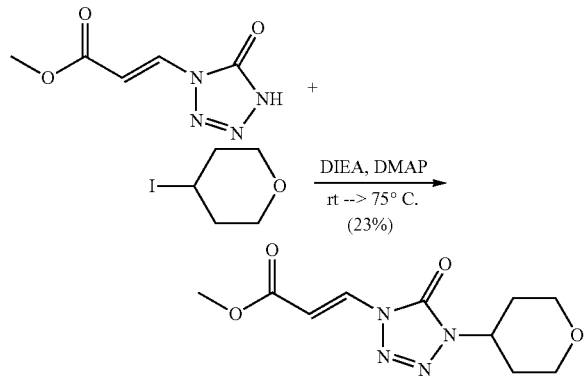

A mixture of methyl (E)-3-(5-oxo-4,5-dihydro-1H-tetrazol-1-yl)acrylate (50 mg, 0.3 mmol), 4-iodotetrahydropyran (0.5 g, 2.4 mmol), DIEA (0.5 mL, 371 mg, 2.9 mmol) and DMAP (50 mg, 0.4 mmol) was allowed to stir at 75° C. overnight. The reaction mixture was cooled down to room temperature, diluted with brine (20 mL) and extracted with DCM (3×20 mL). The combined organic layer was then dried (MgSO$_4$), filtered and concentrated to give 560 mg of a brown residue. Column chromatography (Combiflash Isco; 24 g Redisep column; eluted with hexanes for 5 min, 50% EtOAc/hexanes over 15 min till compound eluted) provided 17 mg (23%) of compound 12 as a white solid. $^1$H NMR (300 MHz, CDCl$_3$) δ 7.89 (d, J=14.4 Hz, 1H), 6.68 (d, J=14.4 Hz, 1H), 4.37 (tt, J=11.5, 4.3 Hz, 1H), 4.19-4.07 (m, 2H), 3.82 (s, 3H), 3.54 (td, J=11.9, 2.2 Hz, 2H), 2.27-2.13 (m, 2H), 2.04-1.94 (m, 2H). $^{13}$C NMR (75 MHz, CDCl$_3$) δ 166.41, 132.38, 108.97, 105.36, 66.90, 52.99, 52.43, 31.41. MS m/e: 255 (M+H)$^+$.

Compound 19: Synthesis of Methyl (E)-3-(4-(2-hydroxy-2-methylpropyl)-5-oxo-4,5-dihydro-1H-tetrazol-1-yl)acrylate

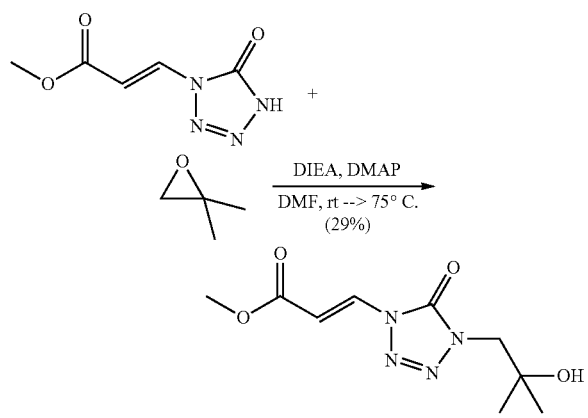

To a solution of methyl (E)-3-(5-oxo-4,5-dihydro-1H-tetrazol-1-yl)acrylate (100 mg, 0.6 mmol) and 2,2-dimethyloxirane (1.1 mL, 890 mg, 12.4 mmol) in DMF (1 mL), cesium carbonate (230 mg, 0.7 mmol)) was added. The reaction mixture was allowed to stir at 85° C. for 9 h, cooled down to room temperature and diluted with water (25 mL). The resulting aqueous layer was then extracted with DCM (3×20 mL), and the combined organic layer was dried (MgSO$_4$), filtered and concentrated to give 800 mg of a yellow residue. Column chromatography (Combiflash Isco; 12 g Redisep column; eluted with hexanes for 5 min, 50% EtOAc/hexanes over 10 min till the desired compound eluted) provided 42 mg (29%) of a white solid with 92% purity. Purification by HPLC provided 27 mg of compound 19 as a white solid. $^1$H NMR (300 MHz, CDCl$_3$) δ 7.97 (d, J=14.1 Hz, 1H), 5.09 (d, J=14.1 Hz, 1H), 3.73 (s, 3H), 3.46 (s, 2H), 1.53 (s, 6H). $^{13}$C NMR (75 MHz, CDCl$_3$) δ 167.28, 153.87, 138.86, 99.79, 79.75, 54.45, 51.67, 27.75. MS m/e: 243 (M+H)$^+$.

Compound 7: Preparation of Methyl (E)-3-(4-((3-methyloxetan-3-yl)methyl)-5-oxo-4,5-dihydro-1H-tetrazol-1-yl)acrylate

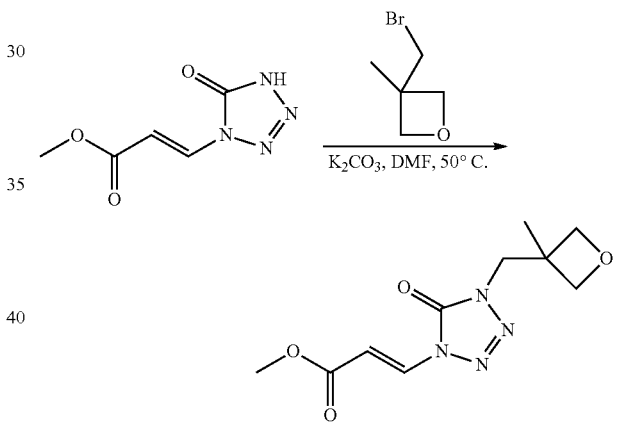

A mixture of methyl (E)-3-(5-oxo-4,5-dihydro-1H-tetrazol-1-yl)acrylate (0.10 g, 0.6 mmol), 3-(bromomethyl)-3-methyloxetane (0.15 g, 0.9 mmol), and K$_2$CO$_3$ (0.16 g, 1.2 mmol) in dimethylformamide (2 mL) was stirred at 50° C. for 18 h After cooling to room temperature, the reaction mixture was then partitioned between water and ethyl acetate. The organic layer was separated, dried over sodium sulfate, filtered, and concentrated under reduced pressure to give a residue, which was purified by chromatography eluting with ethyl acetate/hexanes (1/1) to provide methyl (E)-3-(4-((3-methyloxetan-3-yl)methyl)-5-oxo-4,5-dihydro-1H-tetrazol-1-yl)acrylate as a pale white solid (0.12 g, 78%).

$^1$H NMR (CDCl$_3$, 300 MHz) 7.85 (d, J=14.5 Hz, 1H), 6.65 (d, J=14.5 Hz, 1H), 4.64 (d, J=6.4 Hz, 2H), 4.42 (d, J=6.4 Hz, 2H), 4.17 (s, 2H), 3.78 (s, 3H), 1.33 (s, 3H) ppm; $^{13}$C NMR (CDCl$_3$, 300 MHz) 166.87, 149.63, 132.78, 109.36, 80.36, 52.36, 51.54, 40.55, 21.63 ppm; MS m/e: 255 (M+H)$^+$.

Compound 9: Preparation of Methyl (E)-3-(4-(methoxymethyl)-5-oxo-4,5-dihydro-1H-tetrazol-1-yl)acrylate

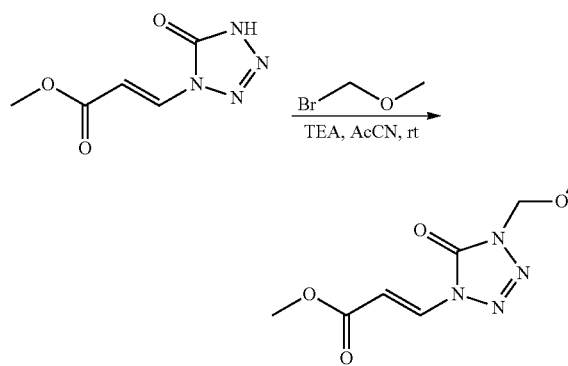

A mixture of methyl (E)-3-(5-oxo-4,5-dihydro-1H-tetrazol-1-yl)acrylate (0.10 g, 0.6 mmol), bromo(methoxy)methane (0.09 g, 0.7 mmol), and TEA (0.07 g, 0.7 mmol) in acetonitrile (2 mL) was stirred at room temperature for 18 h. The reaction mixture was then partitioned between water and ethyl acetate. The organic layer was separated, dried over sodium sulfate, filtered, and concentrated under reduced pressure to give a residue, which was purified by chromatography eluting with ethyl acetate/hexanes (4/6) to provide methyl (E)-3-(4-(methoxymethyl)-5-oxo-4,5-dihydro-1H-tetrazol-1-yl)acrylate as a pale white solid (0.08 g, 63%)

$^1$H NMR (CDCl$_3$, 300 MHz) 7.86 (d, J=14.4 Hz, 1H), 6.66 (d, J=14.4 Hz, 1H), 5.29 (s, 2H), 3.79 (s, 3H), 3.45 (s, 3H) ppm; $^{13}$C NMR (CDCl$_3$, 300 MHz) 166.87, 149.14, 132.67, 109.39, 75.77, 58.22, 52.37 ppm; MS m/e: 215 (M+H)$^+$.

Compound 10: Preparation of Methyl (E)-3-(4-(dimethylcarbamoyl)-5-oxo-4,5-dihydro-1H-tetrazol-1-yl)acrylate

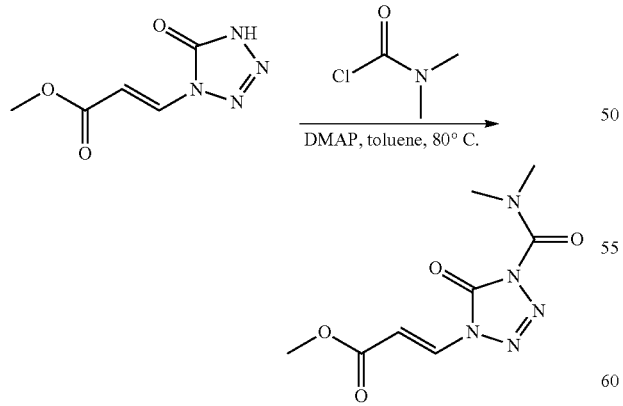

A mixture of methyl (E)-3-(5-oxo-4,5-dihydro-1H-tetrazol-1-yl)acrylate (0.17 g, 1 mmol), dimethylcarbamic chloride (0.2 g, 1.9 mmol), and DMAP (0.17 g, 1.4 mmol) in toluene (5 mL) was stirred at 80° C. for 3 h After cooling to room temperature, the reaction mixture was then partitioned between water and ethyl acetate. The organic layer was separated, dried over sodium sulfate, filtered, and concentrated under reduced pressure to give a residue, which was purified by chromatography eluting with ethyl acetate/hexanes (4/1) to provide methyl (E)-3-(4-(dimethylcarbamoyl)-5-oxo-4,5-dihydro-1H-tetrazol-1-yl)acrylate as a pale white solid (0.14 g, 59%).

$^1$H NMR (CDCl$_3$, 300 MHz) 7.86 (d, J=13.8 Hz, 1H), 6.69 (d, J=13.8 Hz, 1H), 3.83 (s, 3H), 3.15 (m, 6H) ppm; $^{13}$C NMR (CDCl$_3$, 300 MHz) 166.66, 147.58, 146.57, 132.20, 109.90, 52.44, 38.70, 37.68 ppm; MS m/e: 242 (M+H)$^+$.

The following analogs were prepared in the similar manner as described herein.

Compound 8: Methyl (E)-3-(4-(2-amino-2-oxoethyl)-5-oxo-4,5-dihydro-1H-tetrazol-1-yl)acrylate Compound 8 was prepared according to the method used to prepare Compound 7.

$^1$H NMR (DMSO-d$_6$, 300 MHz) 7.77 (m, 2H), 7.45 (bs, 1H), 5.53 (m, 1H), 4.64 (s, 2H), 3.73 (s, 3H) ppm; $^{13}$C NMR (DMSO-d$_6$, 300 MHz) 169.19, 167.22, 149.66, 133.14, 108.11, 51.42, 46.27 ppm; MS m/e: 228 (M+H)$^+$.

Method B:

Alternate synthetic method for the preparation of Alkyl (E or Z)-3-(4-alkyl/aryl-5-oxo-4,5-dihydro-1H-tetrazol-1-yl)acrylates from 1-alkyl/aryl-1,4-dihydro-5H-tetrazol-5 one

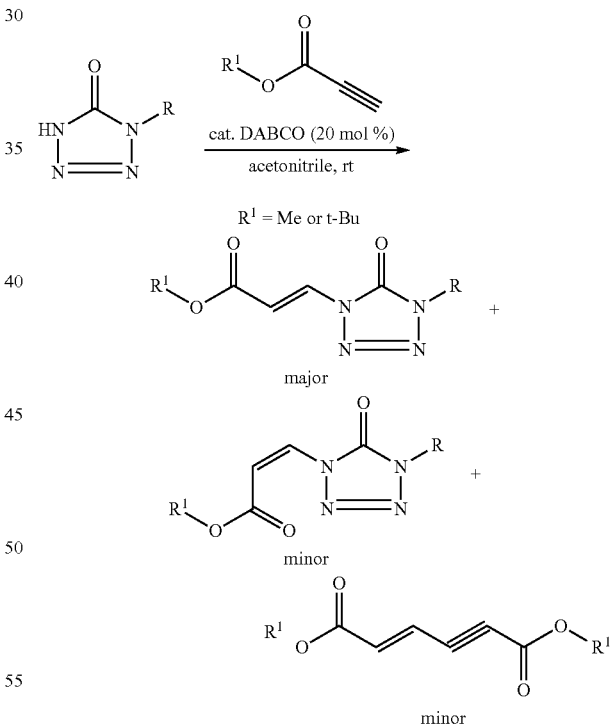

Alkyl (methyl or t-butyl) propiolate (1.3 eq) in dry acetonitrile (1 mL/mmol) was added dropwise to a stirring solution of 1-alkyl/aryl-1,4-dihydro-5H-tetrazol-5-one (1 eq) and DABCO (0.2 eq) in dry acetonitrile (0.5 mL/mmol) at room temperature over a period of 20 min. Upon complete addition of alkyl propiolate, clear homogeneous reaction was stirred at room temperature which transformed to dark reaction solution after 3 h (12 h for t-butylpropiolate). LC/MS and silica gel TLC analysis of reaction aliquot indicated near quantitative consumption of 1-alkyl/aryl-1,4-dihydro-5H-tetrazol-5-one. Subsequently, reaction solution was concentrated to dryness and purified by Combiflash Teledyne® with RediSep® silica gel column. Three spots that were observed on the TLC were isolated independently and characterized by $^1$H NMR as E regio-isomer [major product, alkyl (E)-3-(4-alkyl/aryl-5-oxo-4,5-dihydro-1H-tetrazol-1-yl)acrylates], along with minor products corresponding to Z regio-isomer [alkyl (Z)-3-(4-alkyl/aryl-5-oxo-4,5-dihydro-1H-tetrazol-1-yl)acrylates] and dialkyl (E)-hex-2-en-4-ynedioate (resulting from the homo coupling of alkylpropiolate), Compound 20: Dimethyl 3,3'-(5-oxo-1H-tetrazole-1,4(5H)-diyl)(2E,2'E)-diacrylate

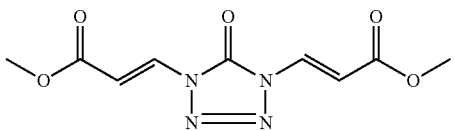

$^1$H NMR (300 MHz, CDCl$_3$) δ 7.88 (d, J=14.4 Hz, 2H), 6.72 (d, J=14.5 Hz, 2H), 3.83 (s, 6H). $^{13}$C NMR (75 MHz, CDCl$_3$) δ 165.84, 145.87, 131.59, 109.92, 52.45. LC/MS: rt 6.71 min (A), purity 98%, MS (m/e) 225 (MH$^+$—C$_2$H$_5$).

Compound 5: Methyl (E)-3-(4-ethyl-5-oxo-4,5-dihydro-1H-tetrazol-1-yl)acrylate

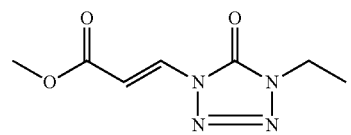

$^1$H NMR (300 MHz, CDCl$_3$) δ 7.87 (d, J=14.4 Hz, 1H), 6.66 (d, J=14.4 Hz, 1H), 4.03 (q, J=7.3 Hz, 2H), 3.80 (s, 3H), 1.46 (t, J=7.3 Hz, 3H). $^{13}$C NMR (75 MHz, CDCl$_3$) δ 166.06, 148.15, 132.11, 108.37, 52.01, 40.46, 13.61. LC/MS: rt 5.96 min (A), purity 98%, MS (m/e) 199 (MH$^+$).

Compound 22: Methyl (Z)-3-(4-ethyl-5-oxo-4,5-dihydro-1H-tetrazol-1-yl)acrylate

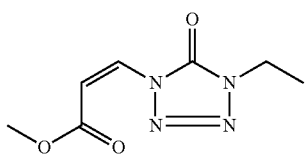

$^1$H NMR (300 MHz, CDCl$_3$) δ 6.84 (d, J=9.8 Hz, 1H), 5.85 (d, J=9.8 Hz, 1H), 4.02 (q, J=7.3 Hz, 2H), 3.79 (s, 3H), 1.45 (t, J=7.3 Hz, 3H). $^{13}$C NMR (75 MHz, CDCl$_3$) δ 164.57, 152.57, 124.72, 112.25, 52.08, 40.42, 13.64. LC/MS: rt 5.13 min (A), purity 98%, MS (m/e) 199 (MH$^+$).

Compound 15: tert-Butyl (E)-3-(4-methyl-5-oxo-4,5-dihydro-1H-tetrazol-1-yl)acrylate

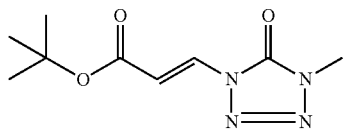 [SMILES: Cn1nnn(/C=C/C(=O)OC(C)(C)C)c1=O]

$^1$H NMR (300 MHz, CDCl$_3$) δ 7.74 (d, J=14.4 Hz, 1H), 6.57 (d, J=14.4 Hz, 1H), 3.64 (s, 3H), 1.50 (s, 9H). $^{13}$C NMR (75 MHz, CDCl$_3$) δ 164.70, 148.56, 131.12, 110.90, 81.47, 31.43, 28.04. LC/MS: rt 7.41 min (A), purity 98%, MS (m/e) 212 (MH$^+$—CH$_3$).

Compound 23: tert-Butyl (Z)-3-(4-methyl-5-oxo-4,5-dihydro-1H-tetrazol-1-yl)acrylate

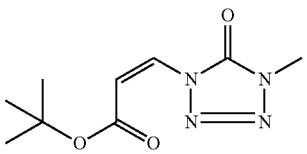 [SMILES: Cn1nnn(/C=C\C(=O)OC(C)(C)C)c1=O]

$^1$H NMR (300 MHz, CDCl$_3$) δ 6.72 (d, J=9.8 Hz, 1H), 5.79 (d, J=9.7 Hz, 1H), 3.63 (s, 3H), 1.49 (s, 9H). $^{13}$C NMR (75 MHz, CDCl$_3$) δ 163.20, 148.75, 123.18, 115.16, 82.32, 31.40, 27.96. LC/MS: rt 6.55 min (A), purity 98%, MS (m/e) 212 (MH$^+$—CH$_3$).

Compound 16: Preparation of Methyl (E)-3-(5-oxo-4-phenyl-4,5-dihydro-1H-tetrazol-1-yl)acrylate Step 1: Preparation of 1-phenyl-1,4-dihydro-5H-tetrazol-5-one

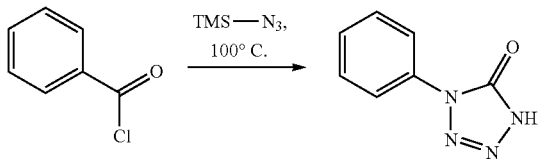 [SMILES: O=C(Cl)c1ccccc1 ; C[Si](C)(C)N=[N+]=[N-] ; O=c1[nH]nnn1-c1ccccc1]

A safety notice for the procedure: Azide compounds are potentially explosive. This reaction was performed behind a blast shield. A stirred mixture of azidotrimethylsilane (2.4 mL, 18 mmol) and benzoyl chloride (422 mg, 3.0 mmol) was heated from room temperature to 100° C. (block temperature) in a sealed vial with pressure-release cap. The mixture was then stirred at 100° C. overnight (Note: pressure develops during heating). After cooling, the mixture was concentrated under vacuum and the residue partitioned between EtOAc (10 mL) and a saturated aqueous solution of NaHCO$_3$ (10 mL). The organic layer was extracted with a further quantity of saturated aqueous NaHCO$_3$ (1×10 mL) [note: organic layer assessed by TLC to ascertain if tetrazolone product completely removed. If tetrazolone still present in organic layer, then further extractions with saturated NaHCO$_3$ are used]. EtOAc (20 mL) was added to the combined NaHCO₃ layers, and the pH was adjusted to <3 using 6N HCl with efficient stirring. The aqueous and organic layers were partitioned and the aqueous layer was extracted with EtOAc (2×10 mL). The combined organic layers were dried (Na₂SO₄), filtered and the solvent removed under vacuum to afford the product (369 mg, 76%) as a solid. A sample was recrystallized from EtOAc. ¹H NMR (DMSO-d₆, 300 MHz) δ 7.85-7.81 (m, 2H), 7.57-7.50 (m, 2H), 7.41 (dt, J=7.5, 1.5 Hz, 1H), −1.3 (br. s, 1H); ¹³C NMR (DMSO-d₆, 75 MHz) δ 150.3, 134.2, 129.5, 127.6, 119.5; m/z=163.18 [M+H]⁺ and 161.24 [M−H]⁺; HRMS (EI): [M−H]⁺ calc'd for C₇H₆N₄O m/z 161.0463. found 161.0532.

Step 2: Preparation of methyl (E)-3-(5-oxo-4-phenyl-4,5-dihydro-1H-tetrazol-1-yl)acrylate

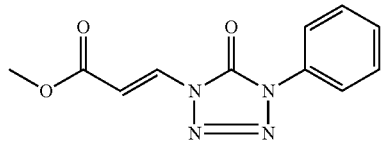 [SMILES: COC(=O)/C=C/n1nnn(-c2ccccc2)c1=O]

¹H NMR (300 MHz, CDCl₃) δ 8.01-7.80 (m, 3H), 7.52 (t, J=7.7 Hz, 2H), 7.41 (t, J=7.4 Hz, 1H), 6.74 (d, J=14.4 Hz, 1H), 3.83 (s, 3H). ¹³C NMR (75 MHz, CDCl₃) δ 165.93, 146.48, 133.85, 131.83, 129.65, 128.33, 119.47, 108.88, 52.10. LC/MS: rt 7.68 min (A), purity 98%, MS (m/e) 247 (MH⁺).

Compound 17: Preparation of Methyl (E)-3-(5-oxo-4-(pyridin-3-yl)-4,5-dihydro-1H-tetrazol-1-yl)acrylate Step 1: Preparation of 1-(pyridin-3-yl)-1,4-dihydro-5H-tetrazol-5-one

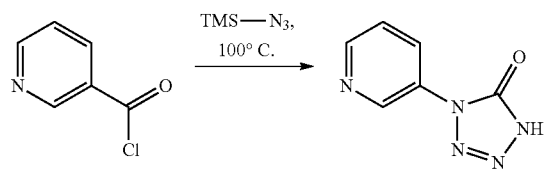 [SMILES: C[Si](C)(C)N=[N+]=[N-] ; O=C(Cl)c1cccnc1 ; O=c1[nH]nnn1-c1cccnc1]

A safety notice for the procedure: Azide compounds are potentially explosive. This reaction was performed behind a blast shield. A stirred mixture of azidotrimethylsilane (2.4 mL, 18 mmol) and nicotinoyl chloride (425 mg, 3.0 mmol) was heated from room temperature to 100° C. (block temperature) in a sealed vial with pressure-release cap. The mixture was then stirred at 100° C. overnight (Note: pressure develops during heating). After cooling, the mixture was concentrated under vacuum and the residue partitioned between EtOAc (10 mL) and a saturated aqueous solution of NaHCO₃ (10 mL). The organic layer was extracted with a further quantity of saturated aqueous NaHCO₃ (1×10 mL) [note: organic layer assessed by TLC to ascertain if tetrazolone product completely removed. If tetrazolone still present in organic layer, then further extractions with saturated NaHCO₃ are used]. EtOAc (20 mL) was added to the combined NaHCO₃ layers, and the pH was adjusted to <3 using 6N HCl with efficient stirring. Once acidified, the aqueous layer was re-adjusted to pH 6-7 using saturated NaHCO₃. The aqueous and organic layers were partitioned and the aqueous layer was extracted with EtOAc (2×10 mL). The combined organic layers were dried (Na₂SO₄), filtered and the solvent removed under vacuum to afford the product (330 mg, 65%) as a solid. A sample was recrystallized from EtOAc. ¹H NMR (DMSO-d₆, 300 MHz) δ 9.04 (d, J=2.1 Hz, 1H), 8.60 (d, J=4.5 Hz, 1H), 8.22 (ddd, J=8.4, 2.7, 1.5 Hz, 1H), 7.58 (dd, J=8.4, 4.8, Hz, 1H), −1.1 (br. s, 1H); ¹³C NMR (DMSO-d₆, 75 MHz) δ 150.4, 148.5, 140.7, 131.1, 127.1, 124.2; m/z=162.20 [M−H]⁺; HRMS (EI): [M+H]⁺ calc'd for C₆H₅N₅O m/z 164.0572. found 164.0542.

Step 2: Preparation of methyl (E)-3-(5-oxo-4-(pyridin-3-yl)-4,5-dihydro-1H-tetrazol-1-yl)acrylate

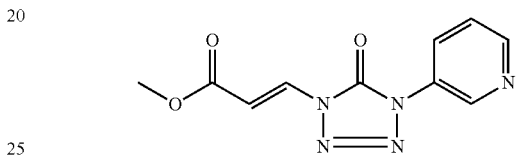

Method B to give the product as a solid. ¹H NMR (300 MHz, CDCl₃) δ 9.22 (d, J=2.4 Hz, 1H), 8.67 (dd, J=4.8, 1.5 Hz, Hz, 1H) 8.30 (ddd, J=8.4, 2.4, 1.5 Hz, 1H), 7.93 (d, J=14.4 Hz, 1H), 7.50 (dd, J=8.3, 4.8 Hz, 1H), 6.75 (d, J=14.4 Hz, 1H), 3.82 (s, 3H). ¹³C NMR (75 MHz, CDCl₃) δ 165.69, 148.76, 146.27, 140.17, 131.54, 130.93, 126.86, 124.14, 109.49, 52.18. LC/MS: rt 5.48 min (A), purity 98%, MS (m/e) 248 (MH⁺).

Compound 18: 2-(2,5-Dioxopyrrolidin-1-yl)ethyl (E)-3-(4-methyl-5-oxo-4,5-dihydro-1H-tetrazol-1-yl)acrylate

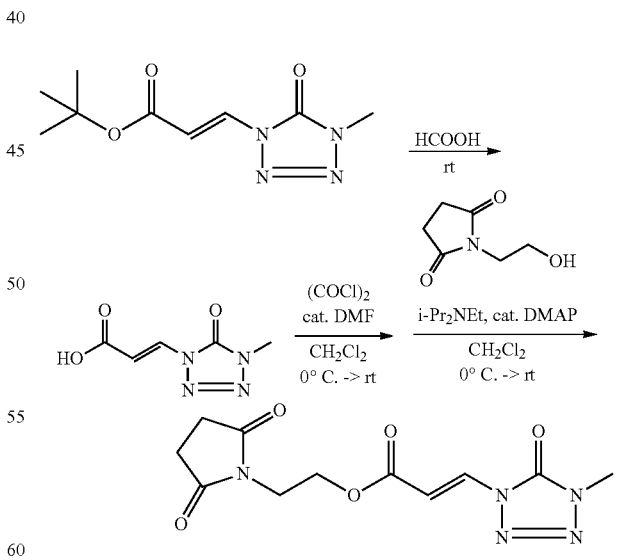

A homogeneous solution of tert-butyl (E)-3-(4-methyl-5-oxo-4,5-dihydro-1H-tetrazol-1-yl)acrylate (250 mg, 1.1 mmol) and formic acid (2 mL) was stirred at room temperature. After 1 h, LC/MS analysis of the resulting white heterogeneous slurry indicated complete consumption of tert-butyl (E)-3-(4-methyl-5-oxo-4,5-dihydro-1H-tetrazol- 1-yl)acrylate to (E)-3-(4-methyl-5-oxo-4,5-dihydro-1H-tetrazol-1-yl)acrylic acid. Upon concentration of reaction mixture by rotary evaporator under vacuum, the resulting white solid was stirred in water (5 mL), suction filtered and dried to provide (E)-3-(4-methyl-5-oxo-4,5-dihydro-1H-tetrazol-1-yl)acrylic acid (110 mg, 58%). $^1$H NMR (300 MHz, DMSO-$d_6$) δ 12.78 (s, 1H), 7.67 (d, J=14.4 Hz, 1H), 6.44 (d, J=14.4 Hz, 1H), 3.55 (s, 3H). $^{13}$C NMR (75 MHz, DMSO-$d_6$) δ 166.82, 148.83, 132.58, 108.56, 31.72. LC/MS: rt 3.70 min (A), purity 99%, MS (m/e) 212 (MH$^+$+CH$_3$CN); rt 1.92 min (B), purity 99%, MS (m/e) 169 (MH$^-$). A single necked pear shaped round bottom flask containing a stir bar and (E)-3-(4-methyl-5-oxo-4,5-dihydro-1H-tetrazol-1-yl)acrylic acid (100 mg, 0.58 mmol) was stoppered with a rubber septum and nitrogen was introduced. Dry CH$_2$Cl$_2$ (10 mL) was added and stirred for 5 min at 0° C. Subsequently, oxalyl chloride (0.3 mL, 430 mg, 3.4 mmol) was added to the above reaction mixture all at once and stirred for 5 min. Catalytic amount of dry DMF [0.3 mL stock solution of dry DMF (0.1 mL) dissolved in dry CH$_2$Cl$_2$ (4 mL)] was slowly added over a period of 3 min and stirred for 30 min. The resulting homogeneous solution was stirred at room temperature for 2 h and concentrated by rotary evaporator under vacuum to dryness. DMAP (14 mg, 0.11 mmol), N-(2-hydroxyethyl)succinimide (100 mg, 0.69 mmol) and dry CH$_2$Cl$_2$ (7 mL) were transferred to above acid chloride and stirred at 0° C. After 10 min, i-Pr$_2$NEt (0.3 mL, 220 mg, 1.76 mmol) was added drop-wise over a period of 5 min. After 30 min, the pale yellow homogeneous reaction mixture was stirred for 2 h at room temperature and concentrated by rotary evaporator under vacuum to dryness. The crude residue was partitioned between EtOAc (20 mL) and water (8 mL). Organic layer was separated, stirred over anhydrous Na$_2$SO$_4$ and filtered. Upon concentration of the filtrate, the crude residue was purified by Combiflash Teledyne® with RediSep® silica gel column 12 g using 30-70% EtOAc/hexanes as an eluting solvent to obtain 2-(2,5-dioxopyrrolidin-1-yl)ethyl (E)-3-(4-methyl-5-oxo-4,5-dihydro-1H-tetrazol-1-yl)acrylate (95 mg, 55%) as a white solid. $^1$H NMR (300 MHz, CDCl$_3$) δ 7.80 (d, J=14.4 Hz, 1H), 6.57 (d, J=14.4 Hz, 1H), 4.34 ((t, J=5.2 Hz, 2H), 3.82 (t, J=5.2 Hz, 2H), 3.63 (s, 3H), 2.70 (s, 4H). $^{13}$C NMR (75 MHz, CDCl$_3$) δ 176.95, 165.32, 148.46, 132.52, 107.99, 61.44, 37.85, 31.46, 28.12. LC/MS: rt 4.73 min (A), purity 98%, MS (m/e) 296 (MH$^+$).

Compound 21: Preparation of methyl (E)-3-(4-cyclopropyl-5-oxo-4,5-dihydro-1H-tetrazol-1-yl)acrylate

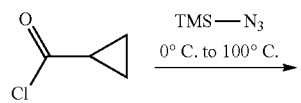

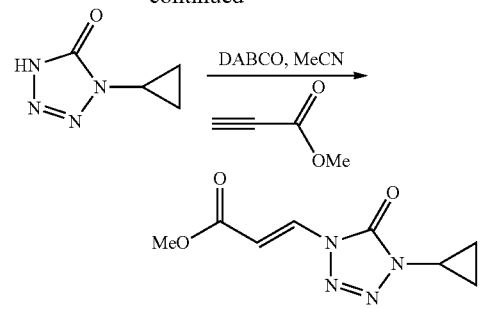

Step 1: Preparation of 1-cyclopropyl-1,4-dihydro-5H-tetrazol-5-one

A safety notice for the procedure: Azide compounds are potentially explosive. This reaction was performed behind a blast shield. Azidotrimethylsilane (40 mL, 300 mmol) was added in one portion to a stirred mixture of cyclopropanecarbonyl chloride (5.2 g, 50 mmol) at 0° C. under nitrogen. After complete addition, the cooling bath was removed and the mixture slowly heated to 100° C., then stirred at 100° C. overnight. After allowing to cool, the solvent was removed under vacuum to leave a crude residue. The residue was dry-loaded on to silica gel and purified by column chromatography on silica gel using DCM/20% MeOH in DCM (1:0 to 1:1) as eluent to give the product as a solid. $^1$H NMR (CDCl$_3$, 300 MHz) δ 3.33-3.25 (m, 1H), 1.20-1.12 (m, 4H); $^{13}$C NMR (CDCl$_3$, 75 MHz) δ 154.0, 26.2, 5.9.

Step 2: Preparation of methyl (E)-3-(4-cyclopropyl-5-oxo-4,5-dihydro-1H-tetrazol-1-yl)acrylate Method B to give the product as a solid after purification by column chromatography and high-performance liquid chromatography. $^1$H NMR (CDCl$_3$, 300 MHz) δ 7.84 (d, J=14.4 Hz, 1H), 6.64 (d, J=14.4 Hz, 1H), 3.81 (s, 3H), 3.26-3.32 (m, 1H), 1.14-1.21 (m, 4H); $^{13}$C NMR (CDCl$_3$, 75 MHz) δ 166.2, 148.8, 132.2, 108.6, 52.2, 26.9, 6.1; m/z=211.13 [M+H]$^+$& 252.18 [M+MeCN+H]$^+$; HRMS (EI): [M+MeCN+H]$^+$ calc'd for C$_8$H$_{10}$N$_4$O$_3$+MeCN m/z 252.1097. found 252.1105.

Example 2

Biological Activity of Compounds

Autoimmune Encephalitis (EAE) In Vivo Assay

Compounds disclosed herein were tested in an autoimmune encephalitis (EAE) in vivo assay in mice according to the methods described above in the paragraph entitled B.2. Experimental Autoimmune Encephalomyelitis Animal Model. Compound 1 (methyl (E)-3-(5-oxo-4,5-dihydro-1H-tetrazol-1-yl)acrylate) significantly prevented the onset of disease paralysis when dosed at 60 mg/kg beginning on the day of immunization.

NrF2 Activation in a Whole Cell Nuclear Translocation Assay

Compounds were tested in a NrF2 (Nuclear factor (erythroid-derived 2)-like 2) translocation assay by adapting the methods set forth in U.S. Pat. No. 8,101,373, the disclosure of which is incorporated herein by reference. The NrF2 activation exhibited by the present compounds demonstrates their anti-inflammatory activity.

Monomethyl fumarate and dimethyl fumarate exhibited NrF2 activation with EC50s of about 127 and 7.9 micromolar, respectively. As demonstrated in Table 3, compounds disclosed herein show comparable activity to monomethyl fumarate and dimethyl fumarate in the NrF2 translocation assay. In addition to monomethyl fumarate and dimethyl fumarate, bardoxolone methyl was used as a positive control (data not shown).

TABLE 3

| Compound | $X^1$ | $R^1$ | NrF2 translocation assay EC$_{50}$ (μM) |
|---|---|---|---|
| 1 | —CH$_3$ | H | 61 |
| 2 | —CH$_3$ | —CH$_3$ | 9.9 |
| 6 | —CH$_3$ | —CH(CH$_3$)$_2$ | 7.8 |
| 10 | —CH$_3$ | —C(O)N(CH$_3$)$_2$ | 6.1 |
| 11 | —CH$_3$ | -cyclopentyl | 5.4 |
| 12 | —CH$_3$ | 4-tetrahydropyranyl | 10.4 |
| 14 | —CH$_3$ | —CH$_2$C(O)OCH$_3$ | 6.7 |
| 16 | —CH$_3$ | phenyl | 1.0 |
| 17 | —CH$_3$ | 3-pyridyl | 1.0 |
| 20 | —CH$_3$ | 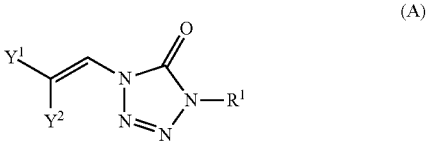 | 0.7 |
| 21 | —CH$_3$ | cyclopropyl | 7.2 |

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method of treating a disease or disorder in a subject in need thereof, the method comprising:
   administering to the subject a pharmaceutically effective amount of a compound of formula (A):

(A)

wherein either:
   $Y^1$ is $X^a$ and $Y^2$ is hydrogen, or $Y^2$ is $X^a$ and $Y^1$ is hydrogen;
   wherein $X^a$ is selected from carboxylic acid, carboxyl ester, heterocyclyl, substituted heterocyclyl, heteroaryl and substituted heteroaryl; and
   $R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (A);
   or a salt or stereoisomer thereof,
   wherein the administering is sufficient to treat the disease or disorder, and
   wherein the disease or disorder is psoriasis or multiple sclerosis.

2. The method of claim 1, wherein the compound is of formula (Ia) or (Ib):

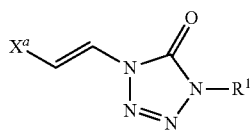

(Ia)

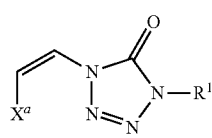

(Ib)

wherein $R^{15}$ comprises a linking group and a compound of formula (Ia) or (Ib).

3. The method of claim 1, wherein $X^a$ is a substituted heterocyclyl or a substituted heteroaryl, wherein the substituent on $X^a$ is $X^1$, wherein $X^1$ is $C_{1-6}$ alkyl or a progroup.

4. The method of claim 1, wherein the compound is a compound of formula (IIa) or (IIb):

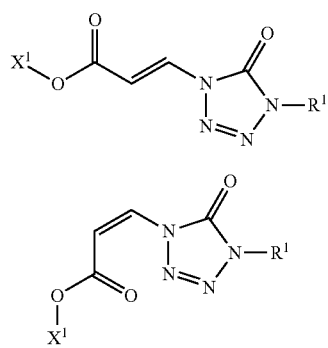

wherein
$R^1$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl and —$R^{15}$, wherein $R^{15}$ comprises a linking group and a compound of formula (IIa) or (IIb); and
$X^1$ is hydrogen, $C_{1-6}$ alkyl or a progroup;
or a salt or stereoisomer thereof.

5. The method of claim 4, wherein $R^1$ is aryl, substituted aryl, heteroaryl, or substituted heteroaryl.

6. The method of claim 4, wherein $R^1$ is hydrogen, alkyl, substituted alkyl, cycloalkyl, substituted cycloalkyl.

7. The method of claim 6, wherein $R^1$ is hydrogen, methyl, ethyl, isopropyl, cyclopentyl, 4-tetrahydropyranyl, —$CH_2CH_2OCH_3$, —$CH_2OCH_3$, —$CH_2C(O)OCH_3$, or —$CH_2CH(CH_3)_2OH$.

8. The method of claim 3, wherein $X^1$ is $C_{1-6}$ alkyl.

9. The method of claim 7, wherein $X^1$ is methyl or tert-butyl.

10. The method of claim 3, wherein $X^1$ is a progroup of the formula:

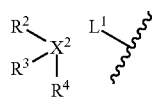

wherein
$L^1$ is a linking group;
$X^2$ is optional and selected from O, N and S;
$R^2$ is selected from hydrogen, alkyl, substituted alkyl, alkenyl, substituted alkenyl, alkynyl, substituted alkynyl, acyl, aminoacyl, carboxyl, carboxyl ester, cycloalkyl, substituted cycloalkyl, heterocyclyl, substituted heterocyclyl, aryl, substituted aryl, heteroaryl, and substituted heteroaryl; and
$R^3$ and $R^4$ are each independently optional and selected from hydrogen, alkyl, substituted alkyl, alkenyl, substituted alkenyl, alkynyl, substituted alkynyl, oxo, cycloalkyl, substituted cycloalkyl, heterocyclyl, substituted heterocyclyl, aryl, substituted aryl, heteroaryl, and substituted heteroaryl; or
$R^2$ together with $X^2$ and either $R^3$ or $R^4$ form a heterocyclyl, substituted heterocyclyl, heteroaryl or substituted heteroaryl.

11. The method of claim 10, wherein $X^1$ is selected from:

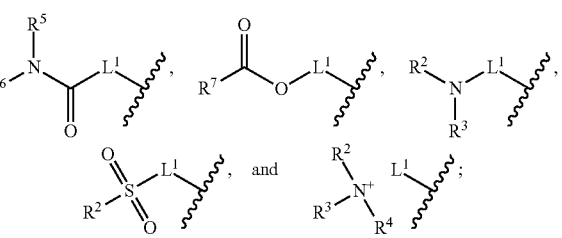

wherein
$L^1$ is a $C_{1-6}$ alkyl or substituted $C_{1-6}$ alkyl;
$R^5$ and $R^6$ are each independently selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl; or
$R^5$ and $R^6$ together with the nitrogen to which they are attached form a heterocyclyl, substituted heterocyclyl, heteroaryl or substituted heteroaryl; and
$R^7$ is selected from hydrogen, alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, substituted heteroaryl, and —$OR^{14}$ where $R^{14}$ is selected from alkyl, substituted alkyl, alkenyl, substituted alkenyl, alkynyl, substituted alkynyl, cycloalkyl, substituted cycloalkyl, heterocyclyl, substituted heterocyclyl, aryl, substituted aryl, heteroaryl, and substituted heteroaryl.

12. The method of claim 11, wherein $X^1$ is selected from:

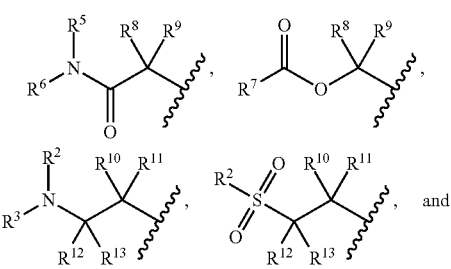

-continued

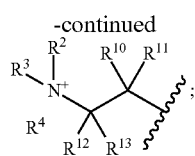

wherein
$R^8$, $R^9$, $R^{10}$, $R^{11}$, $R^{12}$ and $R^{13}$ are each independently selected from hydrogen, alkyl and substituted alkyl.

13. The method of claim 12, wherein $R^8$ and $R^9$ are each independently selected from hydrogen and $C_{1-6}$ alkyl.

14. The method of claim 13, wherein $R^8$ and $R^9$ are each hydrogen.

15. The method of claim 13, wherein $R^8$ is hydrogen and $R^9$ is $C_{1-6}$ alkyl.

16. The method of claim 12, wherein $R^{10}$, $R^{11}$, $R^{12}$ and $R^{13}$ are each independently selected from hydrogen and $C_{1-6}$ alkyl.

17. The method of claim 16, wherein $R^{10}$, $R^{11}$, $R^{12}$ and $R^{13}$ are each hydrogen.

18. The method of claim 16, wherein one of $R^{10}$, $R^{11}$, $R^{12}$ and $R^{13}$ is methyl and the remaining are hydrogen.

19. The method of claim 16, wherein two of $R^{10}$, $R^{11}$, $R^{12}$ and $R^{13}$ are methyl and the remaining are hydrogen.

20. The method of claim 1, wherein the linking group is —(CH$_2$)$_n$—Z$_y$—(CH$_2$)$_m$—,
wherein
n is an integer from 1 to 6;
m is 0 or an integer from 1 to 6;
y is 0 or 1; and
Z is O, NH, —O—P(O)(OH)—O—, S, S(O), SO$_2$ or —O—S(O)$_2$—O—.

21. The method of claim 20, wherein the compound has one of the following formulae:

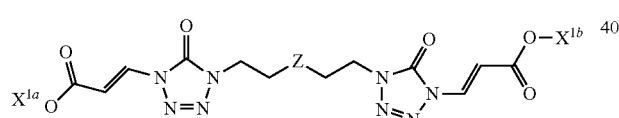

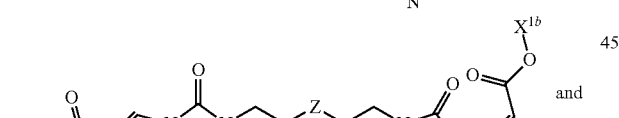

and

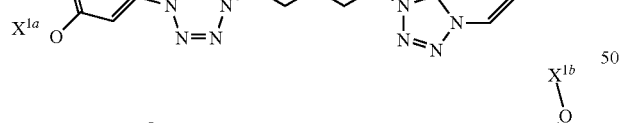

wherein
$X^{1a}$ and $X^{1b}$ are each independently selected from $C_{1-6}$ alkyl and a progroup; and
Z is O, NH, —O—P(O)(OH)—O—, S, S(O), SO$_2$ or —O—S(O)$_2$—O—.

22. The method of claim 1, wherein $R^1$ is:

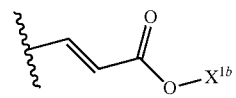

wherein $X^{1b}$ is selected from $C_{1-6}$ alkyl and a progroup.

23. The method of claim 22, wherein the compound has one of the following formulae:

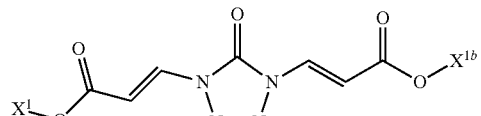

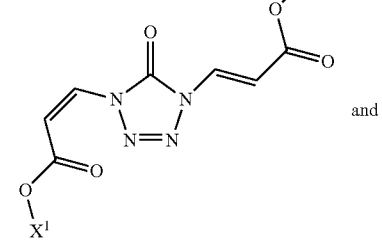

and

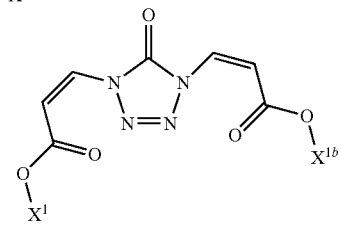

wherein $X^1$ and $X^{1b}$ are each independently selected from $C_{1-6}$ alkyl and a progroup.

24. The method of claim 23, wherein $X^1$ and $X^{1b}$ are each independently a $C_{1-6}$ alkyl.

25. The method of claim 24, wherein the compound has the structure:

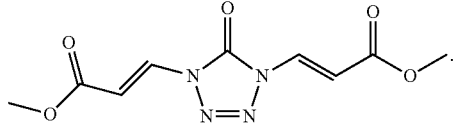

26. The method of claim 1, wherein the compound is selected from:

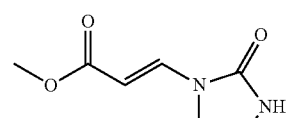

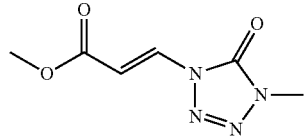

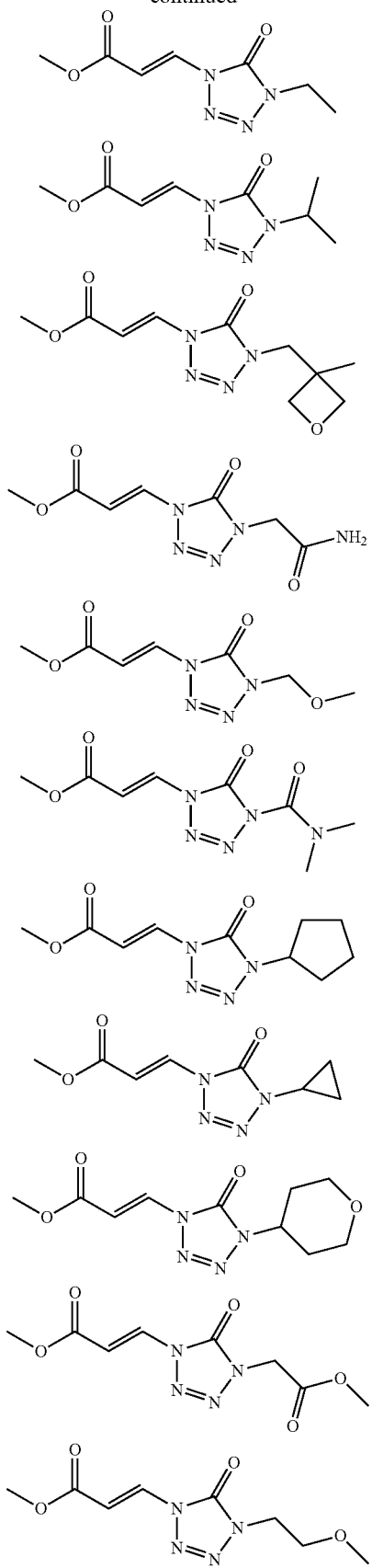
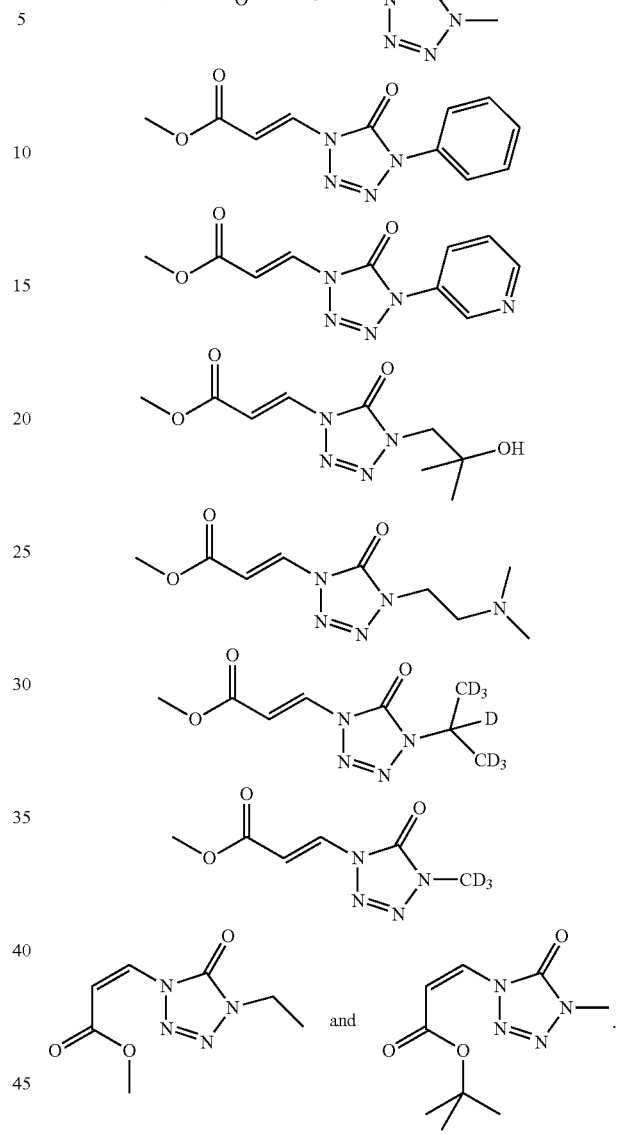
27. The method of claim 1, wherein the compound is selected from:
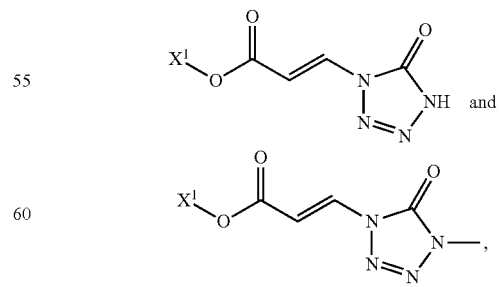
wherein $X^1$ is a progroup.
* * * * *

UNITED STATES PATENT AND TRADEMARK OFFICE
CERTIFICATE OF CORRECTION

PATENT NO. : 9,801,866 B2
APPLICATION NO. : 15/269233
DATED : October 31, 2017
INVENTOR(S) : Matthew Duncton Page 1 of 1

It is certified that error appears in the above-identified patent and that said Letters Patent is hereby corrected as shown below:

On the Title Page

The Assignee "Rigl Pharmaceutical, Inc., South San Francisco, CA (US)" should read -- Rigel Pharmaceuticals, Inc., South San Francisco, CA (US) --

Signed and Sealed this
Twenty-sixth Day of December, 2017

Joseph Matal
*Performing the Functions and Duties of the*
*Under Secretary of Commerce for Intellectual Property and*
*Director of the United States Patent and Trademark Office*

```
                       SEQUENCE LISTING

<160> NUMBER OF SEQ ID NOS: 1

<210> SEQ ID NO 1
<211> LENGTH: 21
<212> TYPE: PRT
<213> ORGANISM: Artificial Sequence
<220> FEATURE:
<223> OTHER INFORMATION: Synthetic amino acid sequence

<400> SEQUENCE: 1

Met Glu Val Gly Trp Tyr Arg Ser Pro Phe Ser Arg Val Val His Leu
1               5                   10                  15

Tyr Arg Asn Gly Lys
            20
```